(12) United States Patent
Maheswaran et al.

(10) Patent No.: US 10,094,837 B2
(45) Date of Patent: Oct. 9, 2018

(54) CADHERINS AS CANCER BIOMARKERS

(71) Applicant: The General Hospital Corporation, Boston, MA (US)

(72) Inventors: Shyamala Maheswaran, Lexington, MA (US); David Tsai Ting, Dover, MA (US); Daniel A. Haber, Chestnut Hill, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/236,851

(22) Filed: Aug. 15, 2016

(65) Prior Publication Data

US 2016/0349264 A1 Dec. 1, 2016

Related U.S. Application Data

(62) Division of application No. 14/347,898, filed as application No. PCT/US2012/058069 on Sep. 28, 2012, now Pat. No. 9,417,244.

(60) Provisional application No. 61/540,380, filed on Sep. 28, 2011.

(51) Int. Cl.
*G01N 33/53* (2006.01)
*G01N 33/574* (2006.01)

(52) U.S. Cl.
CPC ............ *G01N 33/57492* (2013.01); *G01N 2333/4727* (2013.01)

(58) Field of Classification Search
None
See application file for complete search history.

(56) References Cited

U.S. PATENT DOCUMENTS

| | | | | |
|---|---|---|---|---|
| 8,921,102 B2* | 12/2014 | Fuchs | ............... | B01L 3/502707 435/173.9 |
| 9,128,082 B2* | 9/2015 | Mikolajczyk | .... | G01N 33/54306 |
| 2010/0310451 A1 | 12/2010 | Maret et al. | | |
| 2011/0147218 A1 | 6/2011 | Meyer et al. | | |
| 2014/0220580 A1* | 8/2014 | Brown | ............. | G01N 33/57434 435/6.12 |

FOREIGN PATENT DOCUMENTS

| WO | 2009/051734 | | 4/2009 |
|---|---|---|---|
| WO | 2010/036912 | | 4/2010 |
| WO | WO 2010/036912 | * | 4/2010 |

OTHER PUBLICATIONS

Armstrong et al., Mol. Cancer Research, 9:997-1007 (2011, published online Jun. 10, 2011).
Berx and van Roy, "Involvement of Members of the Cadherin Superfamily in Cancer," Cold Spring Harb Perspect Biol., 2009, 1:a003129, 28 pages.
Contreras et al., "The expression of syndecan-1 and -2 is associated with Gleason score and epithelial-mesenchymal transition markers, E-cadherin and beta-catenin, in prostate cancer," Urol Oncol., 2010, 28:534-40.
Gravdal et al., "A switch from E-cadherin to N-cadherin expression indicates epithelial to mesenchymal transition and is of strong and independent importance for the progress of prostate cancer," Clin Cancer Res., 2007, 13:7003-11.
Han and Frazier, "Paramagnetic capture mode magnetophoretic microseparator for blood cells," IEE Proc Nanobiotechnol., Aug. 2006, 153(4):67-73.
International Preliminary Report on Patentability in International Application No. PCT/US2012/058069, dated Apr. 10, 2014, 6 pages.
International Search Report and Written Opinion dated Jan. 17, 2013 for international application No. PCT/US2012/058069, 7 pgs.
Kim et al., "Aberrant methylation of E-cadherin and H-cadherin genes in nonsmall cell lung cancer and its relation to clinicopathologic features," Cancer, 2007, 110(12):2785-92.
Man et al., "Currently Used Markers for CTC Isolation—Advantages, Limitations and Impact on Cancer Prognosis," J Clinic Experiment Pathol., 2011, 1(1):1000102, 7 pages.
Miotto et al., "Frequent Aberrant Methylation of the CDH4 Gene Promoter in Human Colorectal and Gastric Cancer," Cancer Res., 2004, 64:8156-8159.
Peinado et al., "Transcriptional regulation of cadherins during development and carcinogenesis," Int J Dev Biol., 2004, 48(5-6):365-75.
Redies et al., "δ-Protocadherins: unique structures and functions," Cell Mol Life Sci., 2005, 62:2840-2852.
Stott et al., "Isolation of circulating tumor cells using a microvortex-generating herringbone-chip," PNAS, 2010, 107(43):18392-7.
Takeichi, "Cadherins in cancer: implications for invasion and metastasis," Current Opinion Cell Biol., 1993, 5:806-811.
Tanaka et al., "Monoclonal antibody targeting of N-cadherin inhibits prostate cancer growth, metastasis and castration resistance," Nat Med., 2010, 16:1414-20 (Author Manuscript).
Thedieck et al., "Cadherin-9 Is a Novel Cell Surface Marker for the Heterogeneous Pool of Renal Fibroblasts," PLoS One, Aug. 2007, 8:e657, 14 pages.
Tomita et al., "Cadherin switching in human prostate cancer progression," Cancer Res., 2000, 60:3650-4.

(Continued)

*Primary Examiner* — Laura B Goddard
(74) *Attorney, Agent, or Firm* — Fish & Richardson P.C.

(57) ABSTRACT

Methods of isolating, enriching, capturing, identifying, or detecting the presence of, cancerous cells in a sample, e.g., a blood sample from a subject, by detecting the presence of one or more cancer cell surface markers selected from the group consisting of cadherin 1 (CDH1), CDH2, CDH3, CDH4, CDH5, CDH9, CDH11, CDH17, CDH19, protocadherin 9 (PCDH9) and/or PCDH beta 13 (PCDHb13), and optionally an additional cancer cell surface marker, e.g., EpCAM, MUC1, EphB4, EGFR, CEA, and/or HER2.

16 Claims, 57 Drawing Sheets

(56) References Cited

OTHER PUBLICATIONS

Zhau et al., "Epithelial to mesenchymal transition (EMT) in human prostate cancer: lessons learned from ARCaP model," Clin Exp Metastasis, 2008, 25:601-10 (Author Manuscript).

* cited by examiner

FIG. 2

| | Breast | Brain | Lung | Prostate | Pancreatic | Melanoma | Whole Blood | Pubmed hits |
|---|---|---|---|---|---|---|---|---|
| Cadherins | | | | | | | | |
| cdh1 | | | 2.35 | 4.1 | | 9.9 | under | 730 |
| cdh2 | 2.1 | 3.9 | 5.95 | | 94 | | under | 67 |
| cdh3 | | 14.3 | 10.35 | | 3 | | under | 28 |
| cdh4 | | | | | | | under | 4 |
| cdh5 | | 9.8 | | | | | under | 11 |
| cdh6 | | 2.9 | | | 2 | | over | 6 |
| cdh11 | 14.2 | 2.75 | | | 7.1 | 2.8 | under | 17 |
| cdh12 | 3.4 | | 3.65 | | | | under | 3 |
| cdh13 | | 7.8 | | | | | under | 126 |
| cdh17 | | 3.1 | | | 39.3 | | under | 41 |
| cdh19 | | 16 | | | | | under | 2 |
| cdh25 | | 5.7 | | | | | | |
| cdh27 | 2.4 | | | | | | | |
| | | | | | | | | |
| Desmosomal | | | | | | | | |
| dsg2 | | | 3.6 | | 3.95 | | under | 47 |
| dsg3 | | | 3 | | 2.3 | 2.5 | over | 73 |
| dsc1 | | 2.1 | | | | | | 19 |
| dsc2 | | 3.4 | 4.9 | 3.3 | | | over | 24 |
| dsc3 | | | 8.8 | | | | under | 19 |
| | | | | | | | | |
| Protocadherins | | | | | | | | |
| PCDH1 | | | | | 4.3 | | under | 3 |
| PCDH2 | | 4.65 | 3.75 | | | 3.2 | under | 1 |
| PCDH7 | 2.2 | | 4.3 | | 3.9 | 2.9 | over | 6 |
| PCDH12 | | 8.1 | | | | | under | 1 |
| PCDH17 | 3.5 | | | | | 2.6 | under | 5 |
| PCDH18 | | 2.95 | | | | | | 2 |
| PCDHA9 | | 3 | | | | | under | 0 |
| PCDHA11 | 2.3 | | | | | | | 0 |
| PCDHB3 | | 3 | | | | | under | 0 |
| PCDHB5 | | 2 | | | | | | 0 |
| PCDHB6 | | 2.2 | | | | | under | 0 |
| PCDHB7 | | 2.25 | | | | | | 0 |
| PCDHB9 | | 3.5 | | | | | | 0 |
| PCDHB10 | | | | | 2.6 | | | 0 |
| PCDHB11 | | 4.5 | | | | | under | 0 |
| PCDHB12 | 2 | 2.2 | | | | | under | 0 |
| PCDHB13 | | 2.7 | | | | | under | 0 |
| PCDHB14 | | | | | 2.5 | | | 0 |
| PCDHB16 | 2.2 | 3.1 | | | | | | 0 |
| PCDHB18 | | 2.5 | | | | | | 0 |
| PCDHGA1 | | | | | | 3.1 | under | 0 |
| PCDHGA3 | | 2.55 | | 2.5 | | 14.05 | over | 1 |
| PCDHGA4 | | 2.75 | | | | | | 0 |
| PCDHGA8 | | 5.55 | | | | | | 0 |
| PCDHGA10 | | 3.1 | | | | | over | 0 |
| PCDHGB1 | 2.3 | | | | | | | 0 |
| PCDHGB7 | | 5.3 | | | | | | 1 |
| PCDHGC3 | | 2.4 | | | | 2.3 | under | 1 |
| PCDHGC5 | 2.4 | | | | | | | 0 |

US 10,094,837 B2

CADHERINS AS CANCER BIOMARKERS

CLAIM OF PRIORITY

This application is a divisional of U.S. patent application Ser. No. 14/347,898, filed Mar. 27, 2014, which is a U.S. National Phase Application under 35 U.S.C. § 371 of International Patent Application No. PCT/US2012/058069, filed on Sep. 28, 2012, which claims the benefit of U.S. Provisional Patent Application Ser. No. 61/540,380, filed on Sep. 28, 2011; the entire contents of the foregoing are hereby incorporated by reference.

TECHNICAL FIELD

This invention relates to methods of isolating, identifying, or detecting the presence of, cancerous cells in a sample, by detecting the presence of one or more cancer cell surface markers selected from the group consisting of cadherin 1 (CDH1), CDH2, CDH3, CDH4, CDH5, CDH9, CDH11, CDH17, CDH19, protocadherin 9 (PCDH9) and/or PCDH beta 13 (PCDHb13), optionally with the addition of one or more other cancer cell surface markers, e.g., EpCAM, MUC1, EphB4, EGFR, CEA, and/or HER2.

BACKGROUND

Circulating tumor cells (CTCs) offer a non-invasive means to serially sample tumor cells from patients with solid malignancies. Most current CTC capture devices rely on immunoaffinity using antibodies directed against epithelial cell adhesion molecule (EpCAM). This particular capture epitope is attractive for its presence in a wide variety of epithelial cancers, but relative absence in normal blood cells. This provides a strategy to specifically capture tumor cells in the blood of patients. However, there are variations of EpCAM levels between tumors, so a multiple epitope strategy could be more inclusive. Furthermore, there is indication that EpCAM is lost during the process of epithelial to mesenchymal transition (EMT), which has been implicated in metastasis. Therefore, the identification of novel CTC capture epitopes to deal with tumor epitope heterogeneity as well as potential biologically important changes in tumor cell surface epitopes is important to capture the full spectrum of CTCs.

SUMMARY

The present invention is based, at least in part, on the discovery that certain cadherins are selectively expressed on CTCs and thus can be used to detect, identify, isolate, and monitor the presence of CTCs in a sample.

Thus in one aspect, the invention features methods for detecting the presence of a circulating tumor cell (CTC) in a sample from a subject. The methods include providing a sample comprising blood from a subject; and contacting the sample with one or more agents that bind to a cancer cell surface marker selected from the group consisting of cadherin 1 (CDH1), CDH2, CDH3, CDH4, CDH5, CDH9, CDH11, CDH17, CDH19, protocadherin 9 (PCDH9) and/or PCDH beta 13 (PCDHb13); and detecting the binding of the agent to a cancer cell surface marker present on a cell in the sample; thereby detecting the presence of a cancer cell in the sample.

In a further aspect, the invention features method of capturing (e.g., isolating and/or enriching) a circulating tumor cell (CTC) from a sample. The methods include providing a sample comprising blood from a subject; and contacting the sample with one or more agents that bind to a cancer cell surface marker selected from the group consisting of cadherin 1 (CDH1), CDH2, CDH3, CDH4, CDH5, CDH9, CDH11, CDH17, CDH19, protocadherin 9 (PCDH9) and/or PCDH beta 13 (PCDHb13), under conditions sufficient to allow binding of the agent to cells expressing the surface marker; and isolating a cell expressing a cancer cell surface marker from the sample; thereby capturing a CTC from the sample.

In an additional aspect, the invention features methods for diagnosing cancer in a subject. The methods include providing a sample comprising blood from the subject; contacting the sample with one or more agents that bind to a cancer cell surface marker selected from the group consisting of cadherin 1 (CDH1), CDH2, CDH3, CDH4, CDH5, CDH9, CDH11, CDH17, CDH19, protocadherin 9 (PCDH9) and/or PCDH beta 13 (PCDHb13), under conditions sufficient to allow binding of the agent to cells expressing the surface marker; and detecting the binding of the agent to a cancer cell surface marker present on a cell in the sample; wherein the presence of binding to a cell in the sample indicates that the subject has cancer.

In yet another aspect, the invention features methods for monitoring development or progression of cancer in a subject. The methods include providing a first sample comprising blood from the subject; contacting the first sample with one or more agents that bind to a cancer cell surface marker selected from the group consisting of cadherin 1 (CDH1), CDH2, CDH3, CDH4, CDH5, CDH9, CDH11, CDH17, CDH19, protocadherin 9 (PCDH9) and/or PCDH beta 13 (PCDHb13), under conditions sufficient to allow binding of the agent to cells expressing the surface marker; detecting the presence or absence of binding of the agent to a cancer cell surface marker present on a cell in the first sample; providing a subsequent sample comprising blood from the subject; contacting the subsequent sample with one or more agents that bind to a cancer cell surface marker selected from the group consisting of cadherin 1 (CDH1), CDH2, CDH3, CDH4, CDH5, CDH9, CDH11, CDH17, CDH19, protocadherin 9 (PCDH9) and/or PCDH beta 13 (PCDHb13), under conditions sufficient to allow binding of the agent to cells expressing the surface marker; and detecting the presence or absence of binding of the agent to a cancer cell surface marker present on a cell in the subsequent sample.

In some embodiments, the surface markers include cadherins 1, 2, 3, 5, and 11. In some embodiments, the surface markers include cadherins 1, 2, 3, 5, 11, and EpCAM. In some embodiments, the surface markers include cadherins 3 and 11. In some embodiments, the surface markers include cadherins 3, 11, and EpCAM.

In some embodiments of the methods described herein, the absence of binding to a cell in both the first and subsequence sample indicates that the subject has not developed cancer. In some embodiments of the methods described herein, the absence of binding to a cell in the first sample, and the presence of binding to a cell in a subsequence sample indicates that the subject has developed cancer.

In some embodiments, the methods described herein include quantifying a level of surface marker-expressing cells in the first and subsequent samples, wherein an increase in the number of cells that express the one or more surface markers indicates that cancer is progressing in the subject; a decrease in the number of cells that express the one or more surface markers indicates that cancer is regressing in the subject; and no significant change in the number of cells that express the one or more surface markers indicates that cancer is stable in the subject.

In some embodiments of the methods described herein, the one or more agents that bind to a cancer cell surface marker are in a microfluidic device.

In some embodiments of the methods described herein, the one or more agents that bind to a cancer cell surface marker are coated on a surface, e.g., a bead, post or obstacle, e.g., a magnetic bead.

In some embodiments of the methods described herein, the one or more agents that bind to a cancer cell surface marker are antibodies or antigen-binding fragments thereof.

In some embodiments of the methods described herein, wherein the one or more agents that bind to a cancer cell surface marker bind to CDH4 or CDH9.

In some embodiments of the methods described herein, the method is performed using a microfluidic device. In some embodiments of the methods described herein, the microfluidic device separates tumor cells based on inertial lift forces or fluid flow patterns.

In a further aspect the invention provides devices for isolation, enrichment, separation, or detection of cells, e.g., tumor cells, in a sample. The devices comprise an inlet, and outlet, and one or more areas coated with an agent that binds a cancer cell surface marker selected from the group consisting of cadherin 1 (CDH1), CDH2, CDH3, CDH4, CDH5, CDH9, CDH11, CDH17, CDH19, protocadherin 9 (PCDH9) and/or PCDH beta 13 (PCDHb13), configured to separate, isolate, enrich, or detect cells that express the cancer cell surface marker, e.g., from cells that do not express the cancer cell surface marker. In some embodiments, the surface markers include cadherins 1, 2, 3, 5, and 11. In some embodiments, the surface markers include cadherins 1, 2, 3, 5, 11, and 17. In some embodiments, the surface markers include cadherins 3 and 11. In some embodiments, the surface markers include cadherins 3, 11, and EpCAM.

In some embodiments of the methods described herein, the device is a microfluidic device. In some embodiments of the methods described herein, the device comprises a microchannel disposed between the inlet and the outlet, and a herringbone pattern formed by arranging grooves in the micro-channel, and the agent that binds the cancer cell surface marker is disposed on one or more of walls of the microchannel.

In some embodiments, the cancer is of epithelial origin, or of mesenchymal origin.

In general, the methods described herein are in vitro methods.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 2 is a table showing the results of analysis of candidate cadherins using Oncomine™ expression database.

FIG. 3, EpCAM; FIGS. 4-5, CDH1; FIGS. 6-7, CDH2; FIG. 8, CDH3; FIGS. 9-12, CDH4; FIG. 13, CDH5; FIGS. 14-18, CDH6; FIGS. 19-20, CDH7; FIGS. 21-22, CDH8; FIG. 23, CDH9; FIG. 24, CDH10; FIGS. 25-27, CDH11; FIG. 28, CDH12; FIG. 29, CDH13; FIGS. 30-31, CDH15; FIG. 32, CDH16; FIG. 33, CDH17; FIG. 34, CDH18; FIGS. 35-36, CDH19; FIG. 37, CDH20; FIGS. 38-39, CDH22; FIGS. 40-43, CDH23; FIGS. 44-45, CDH24; and FIGS. 46-49, CDH26.

DETAILED DESCRIPTION

Figure 1:
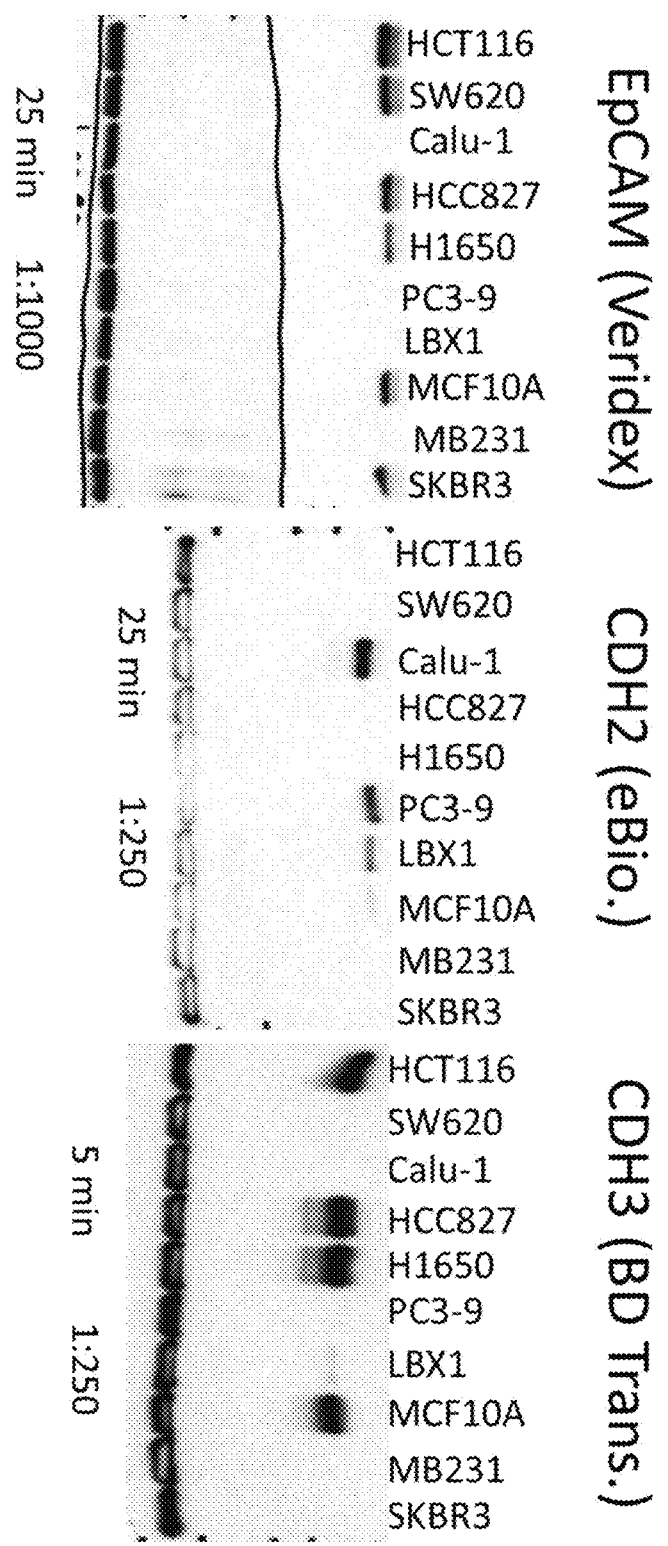
FIG. 1 is a set of three images showing the results of Western blot analysis of EpCAM, CDH2 and CDH3 expression using a commercially available antibodies (Veridex, eBio, and BD, respectively) in ten cancer cell lines (HCT116, SW620, CaLu-1, HCC827, H1650, PC3-9, LBX-1, MCF10A, MDA-MB-231, and SKBR3). CaLu1, PC3-9, and LBX1, which are negative for the EpCAM epitope, are positive for CDH2. Band is at approximately 100 kD. This combination of antibodies was able to capture all 10 cell lines tested, including both mesenchymal- and epithelial-derived tumor cells.
Figure 3:
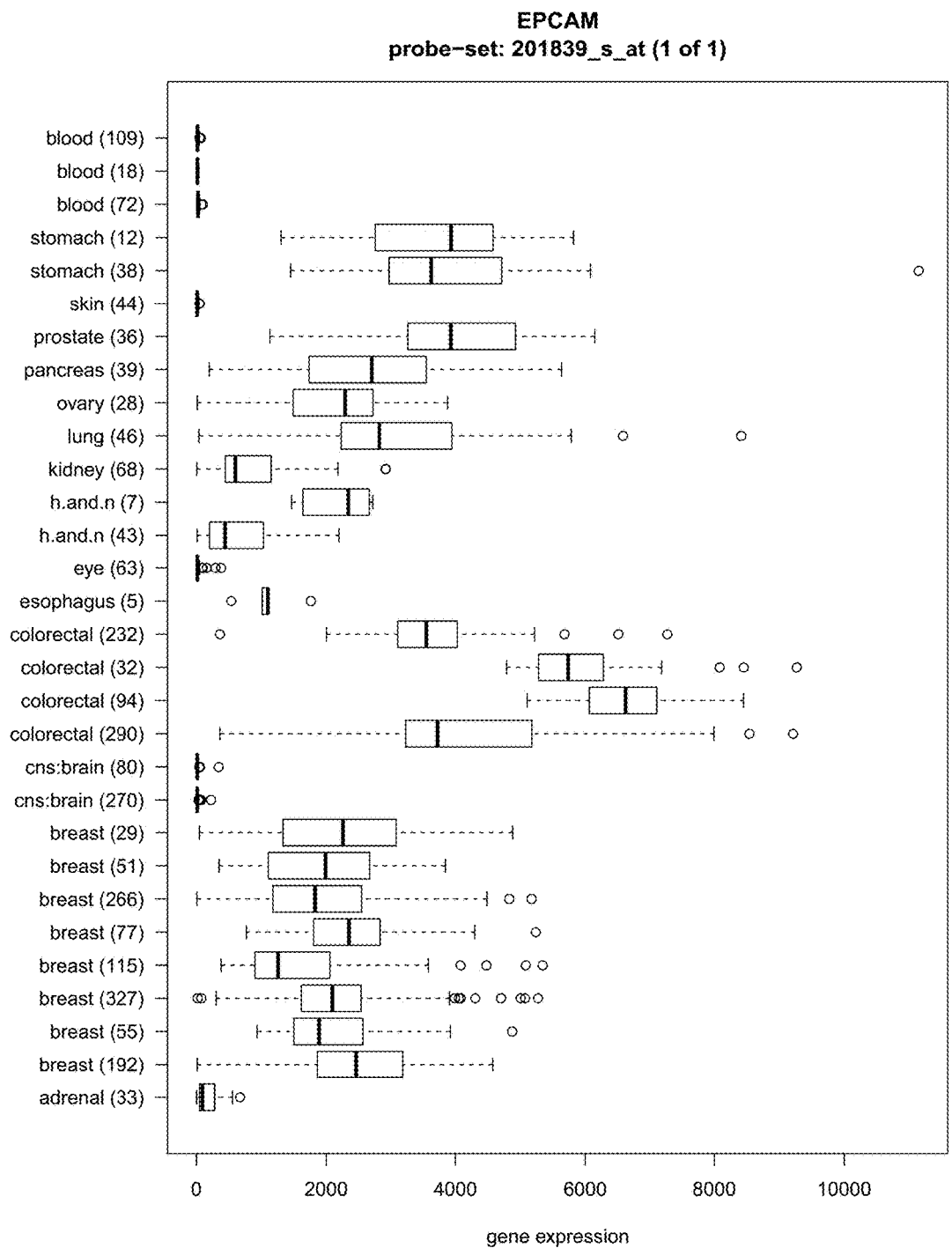
FIGS. 3-49 are box plots showing the levels of expression of various cell surface markers.
Figure 4:
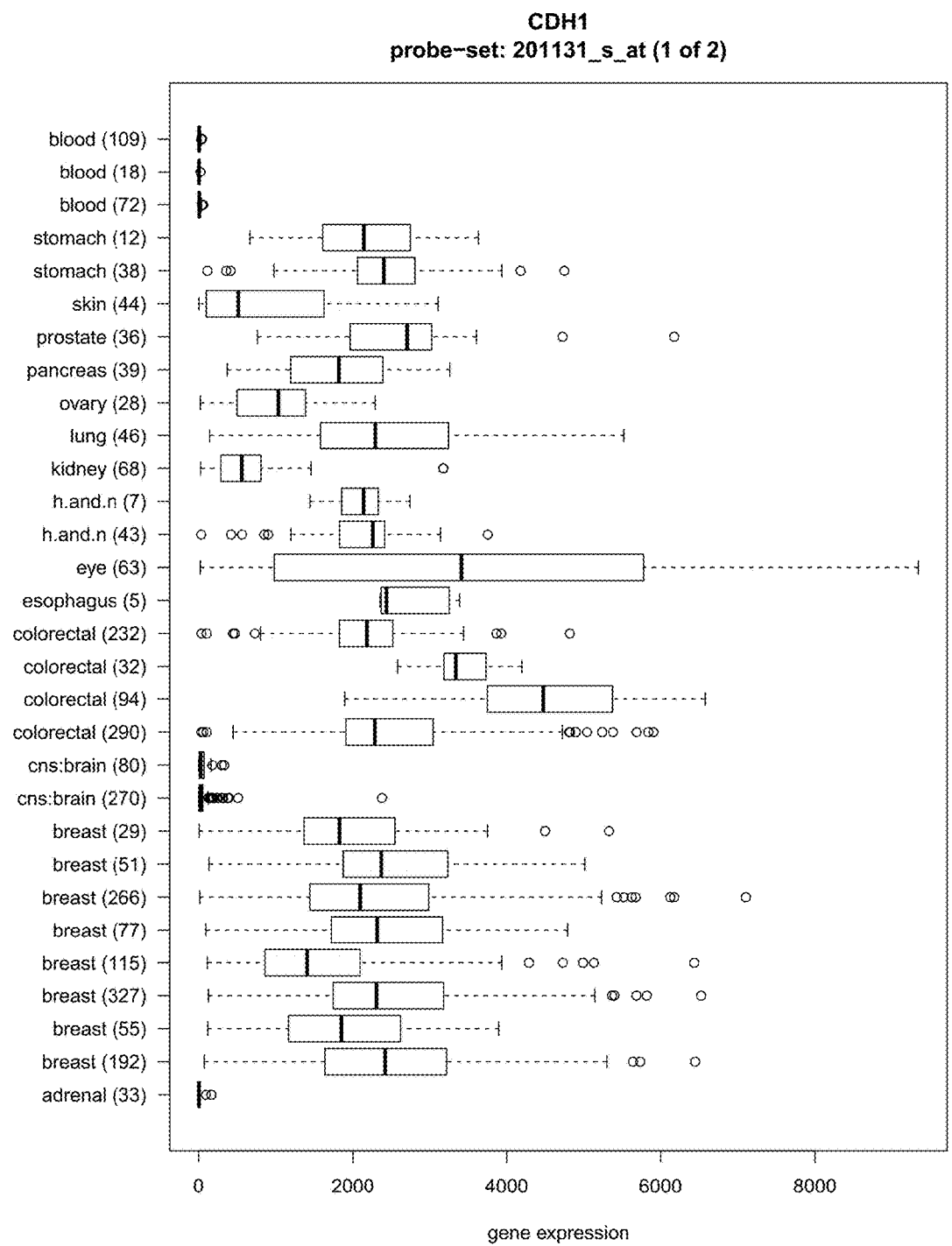
Figure 5:
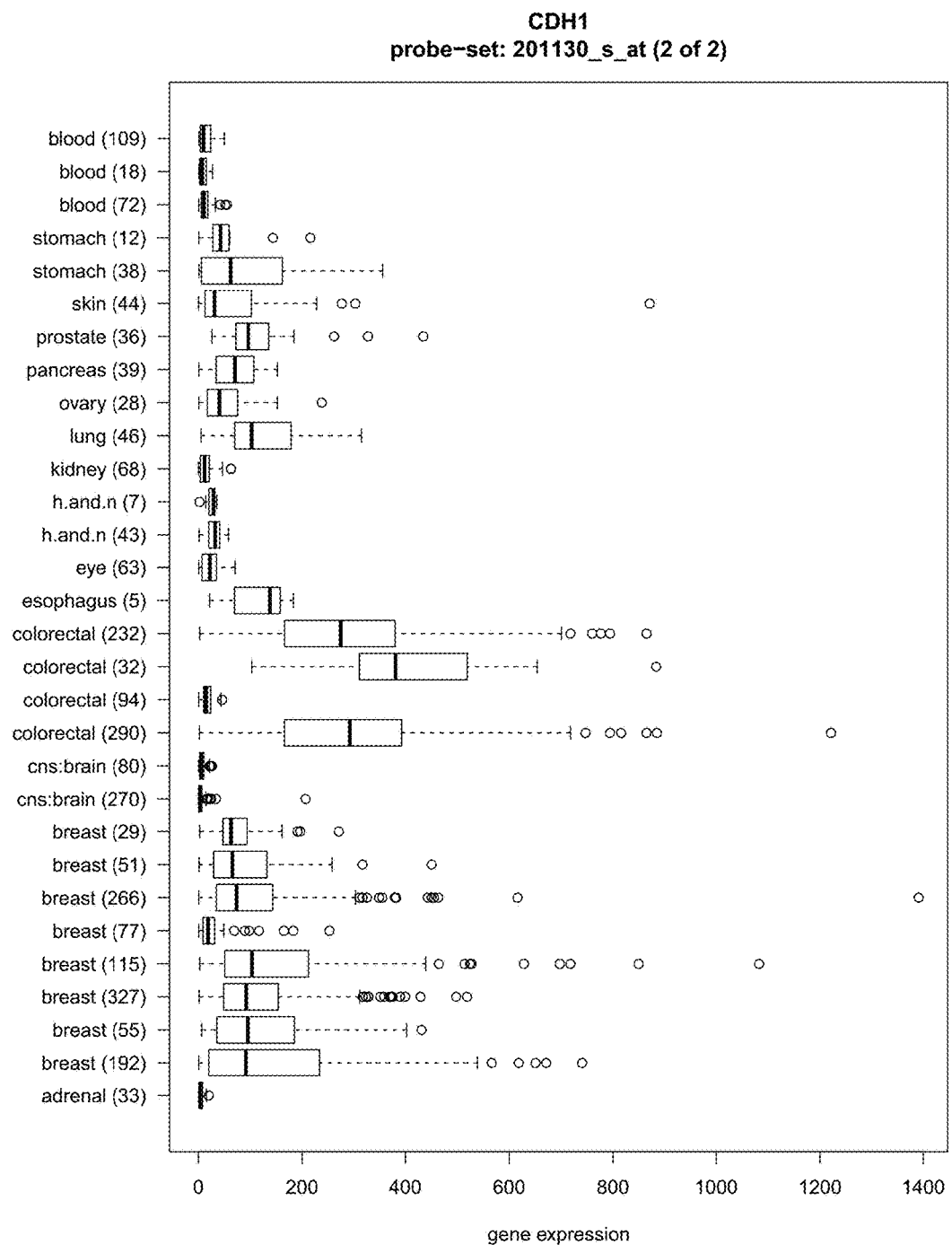
Figure 6:
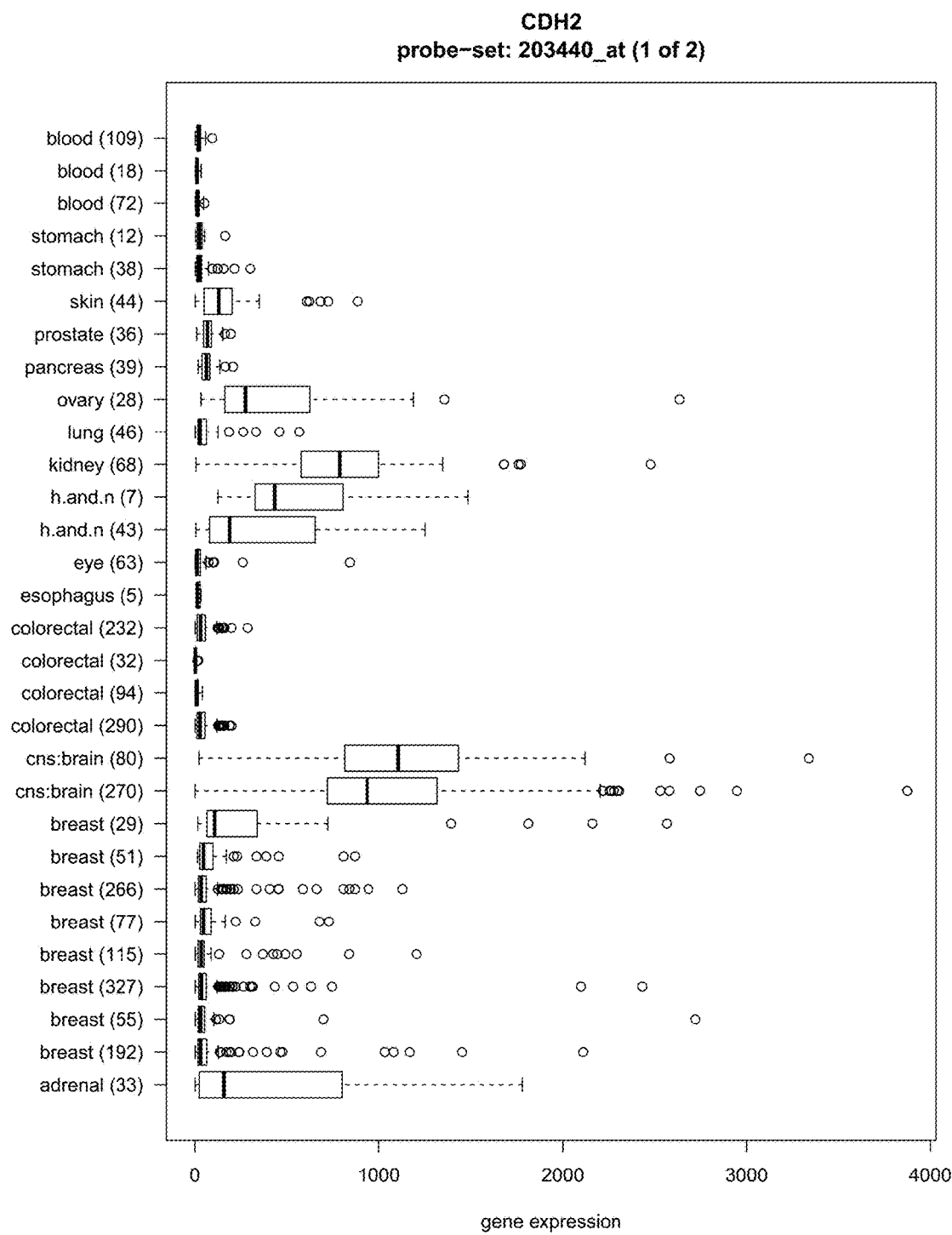
Figure 7:
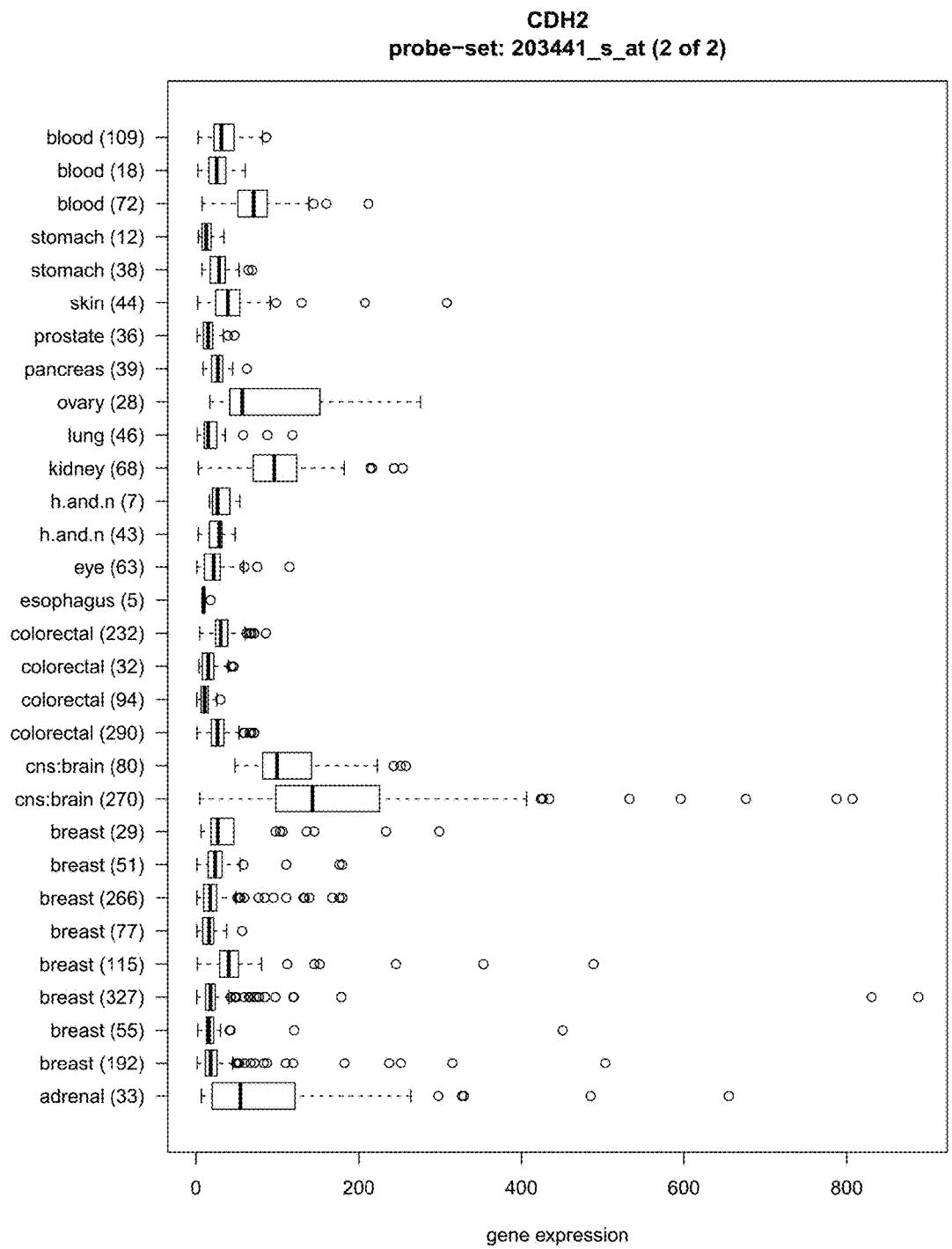
Figure 8:
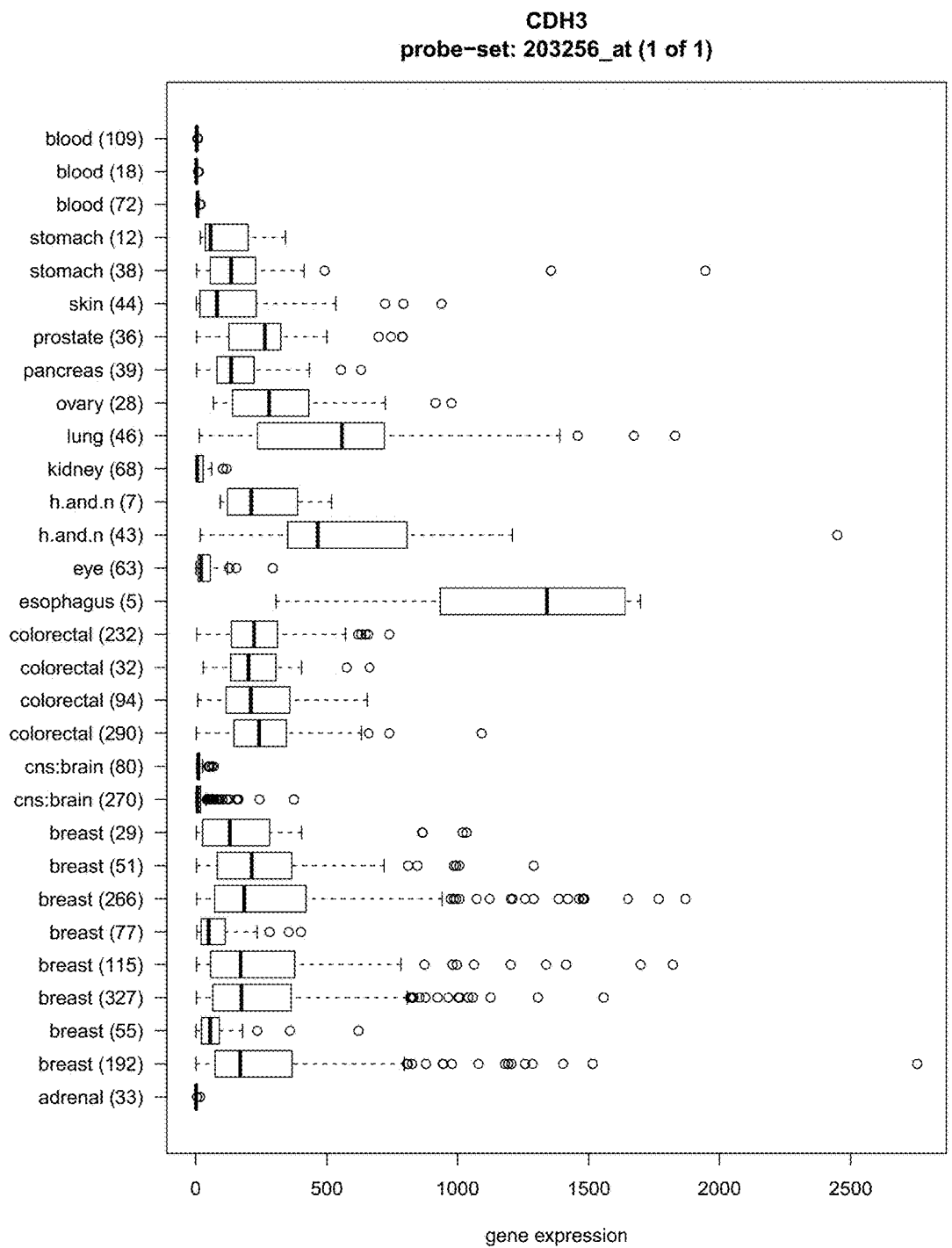
Figure 9:
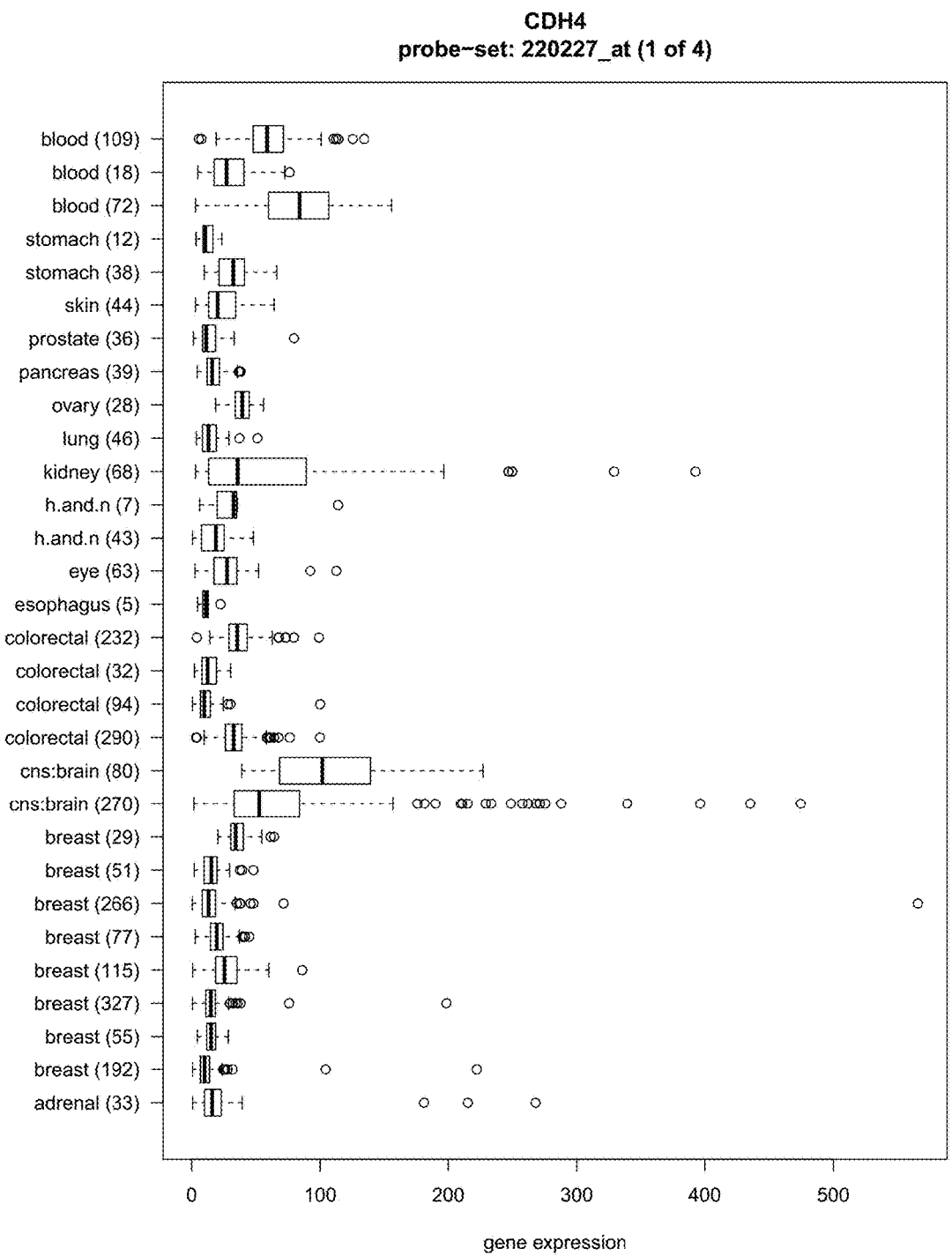
Figure 10:
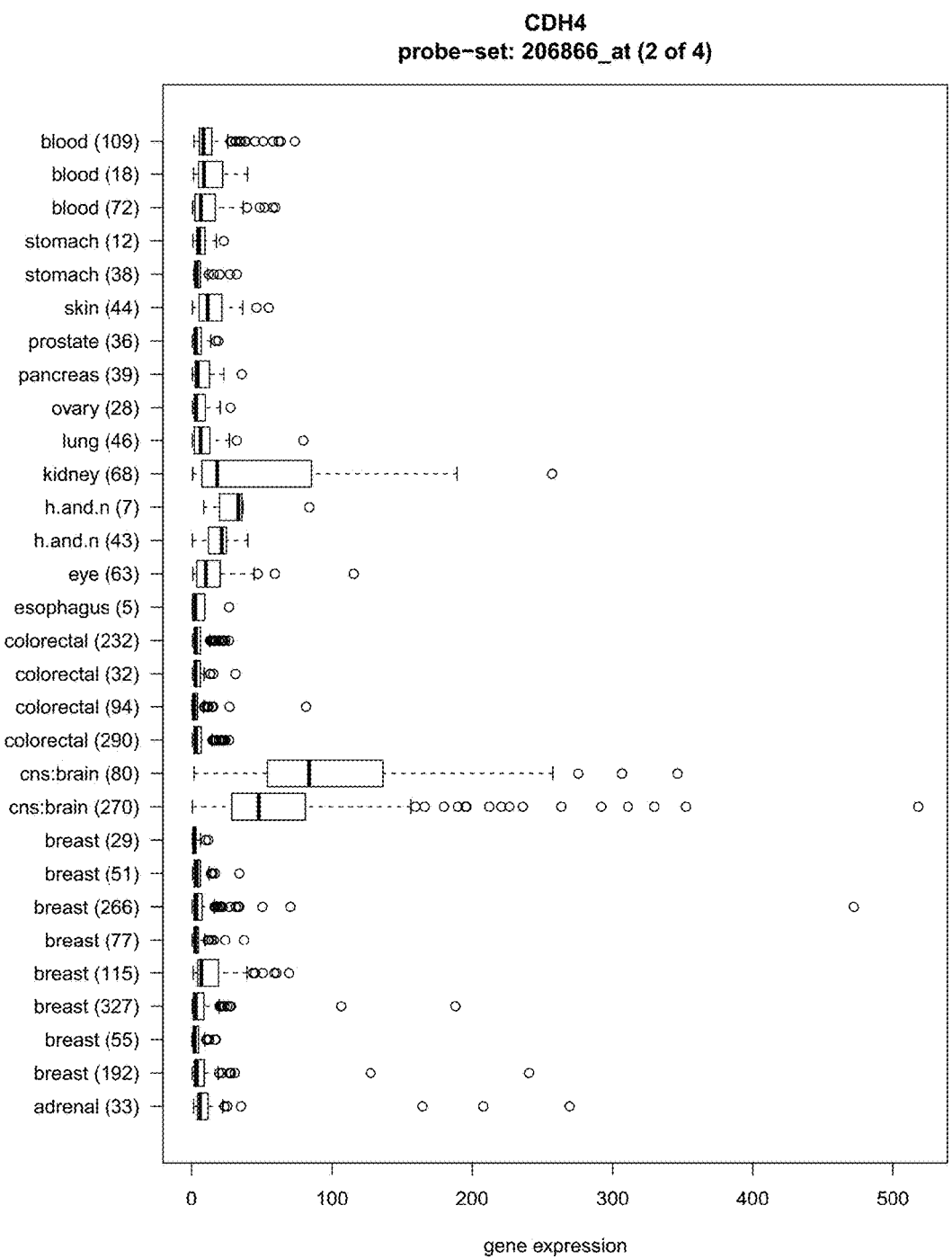
Figure 11:
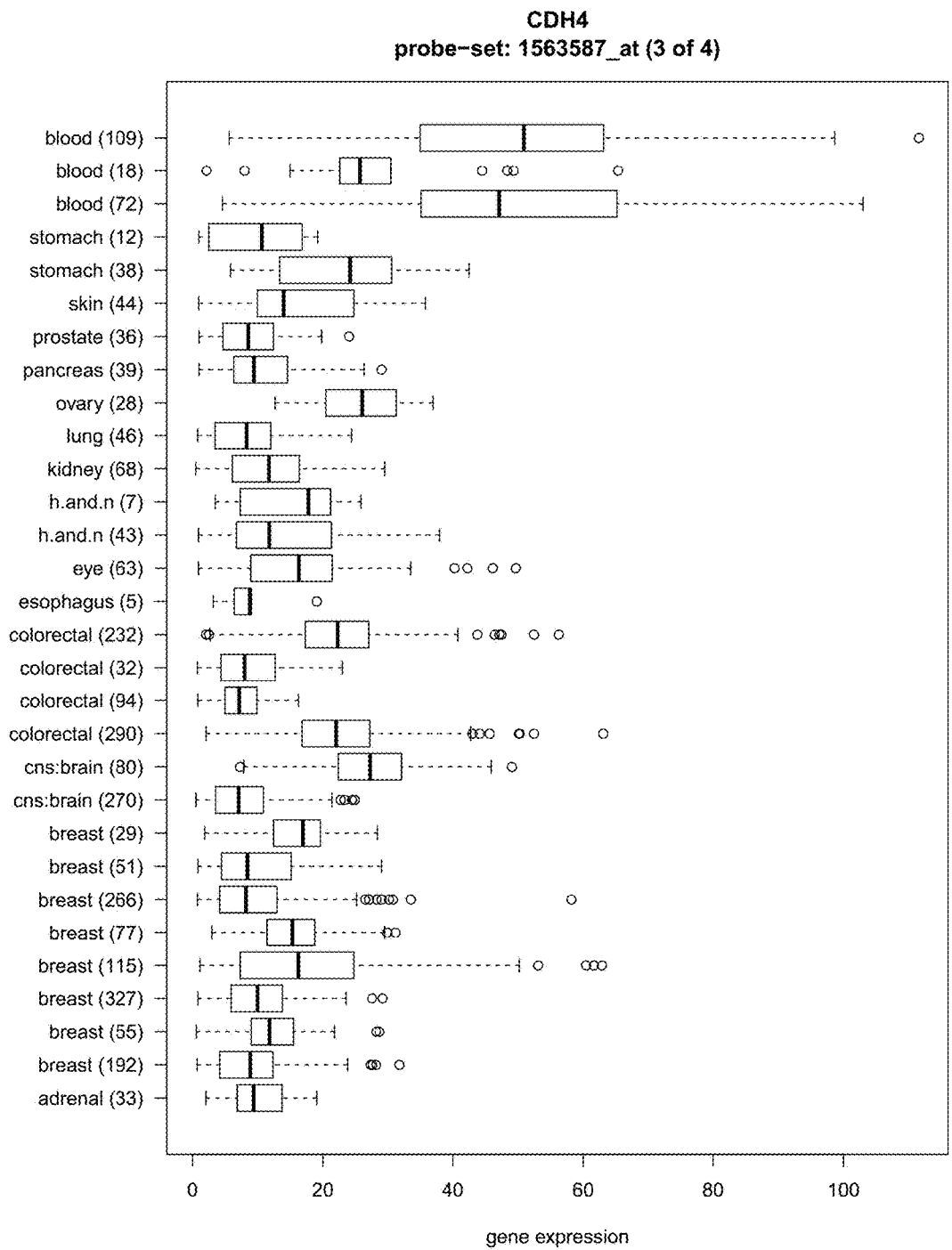
Figure 12:
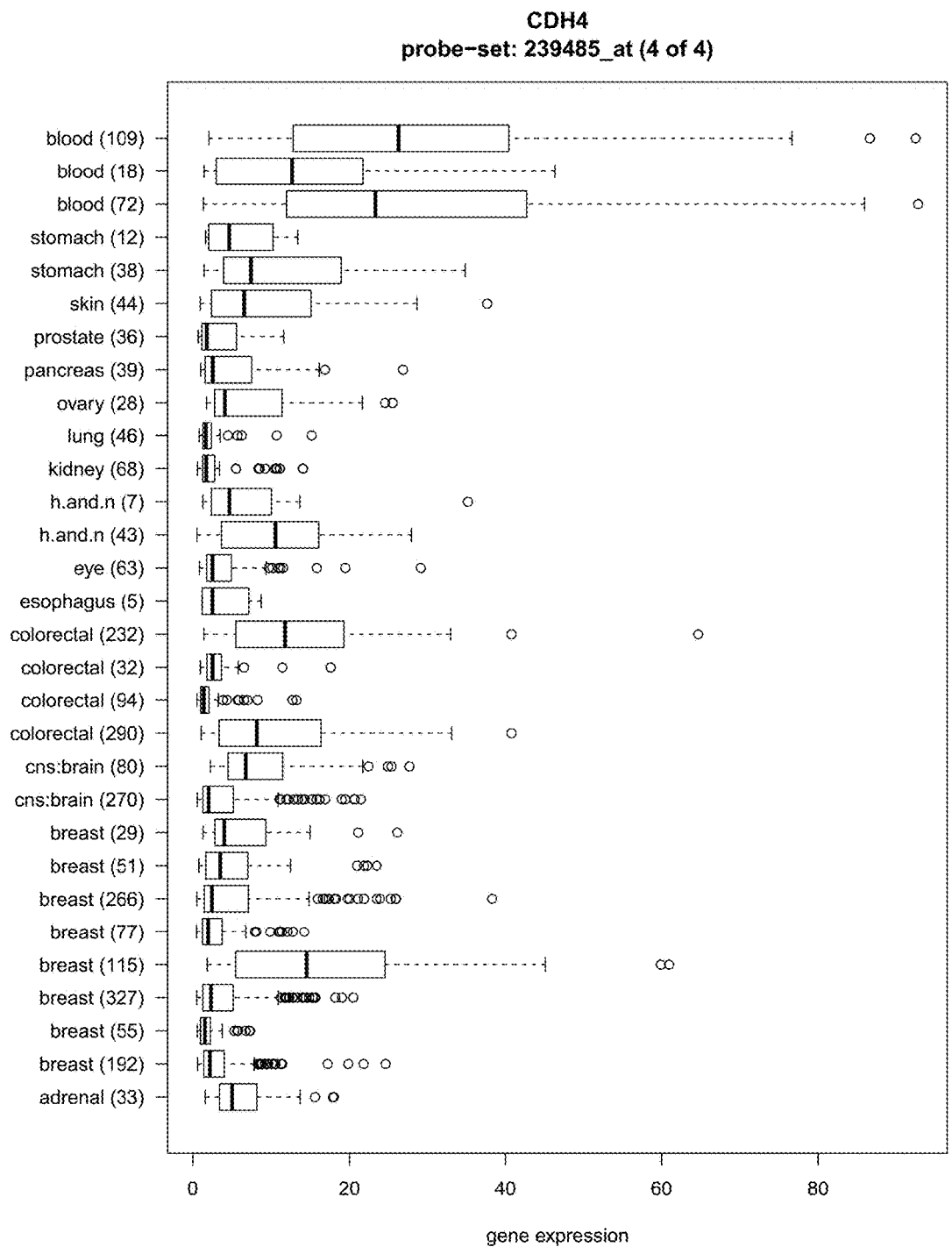
Figure 13:
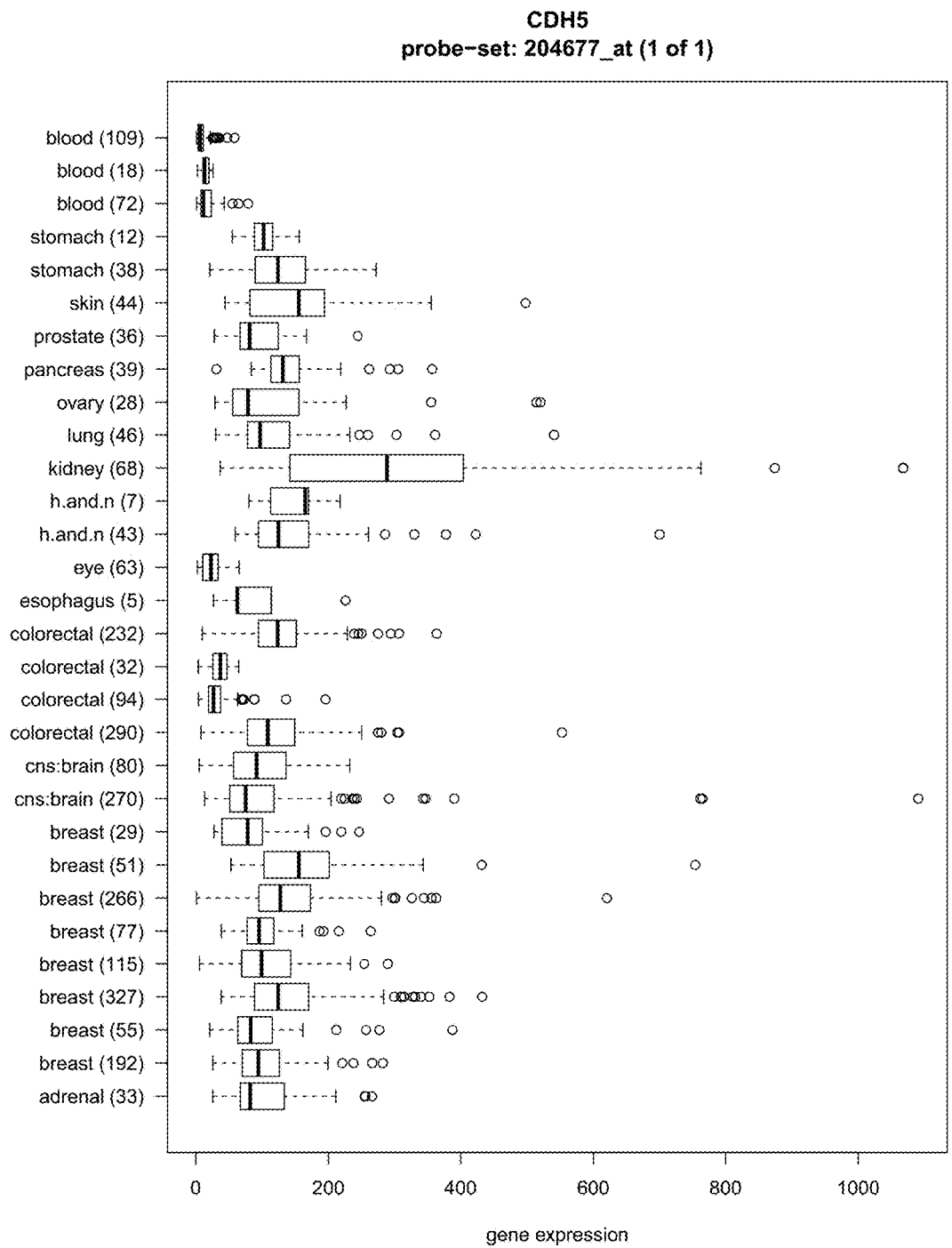
Figure 14:
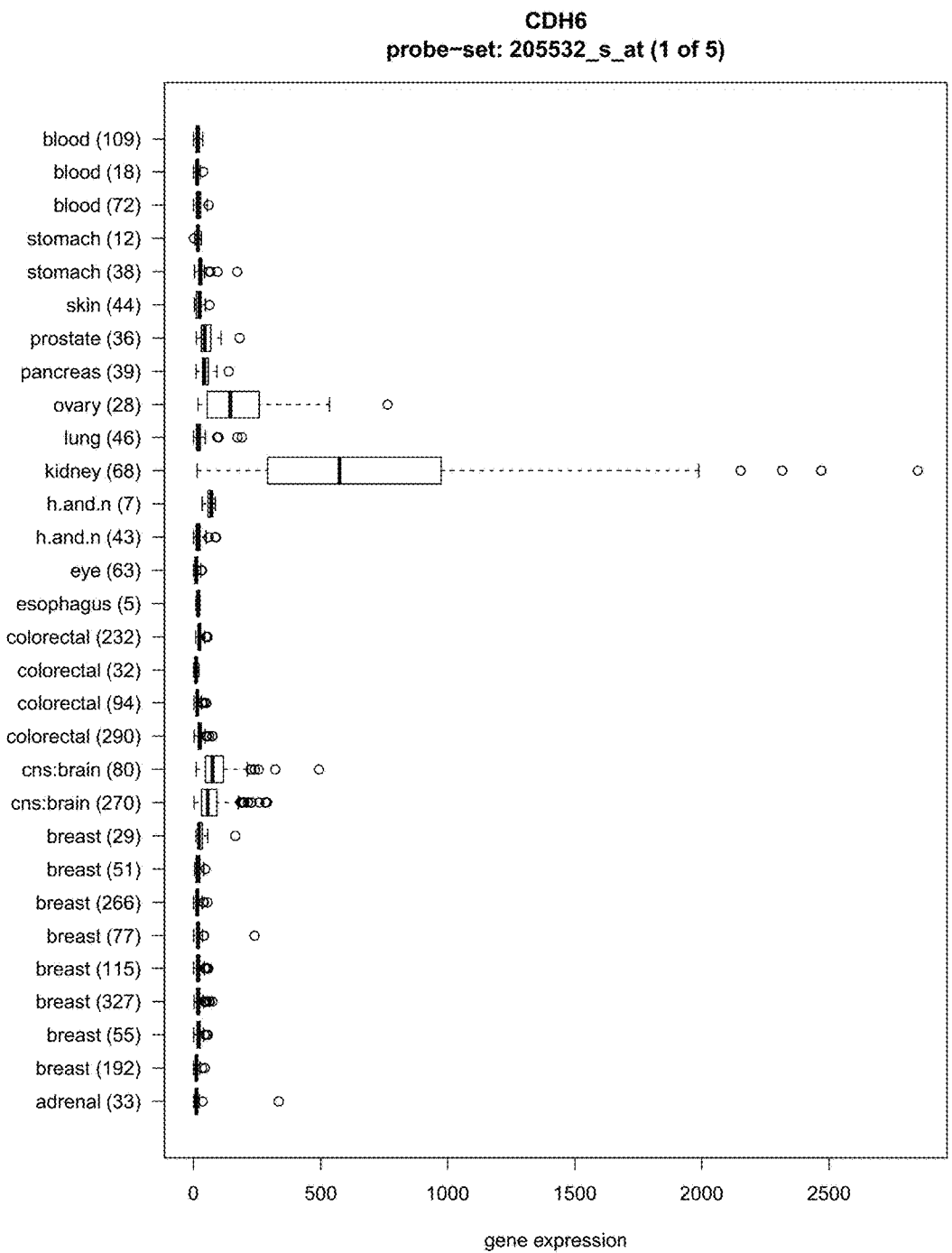
Figure 15:
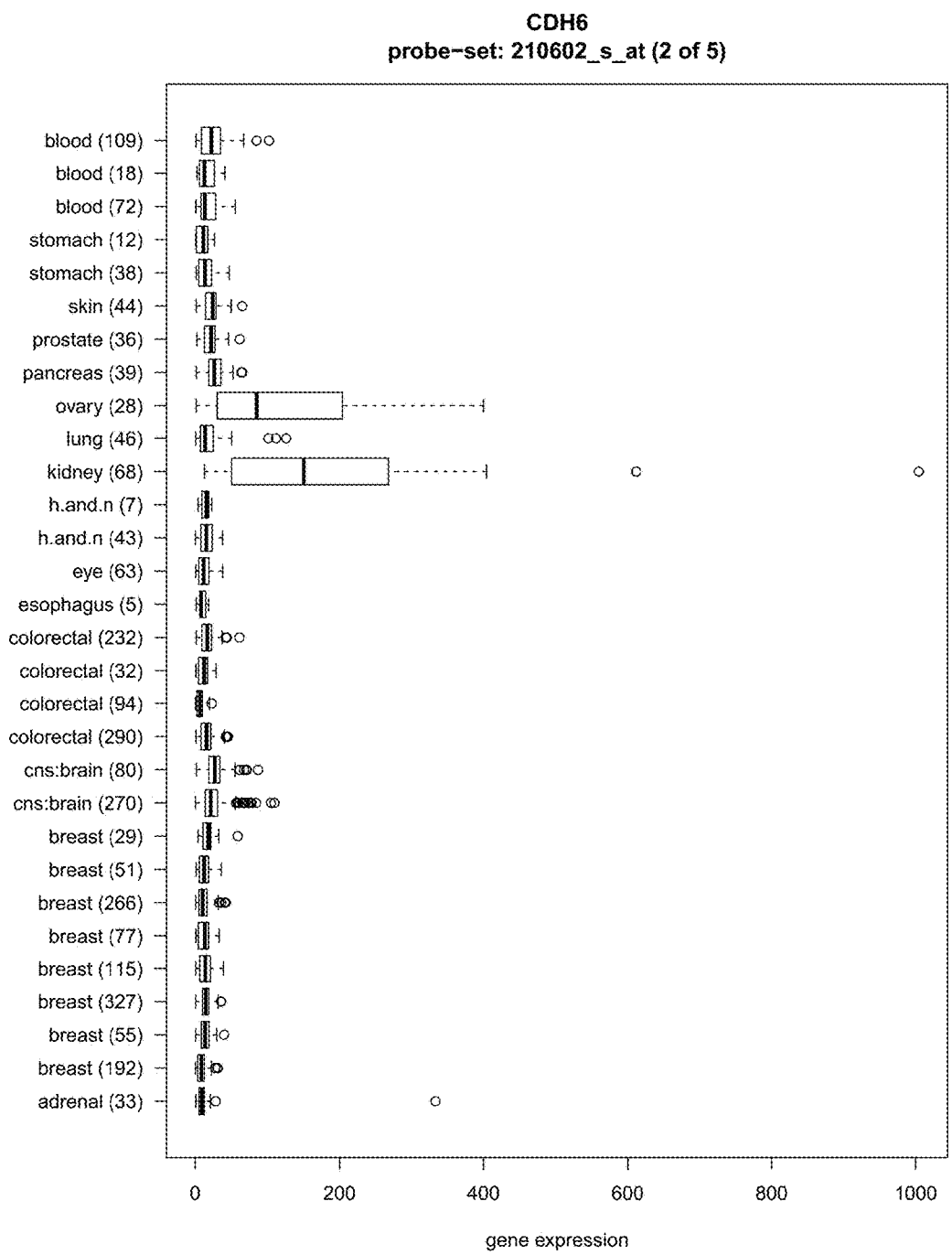
Figure 16:
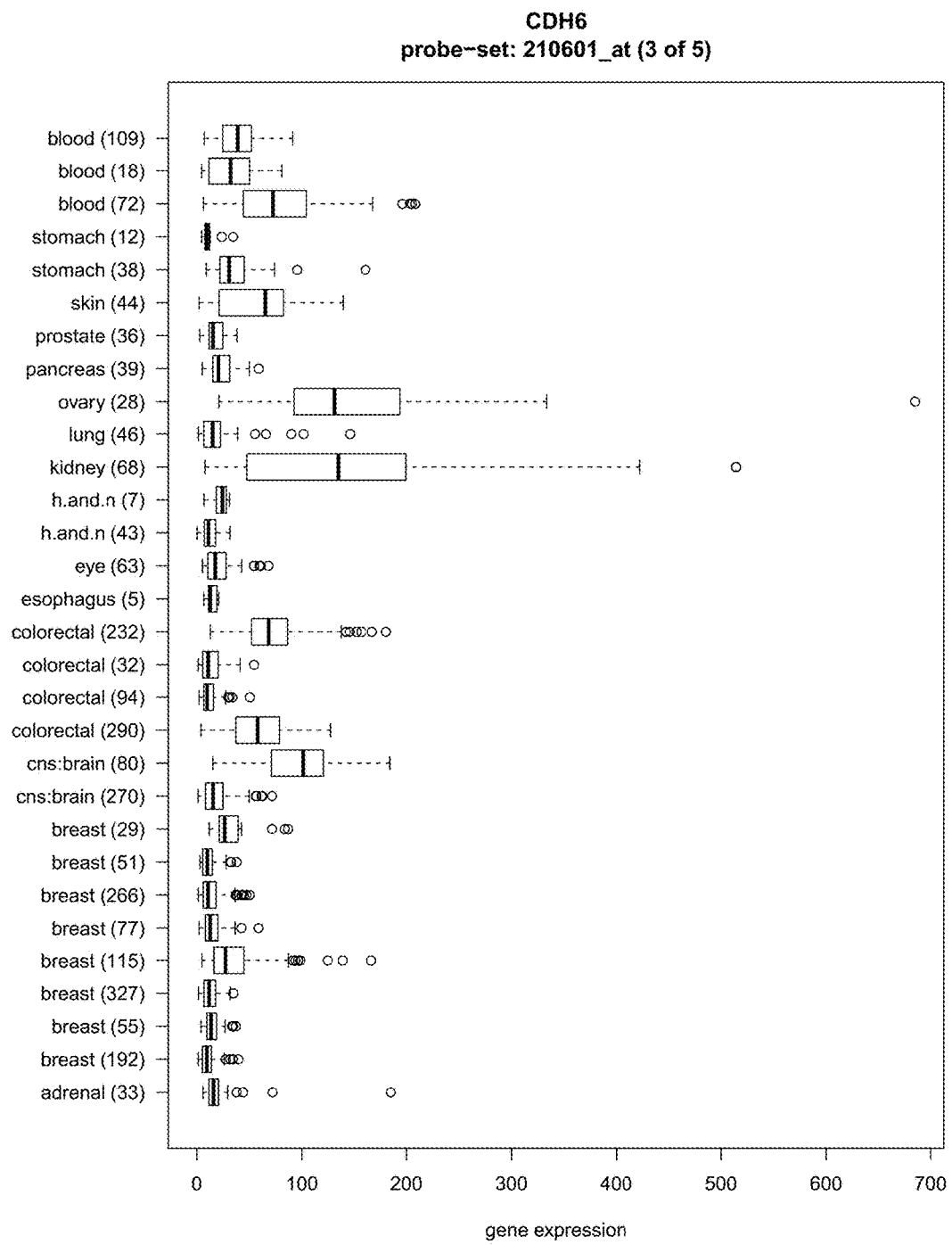
Figure 17:
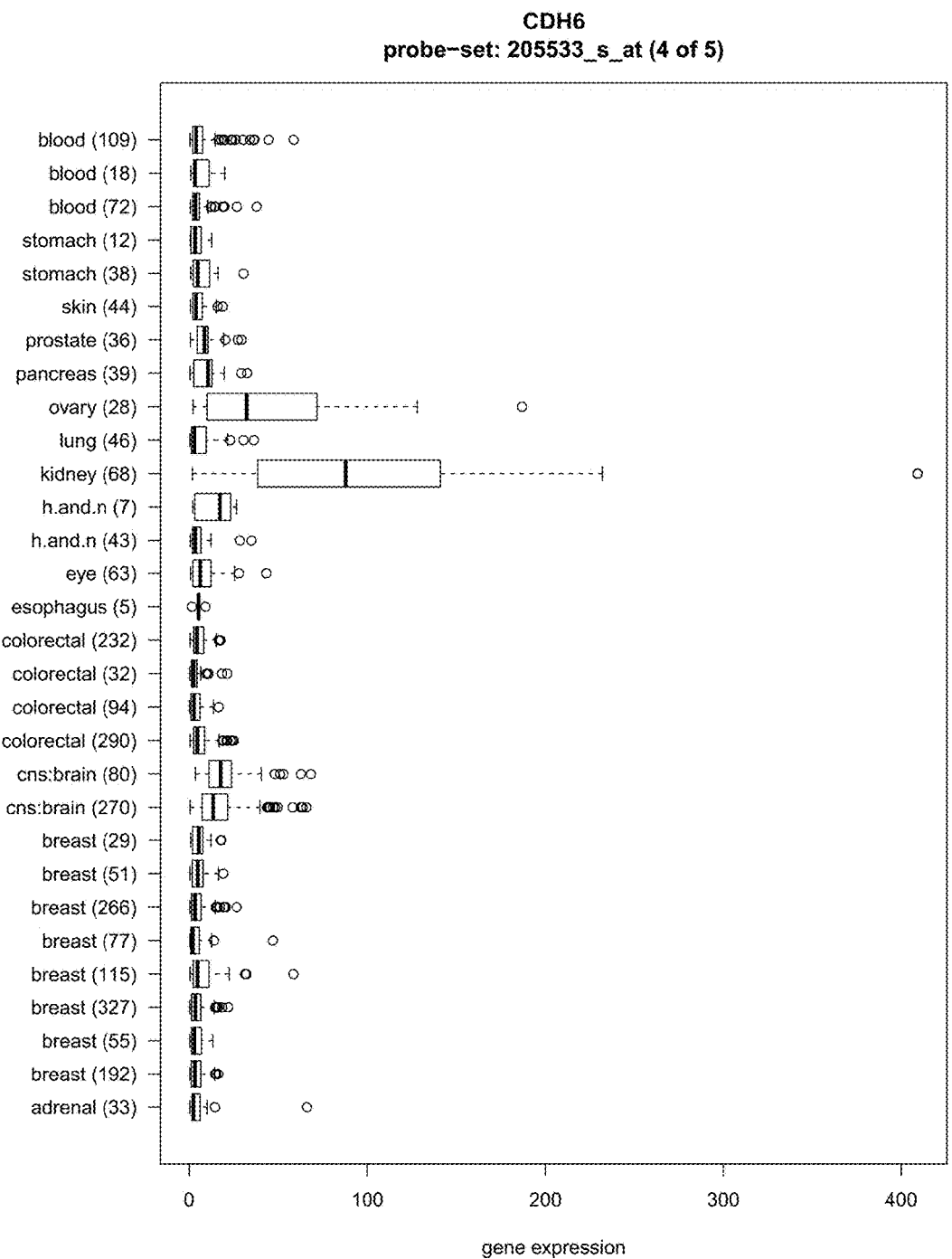
Figure 18:
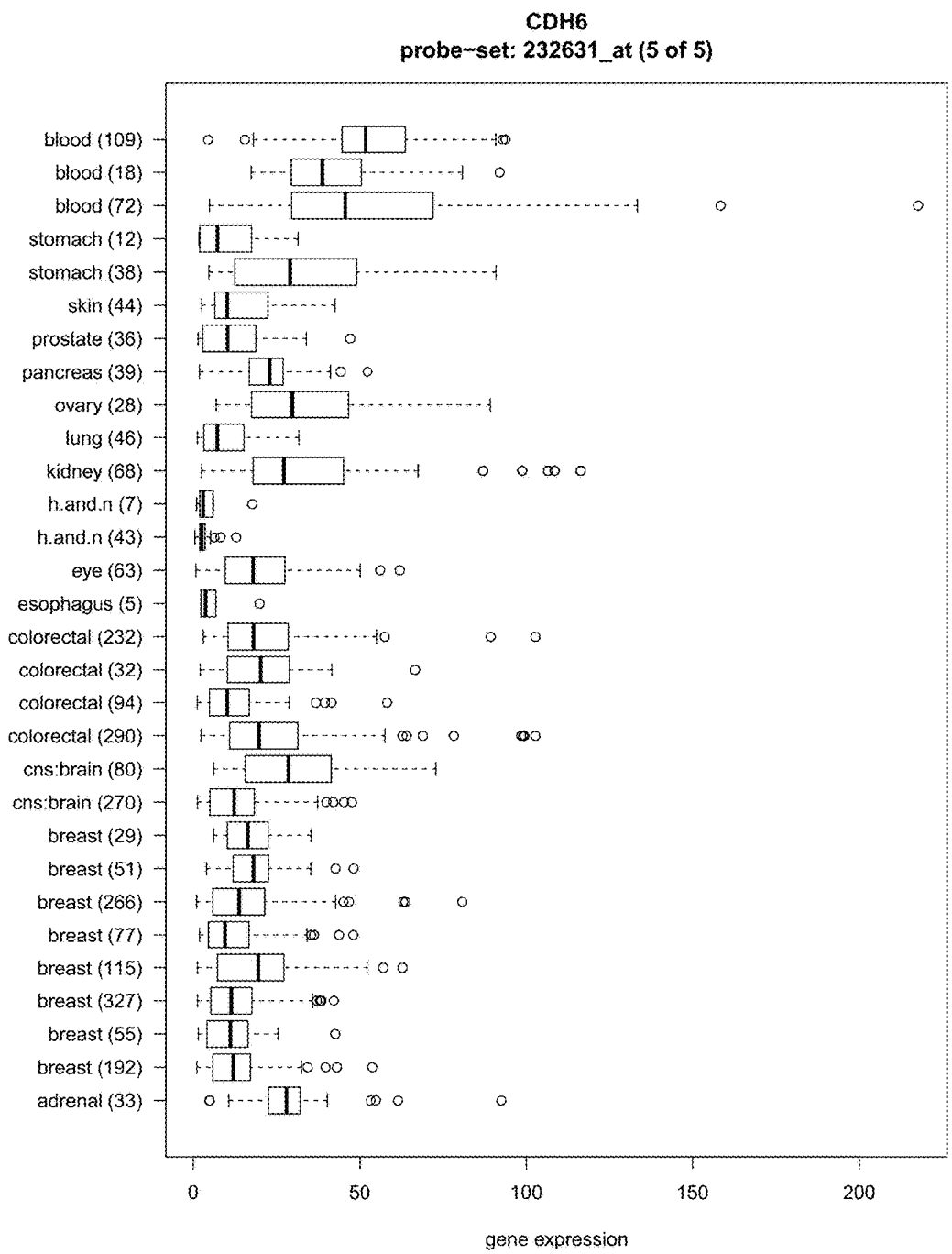
Figure 19:
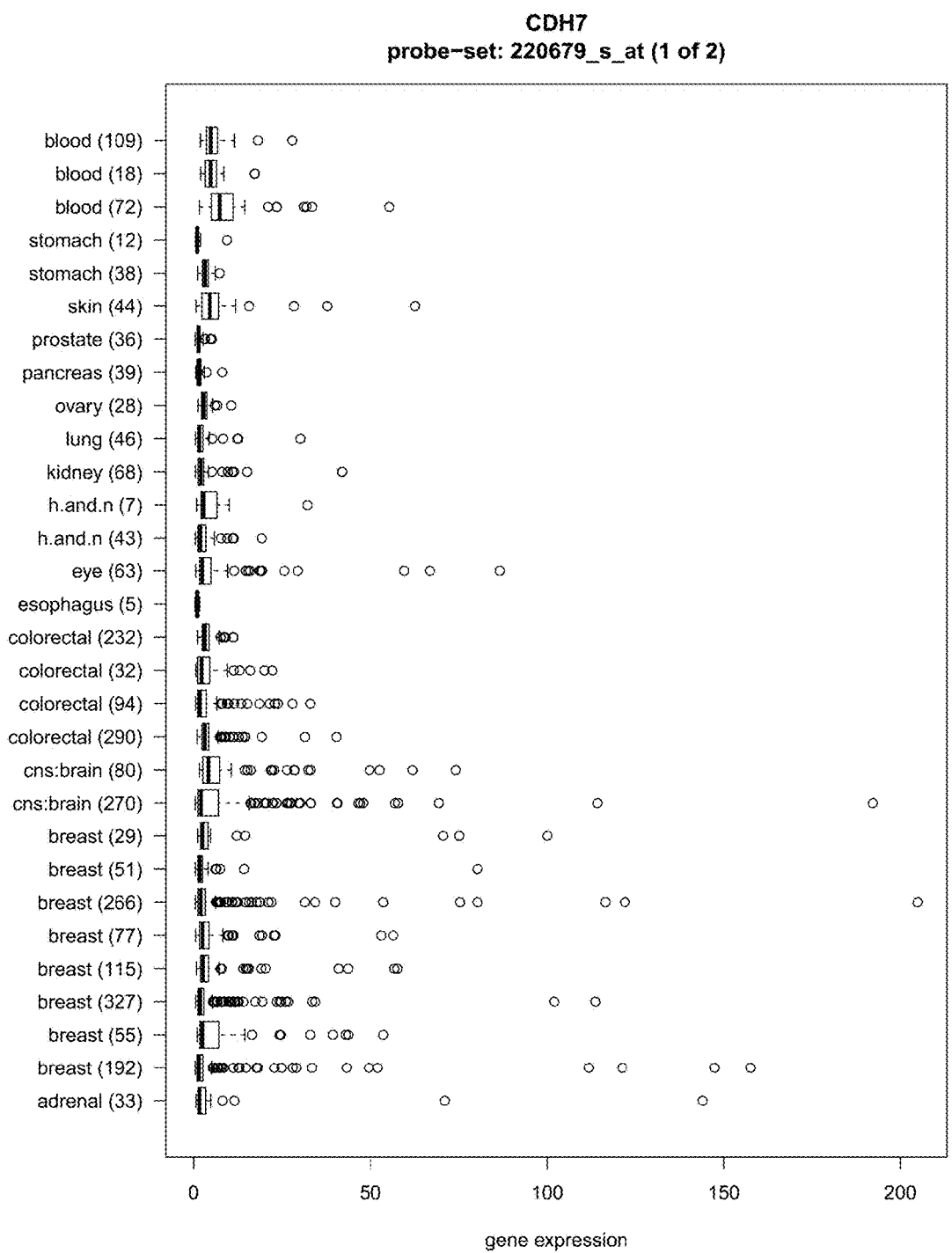
Figure 20:
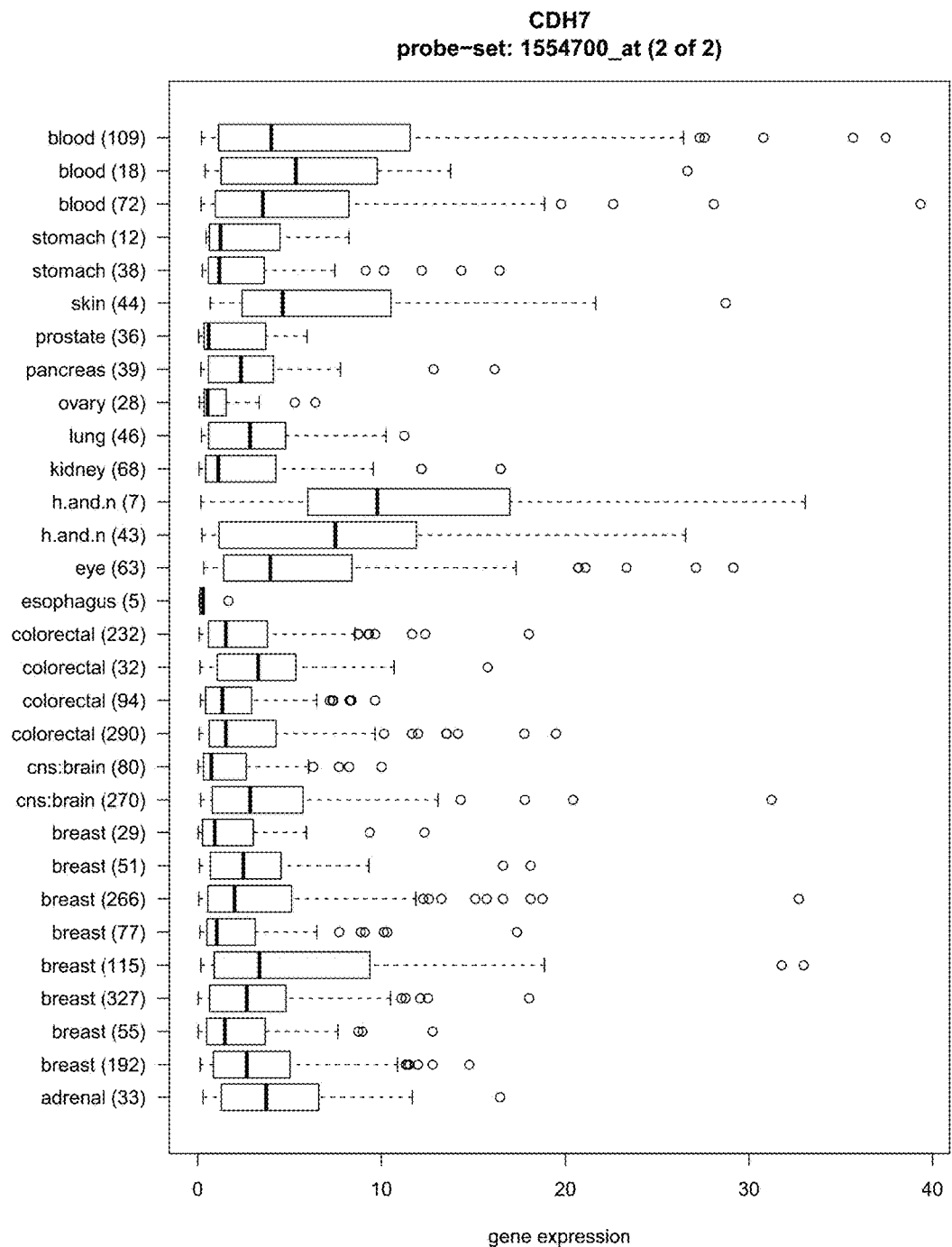
Figure 21:
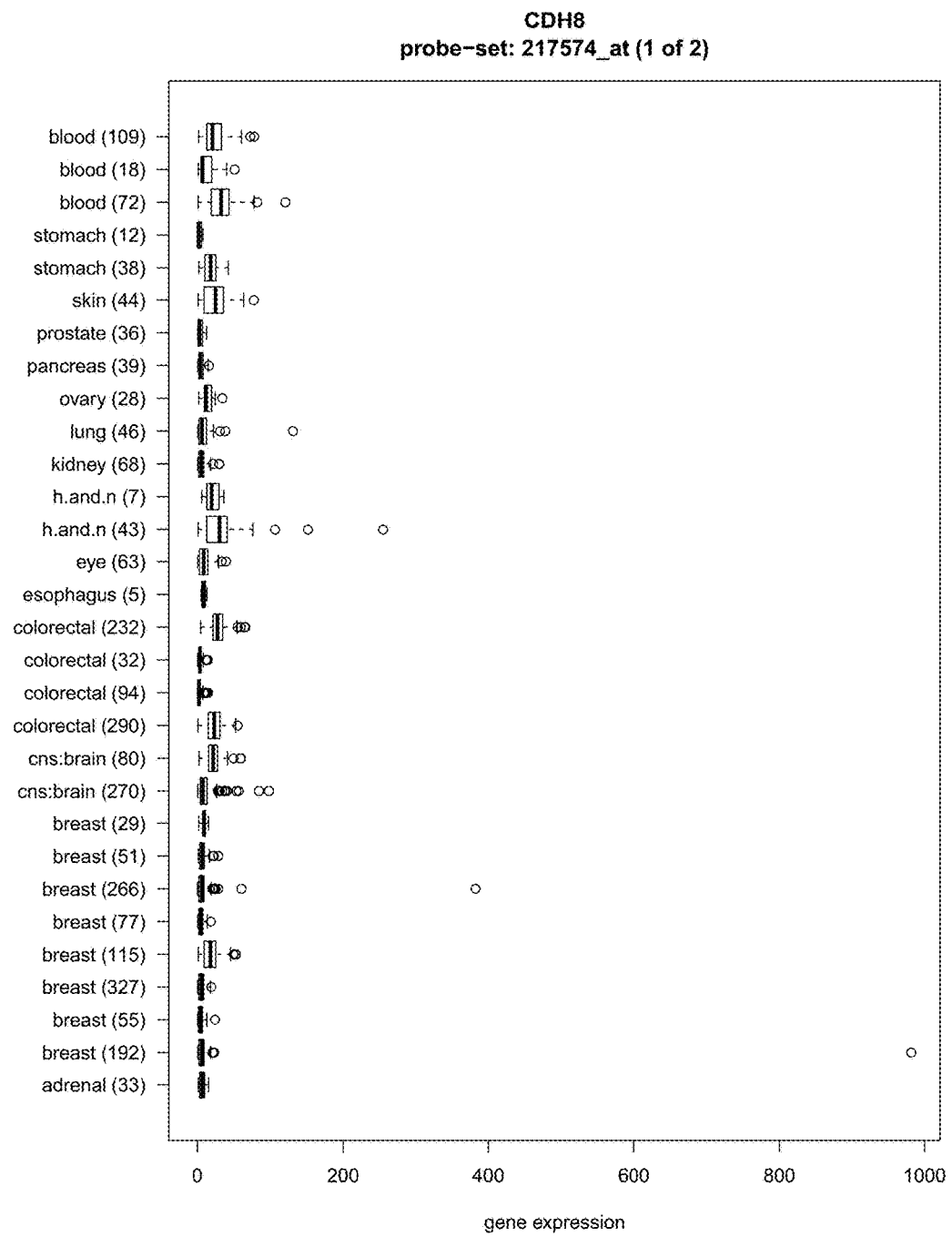
Figure 22:
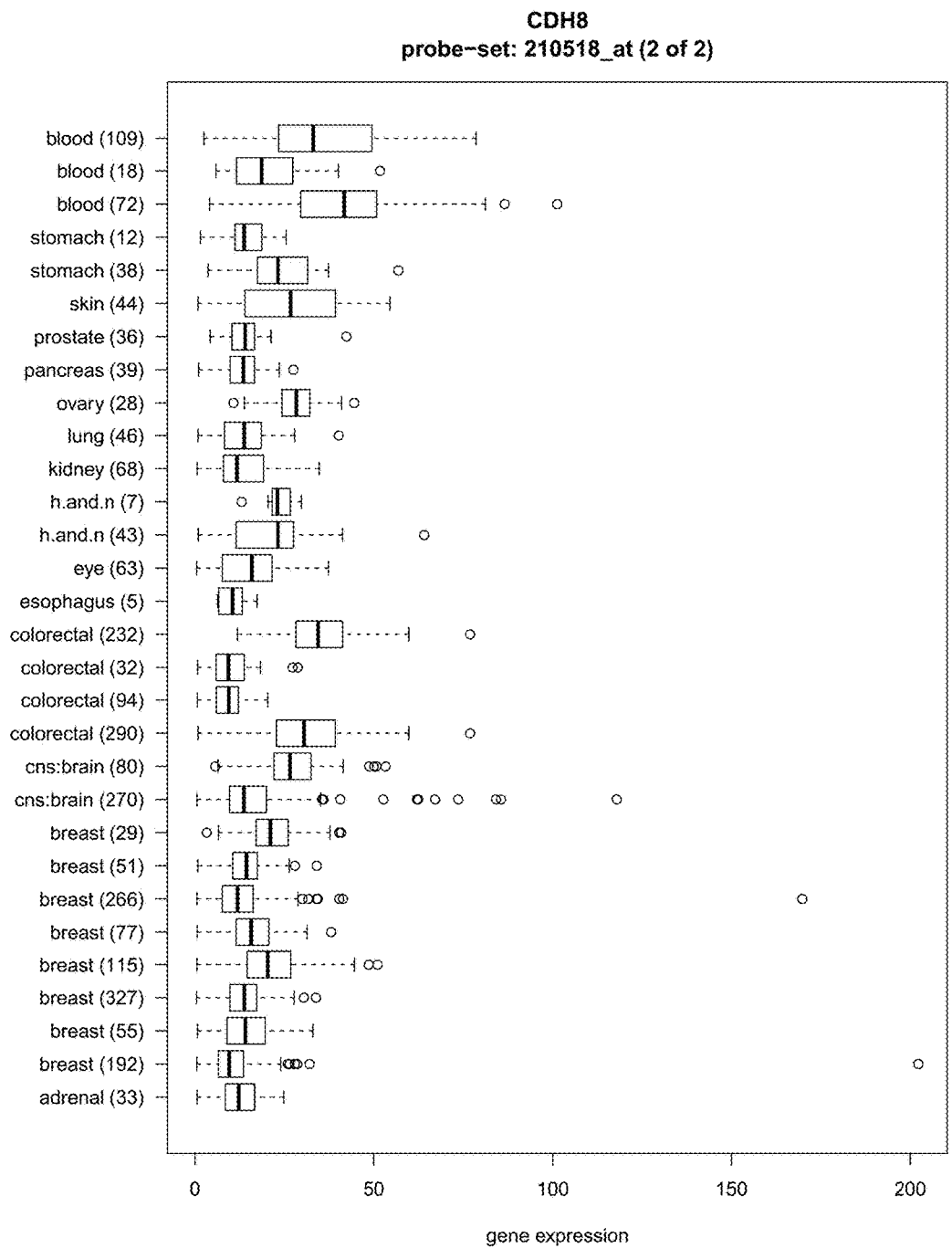
Figure 23:
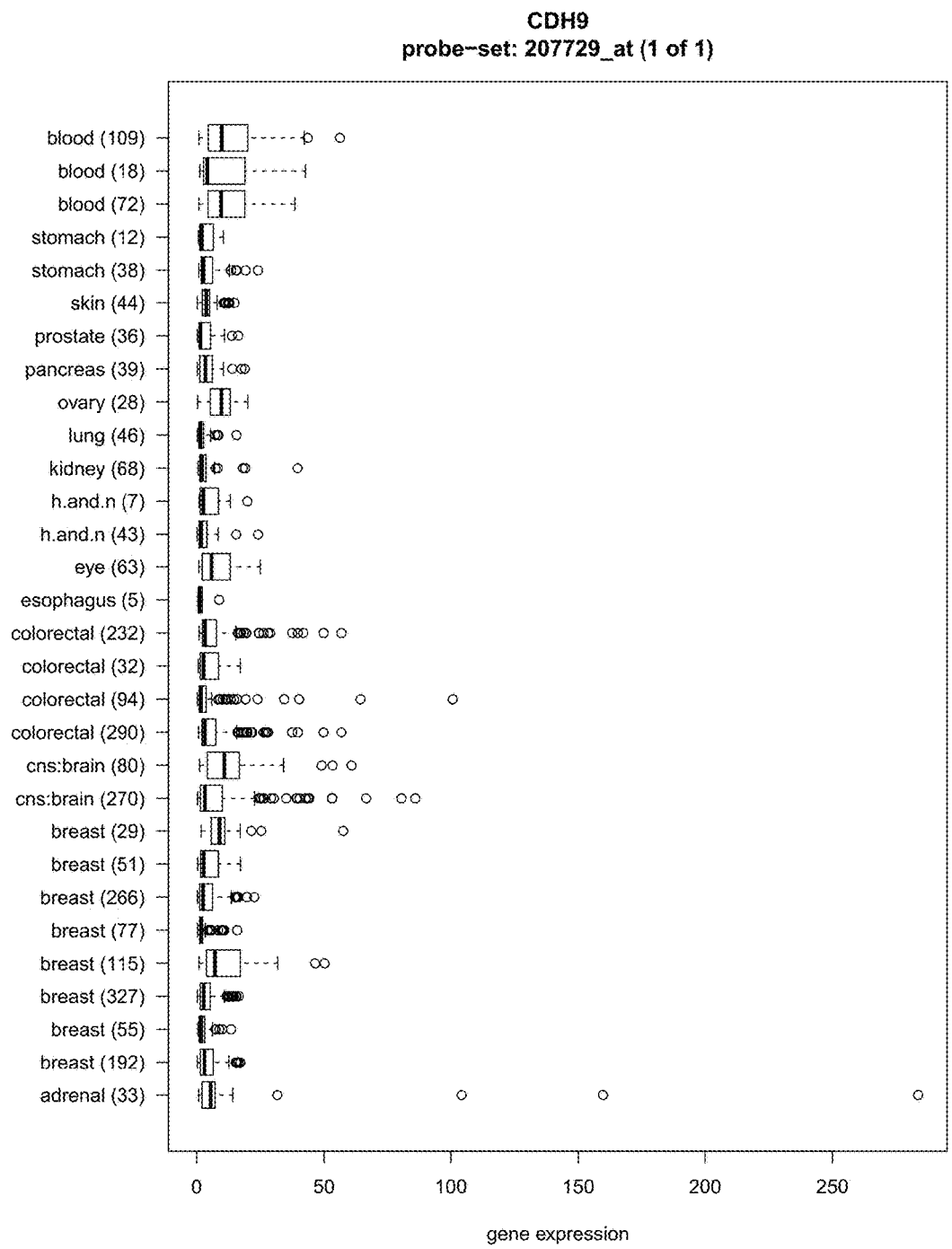
Figure 24:
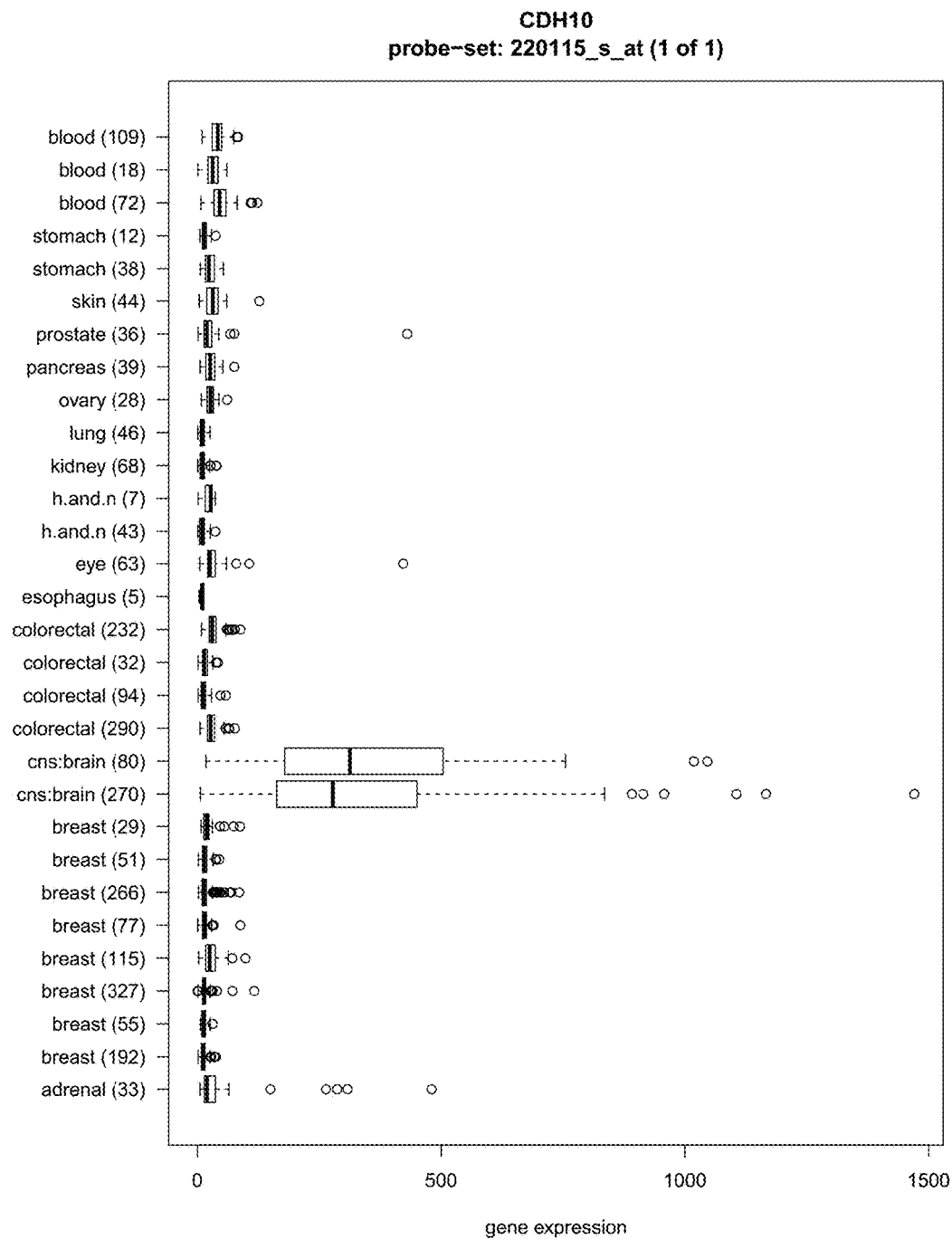
Figure 25:
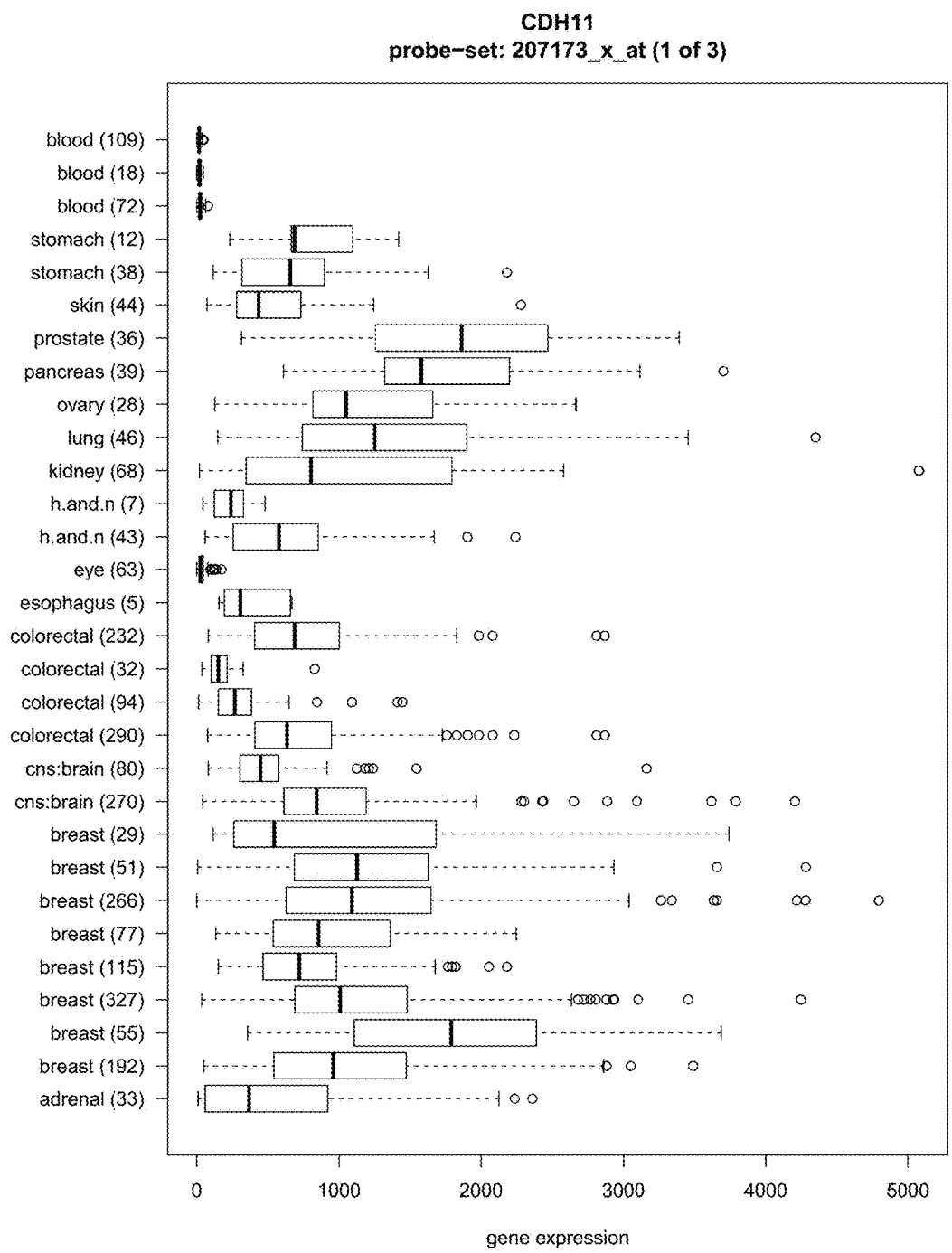
Figure 26:
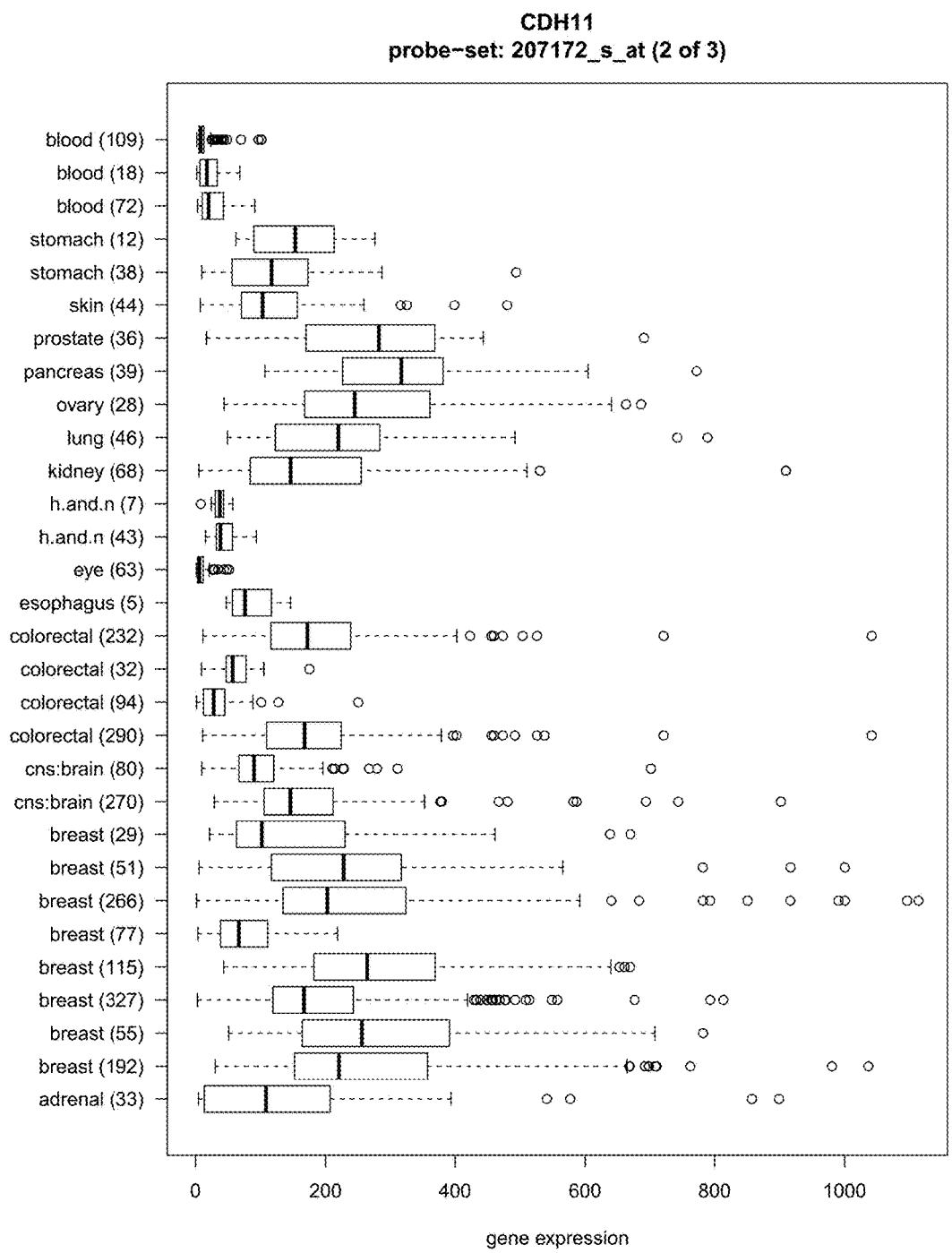
Figure 27:
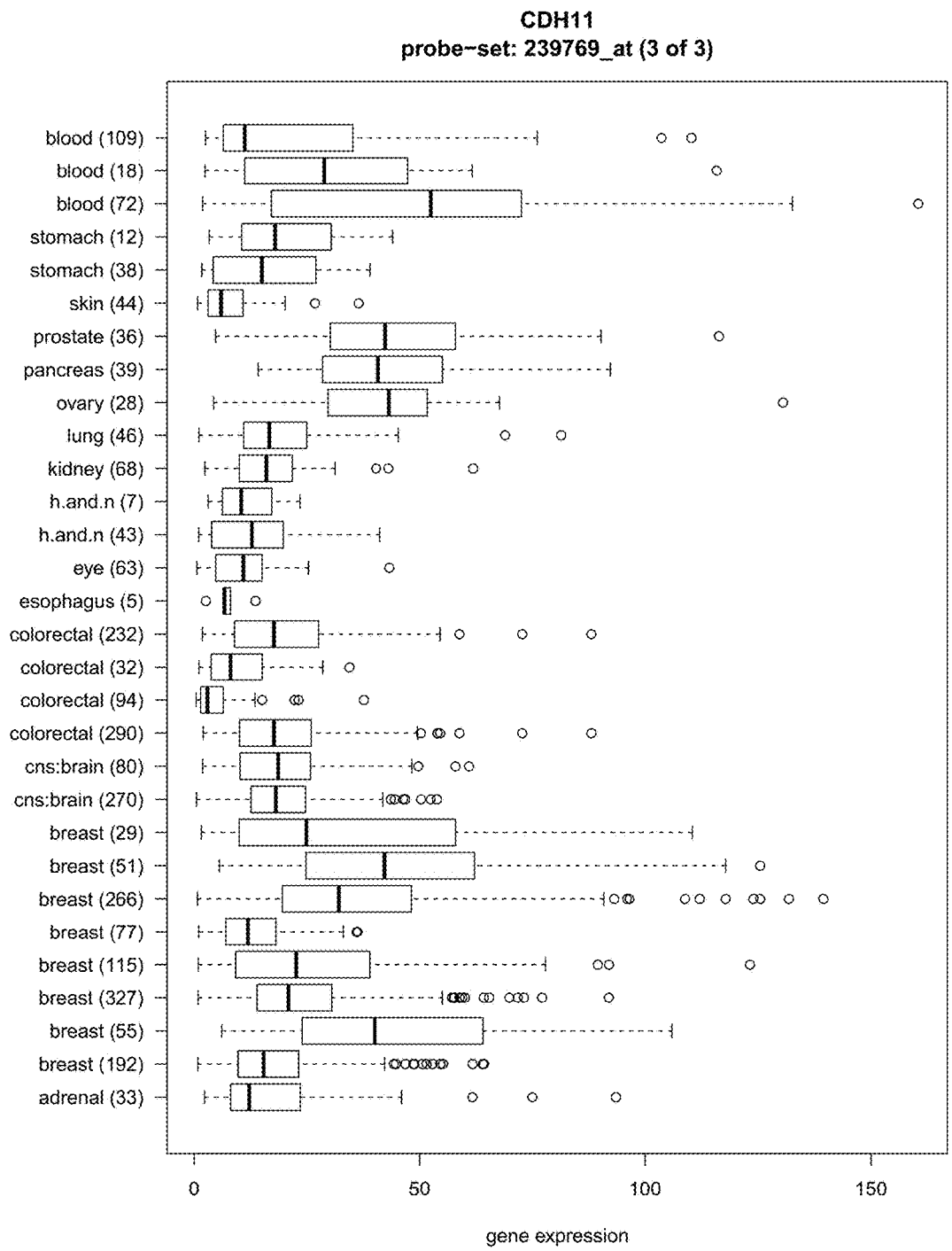
Figure 28:
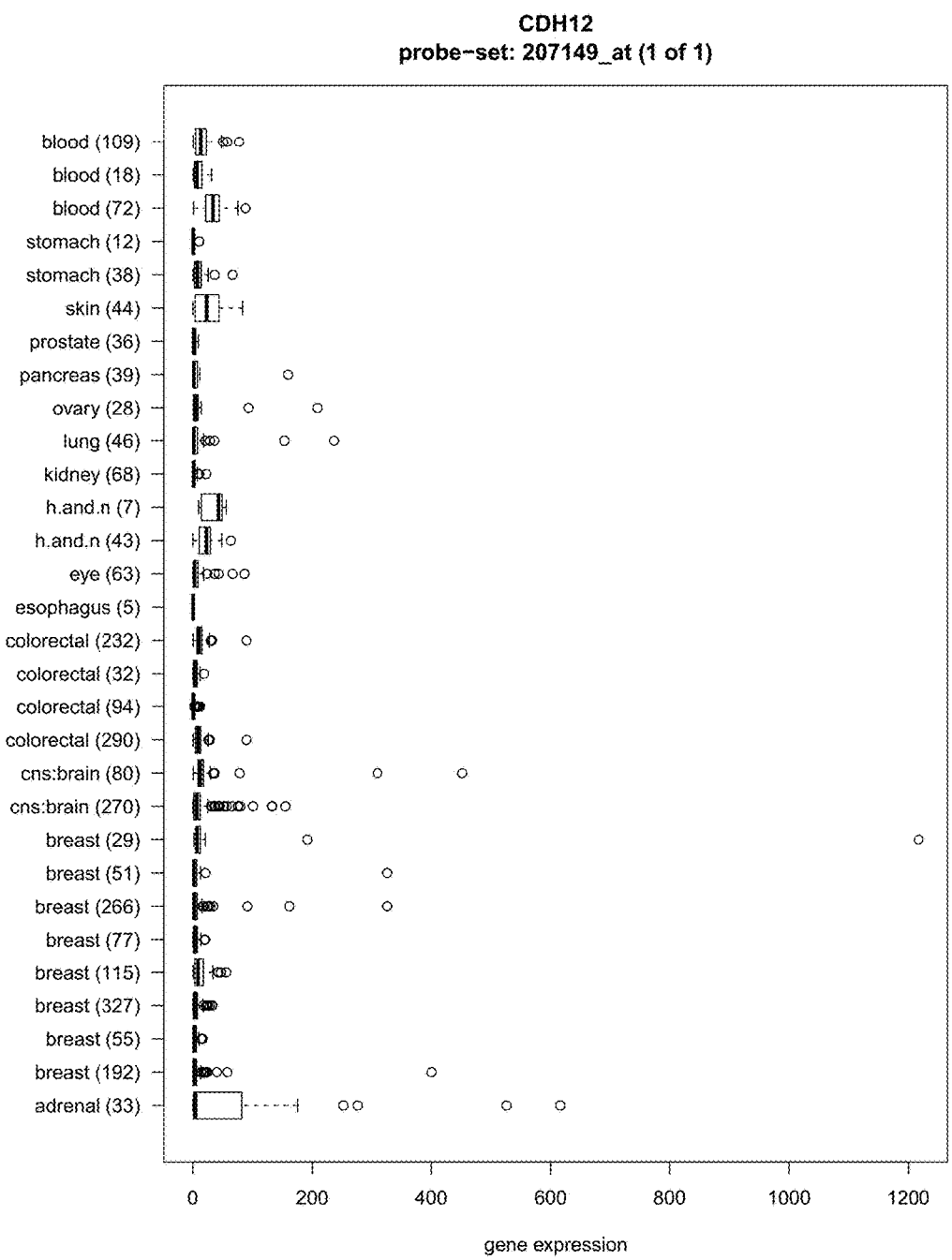
Figure 29:
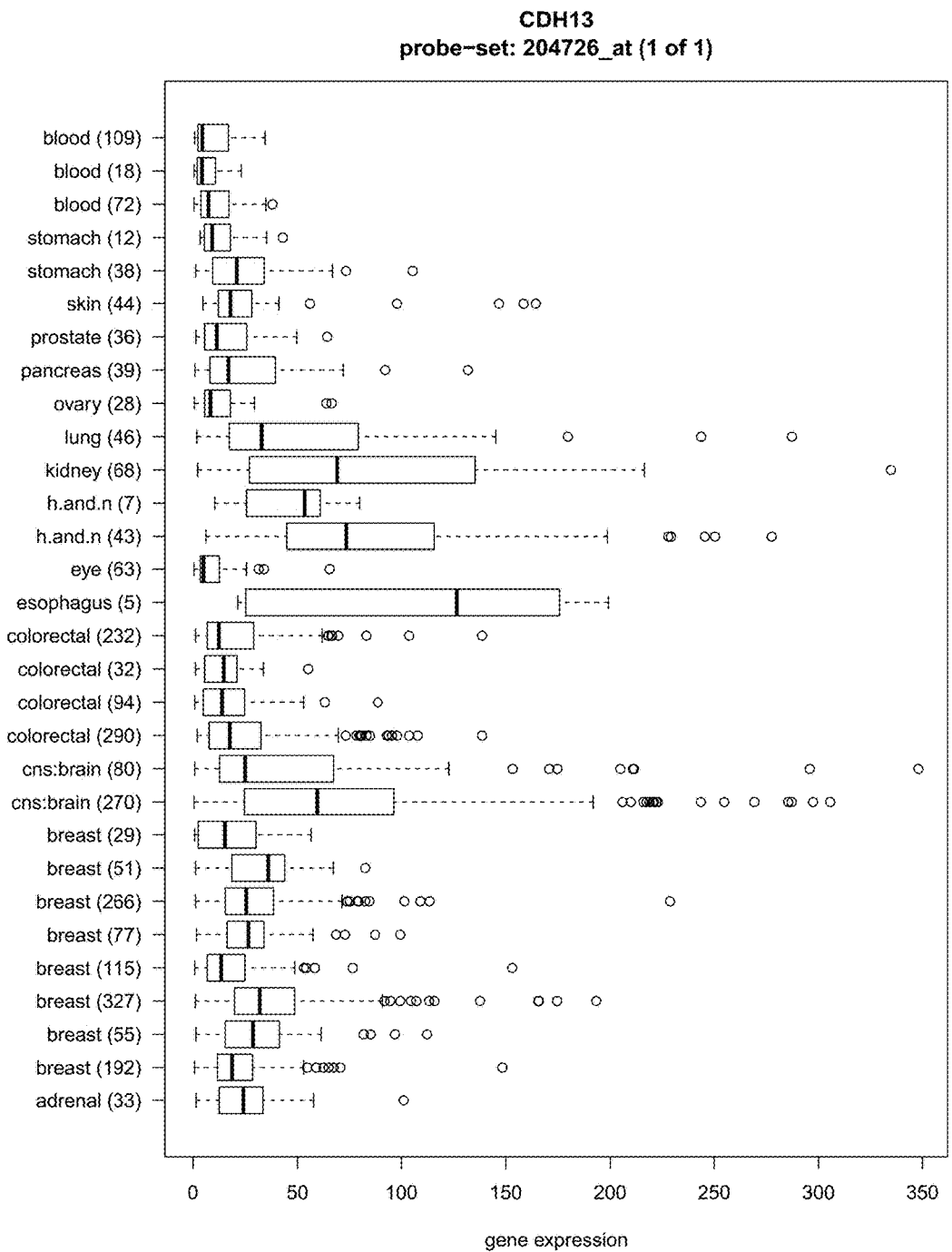
Figure 30:
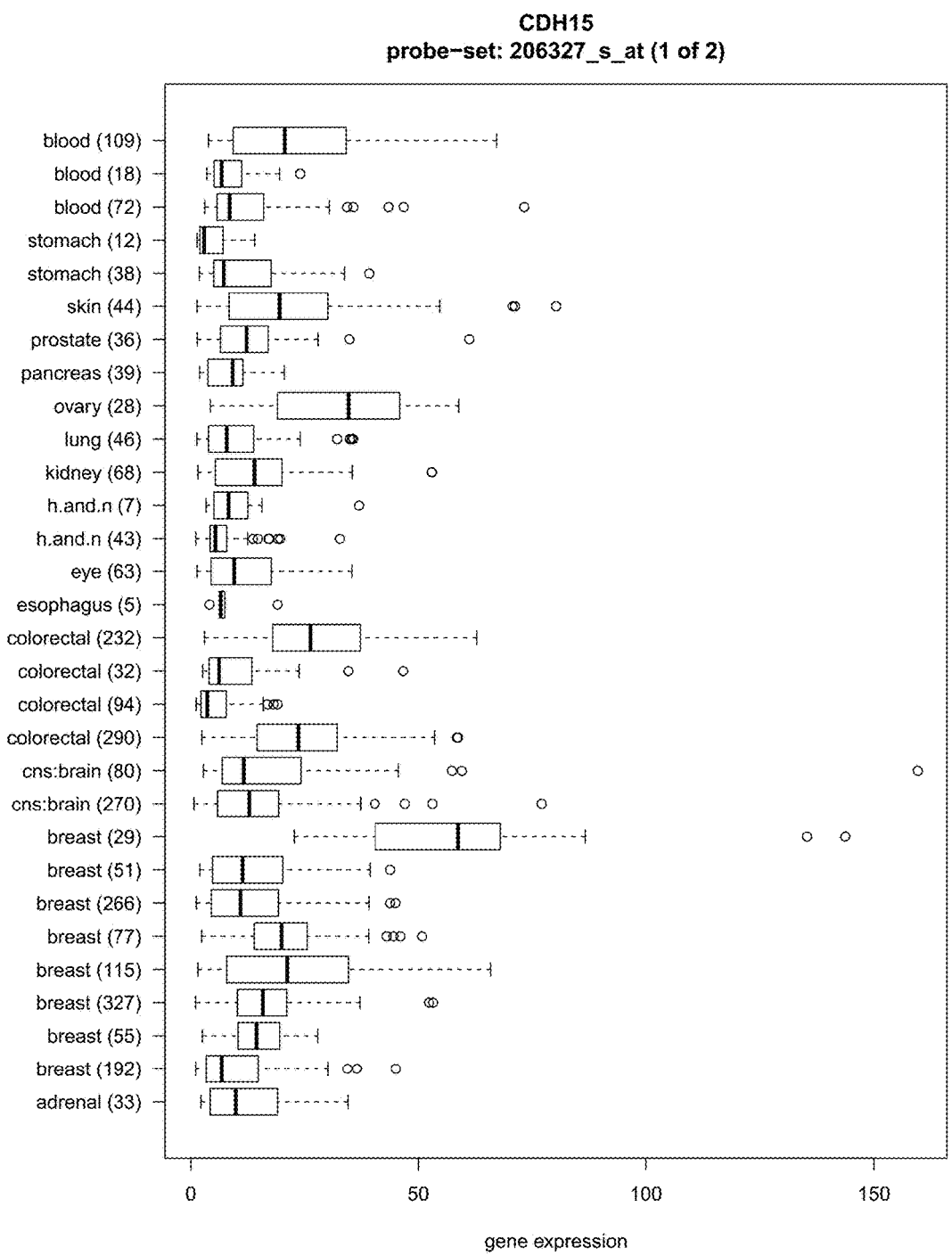
Figure 31:
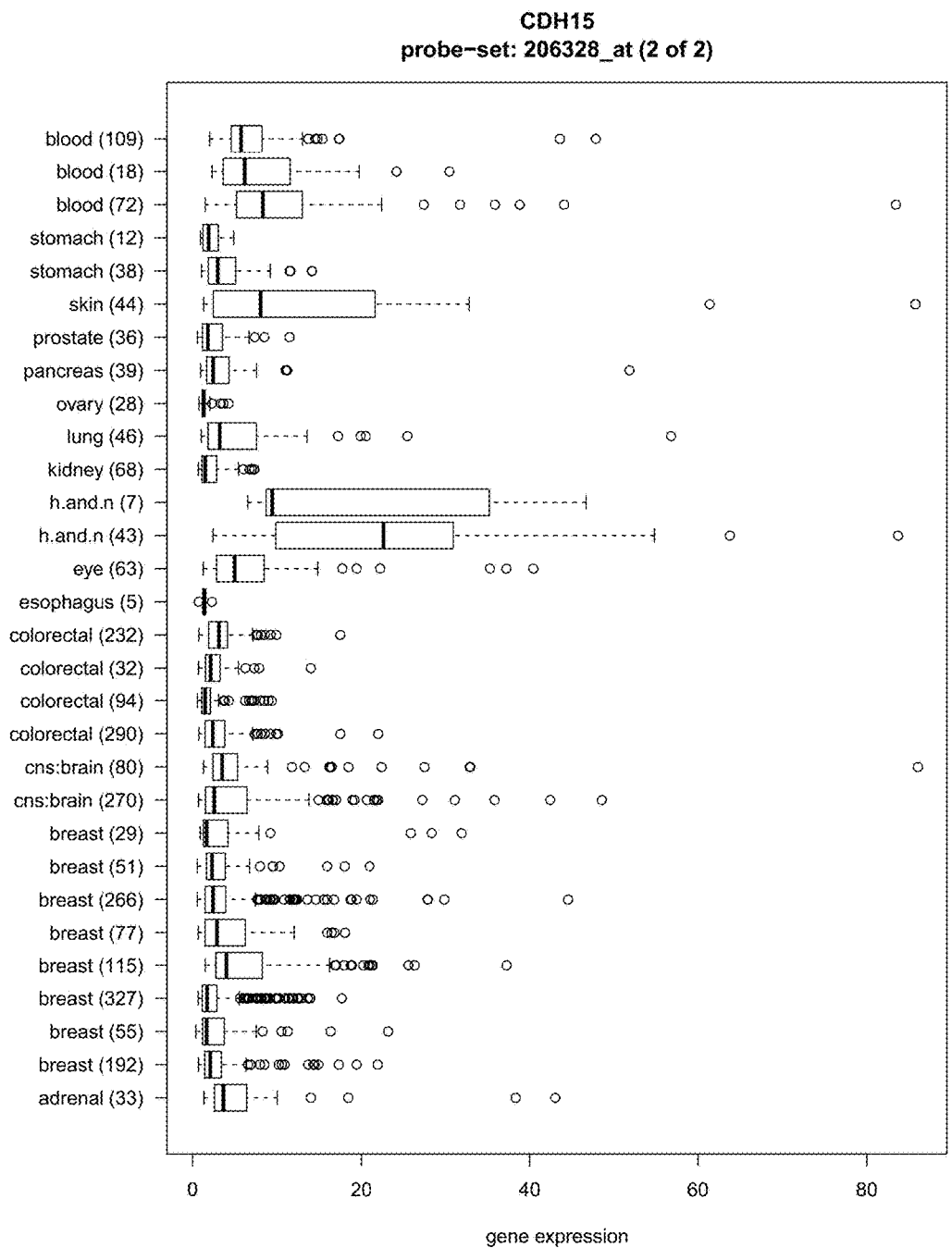
Figure 32:
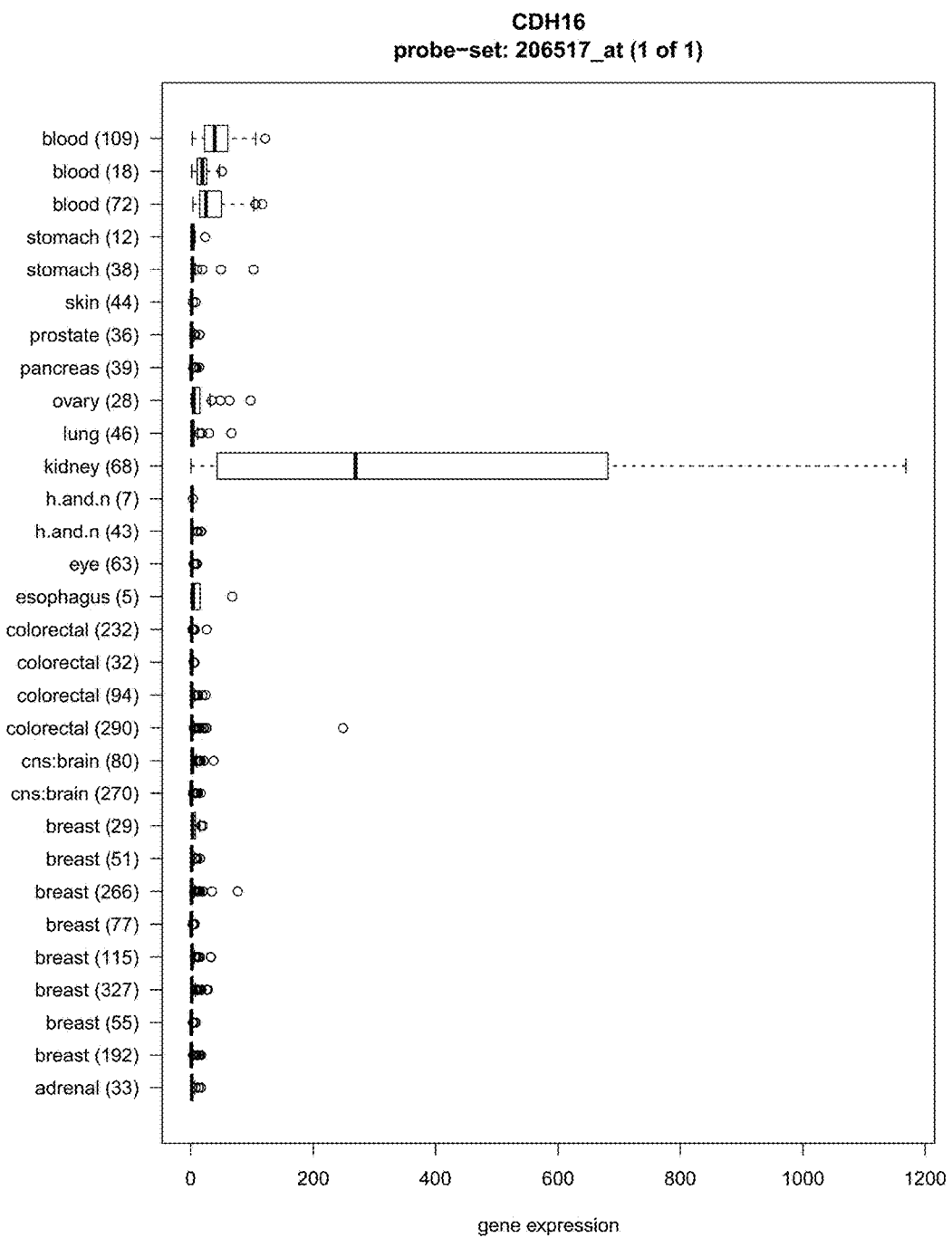
Figure 33:
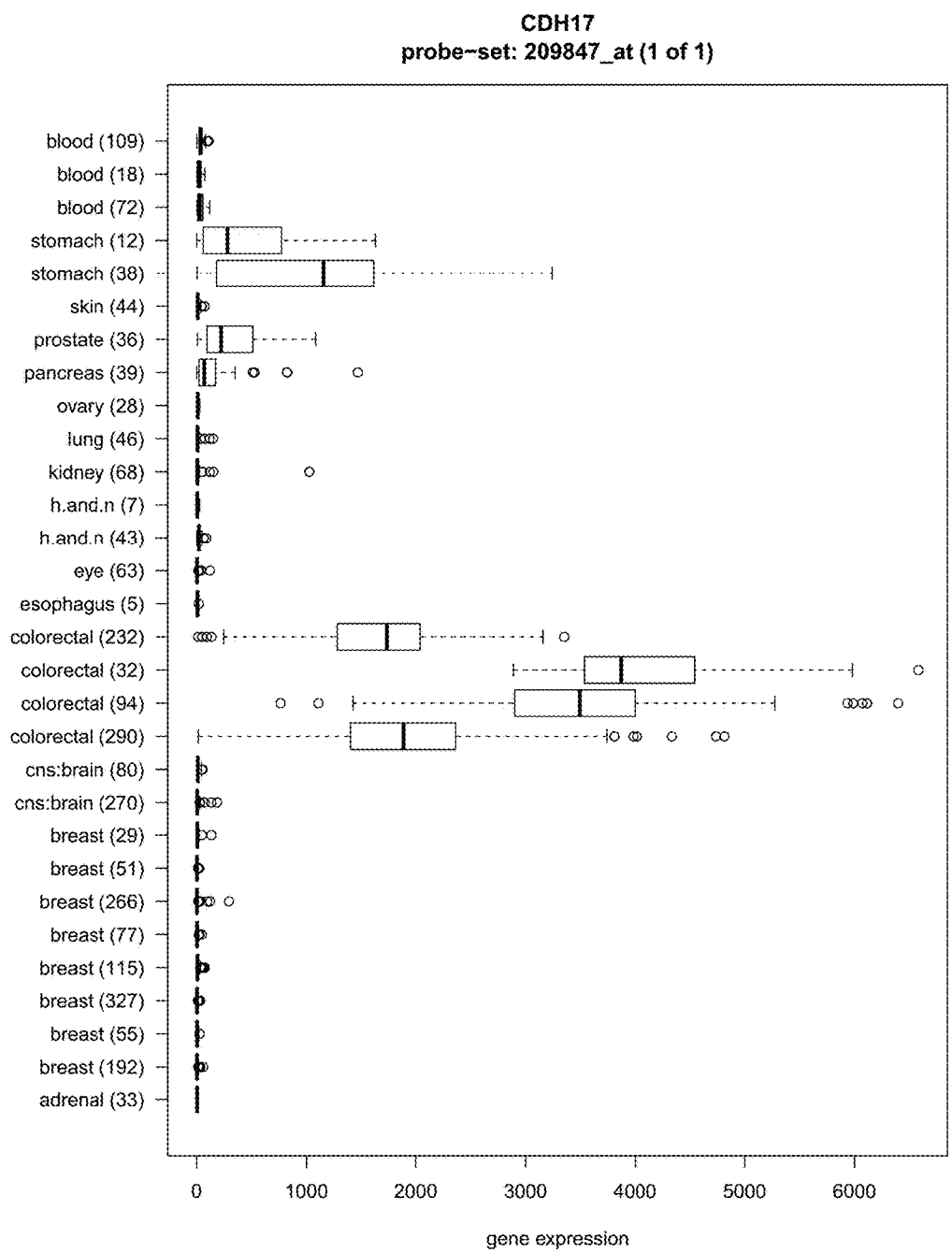
Figure 34:
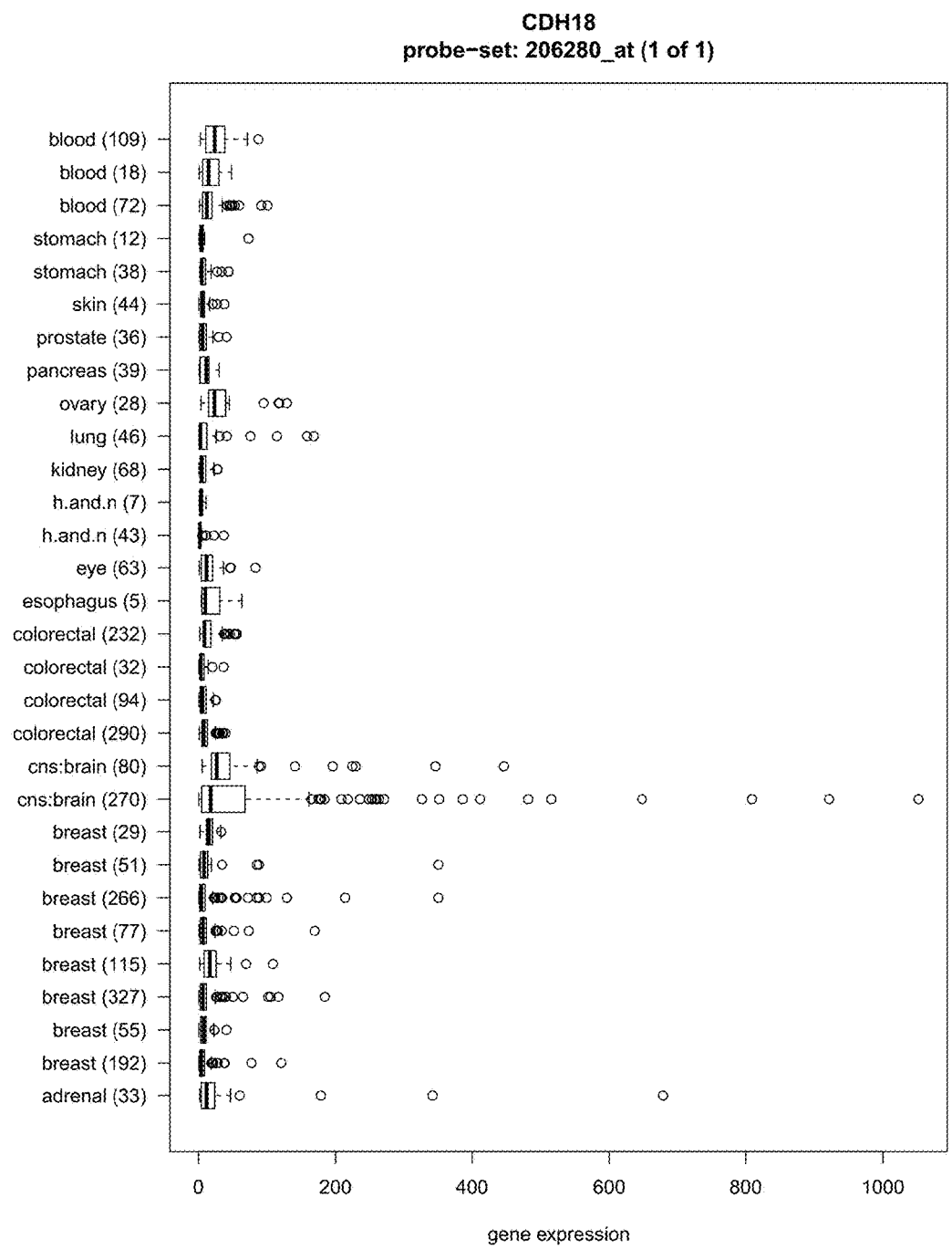
Figure 35:
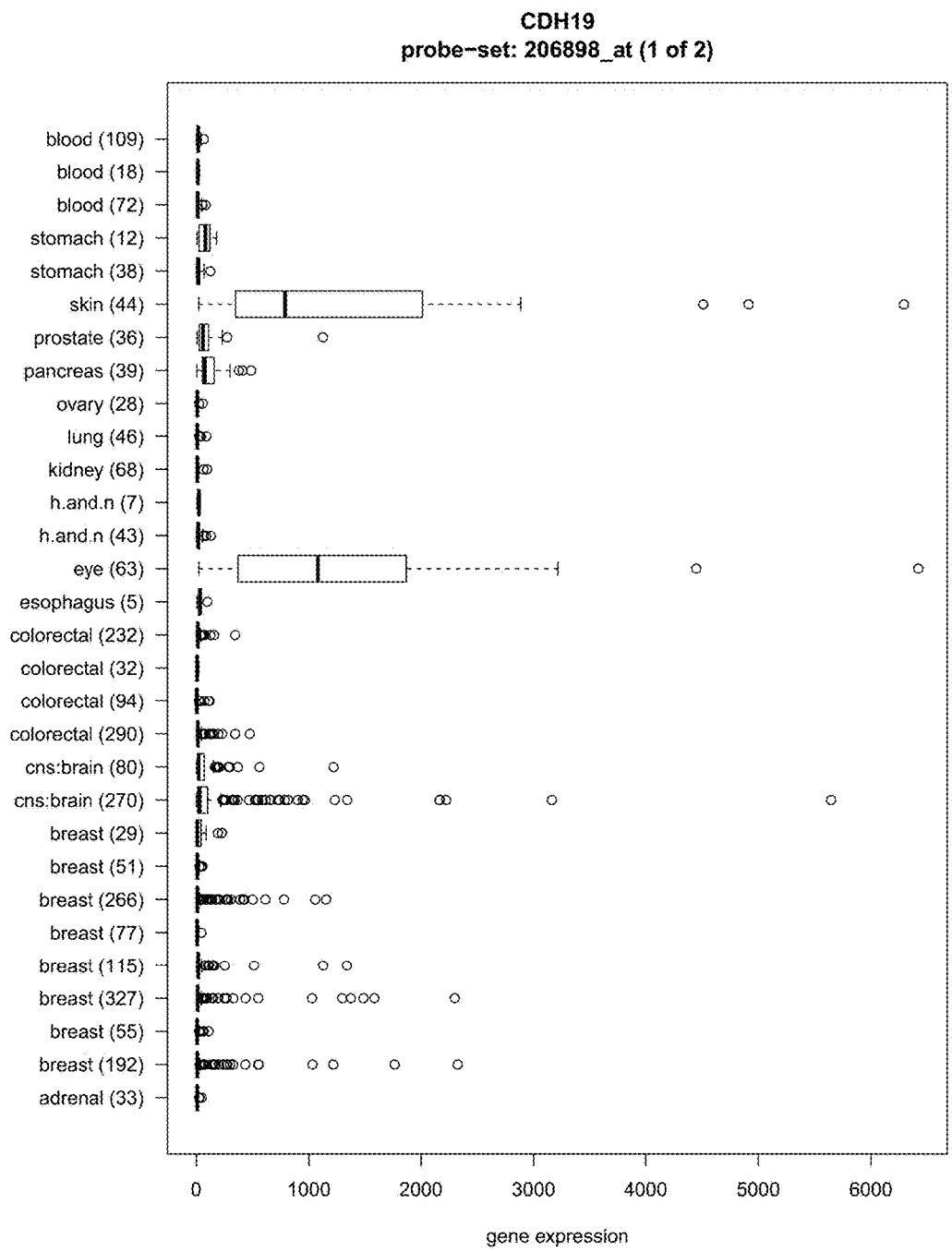
Figure 36:
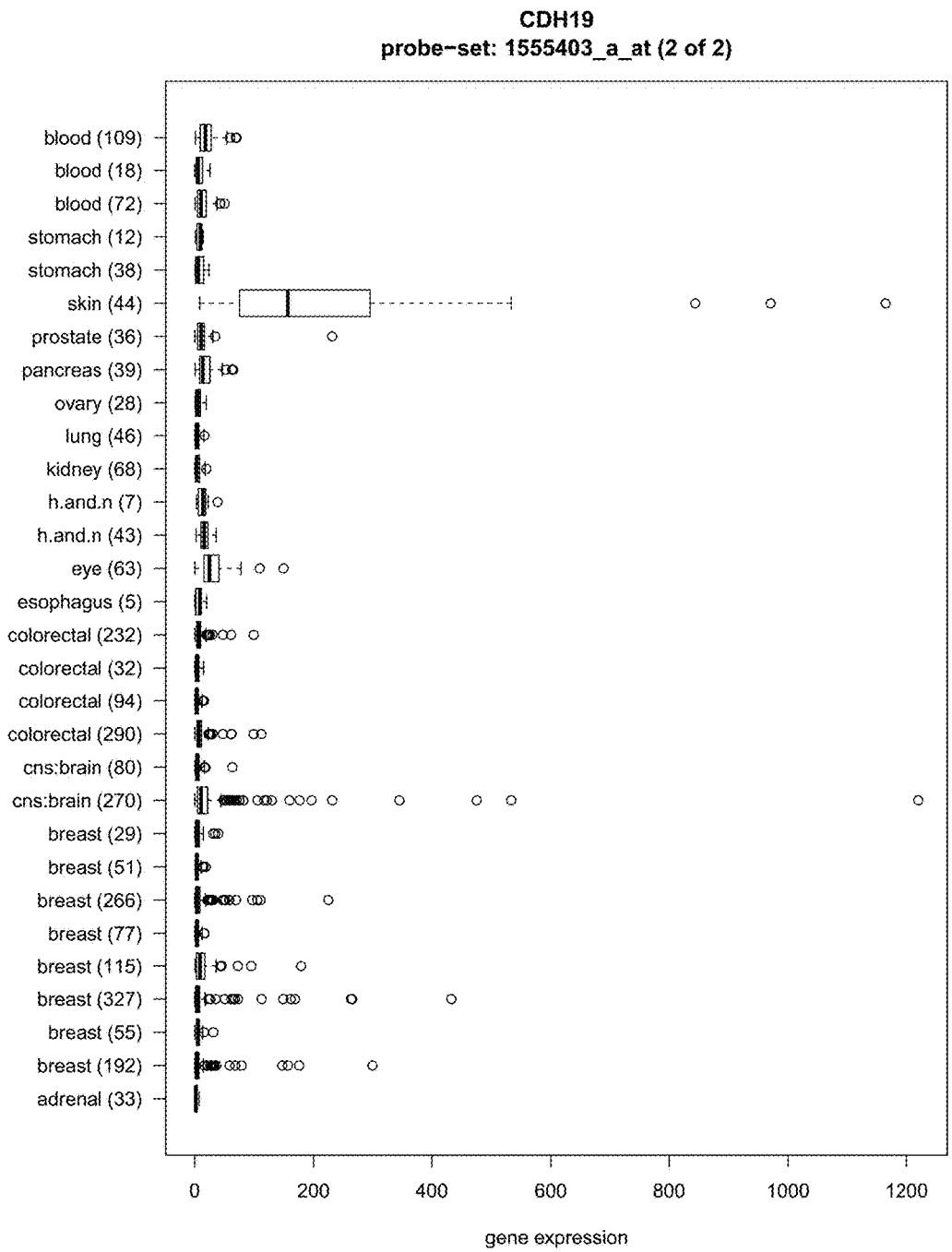
Figure 37:
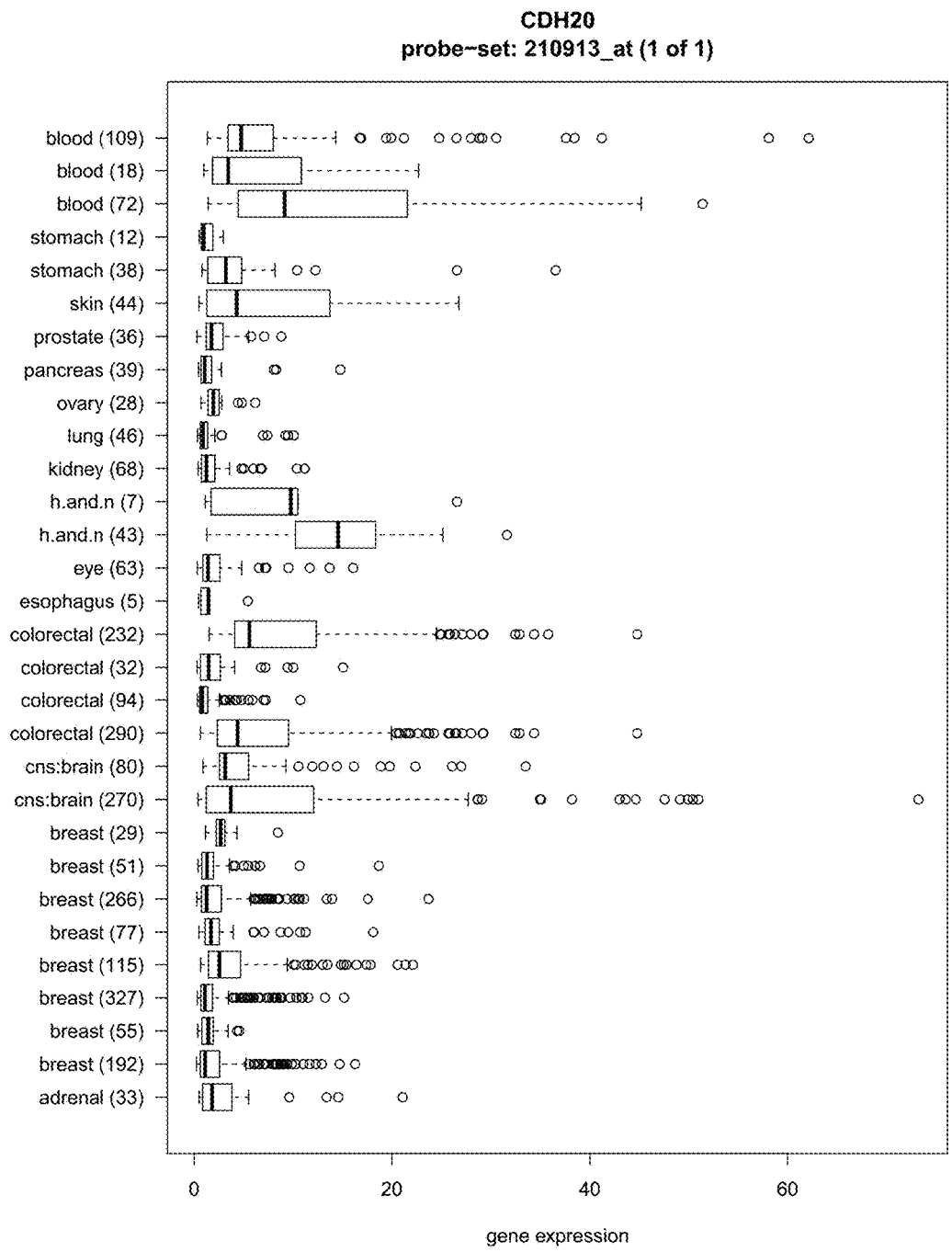
Figure 38:
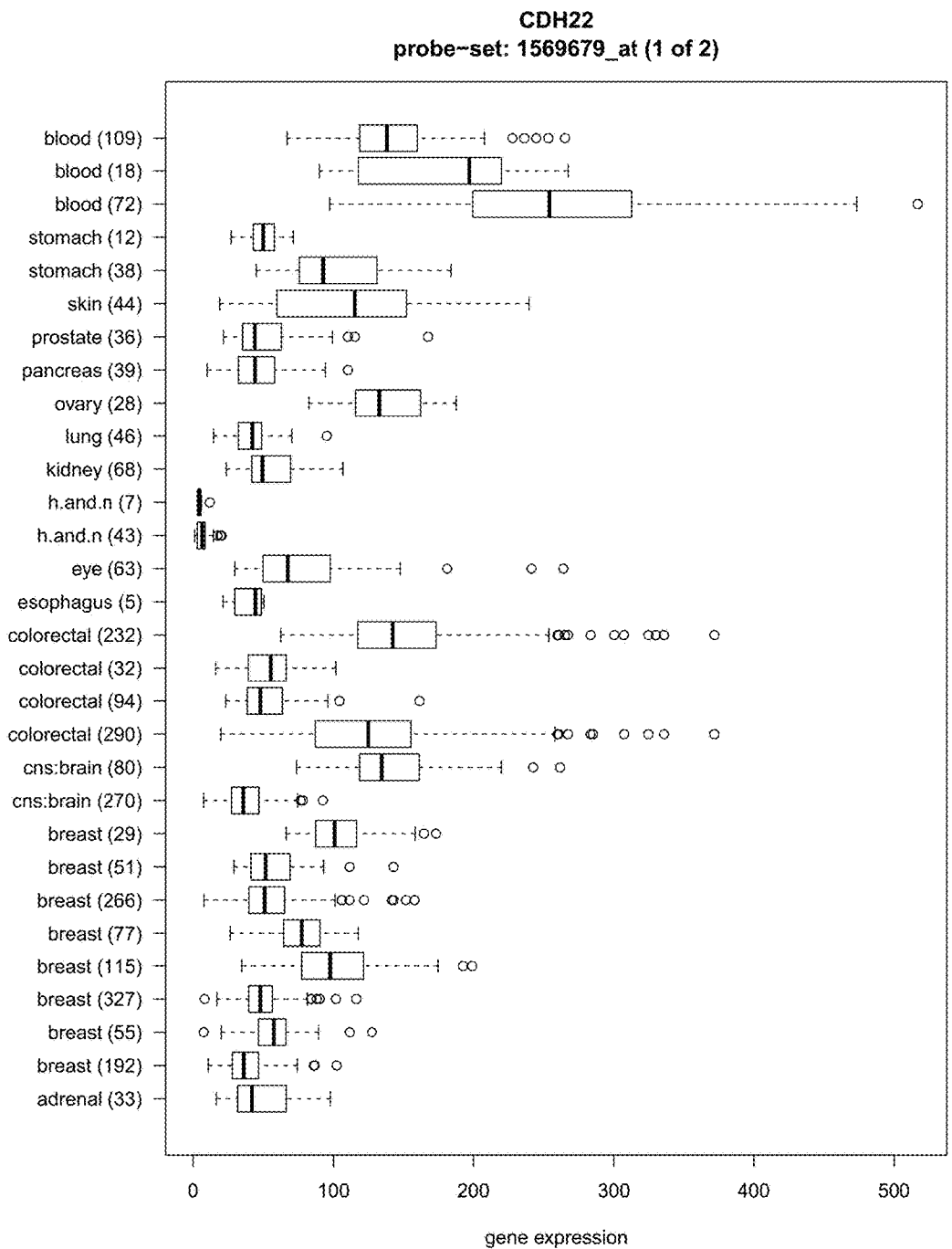
Figure 39:
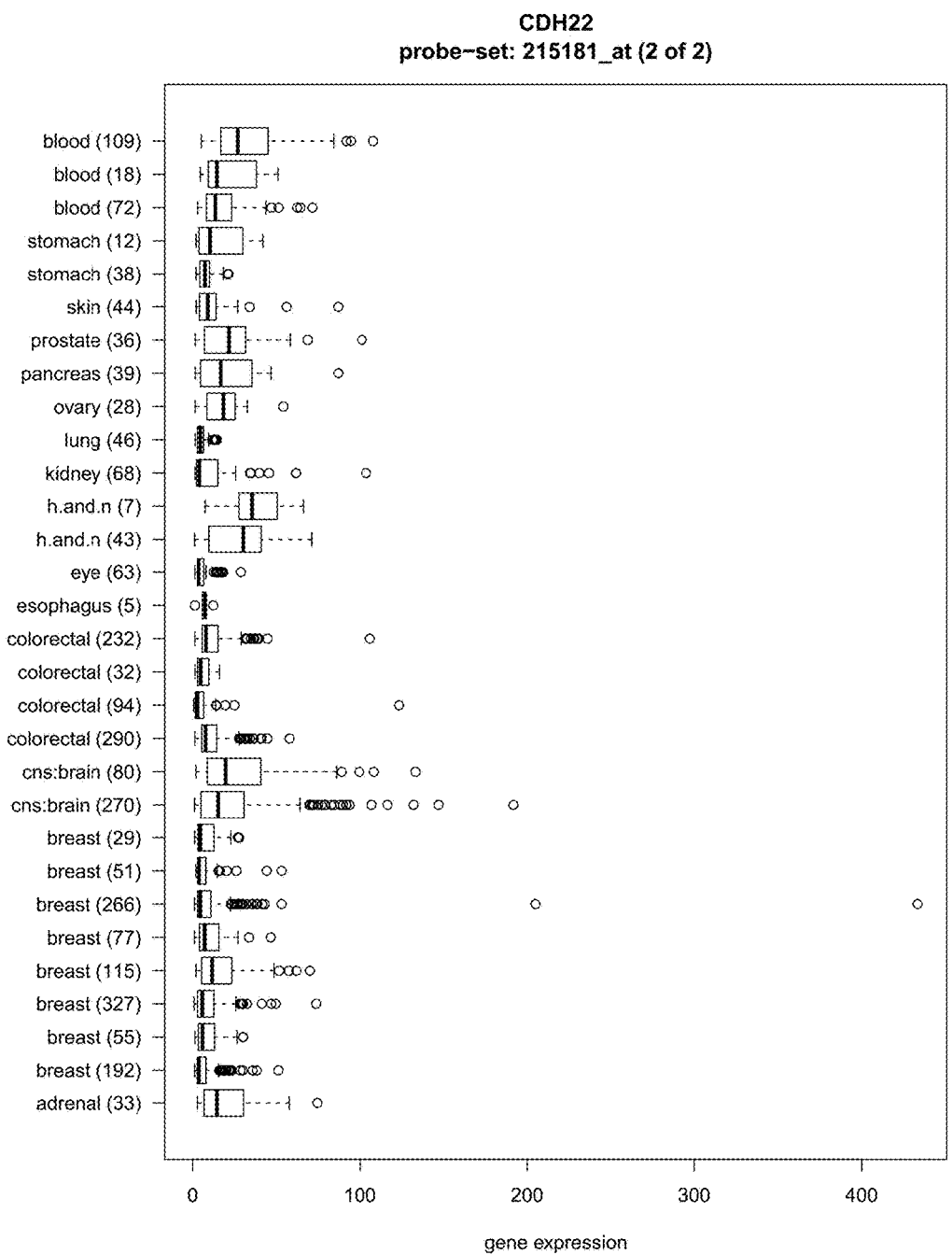
Figure 40:
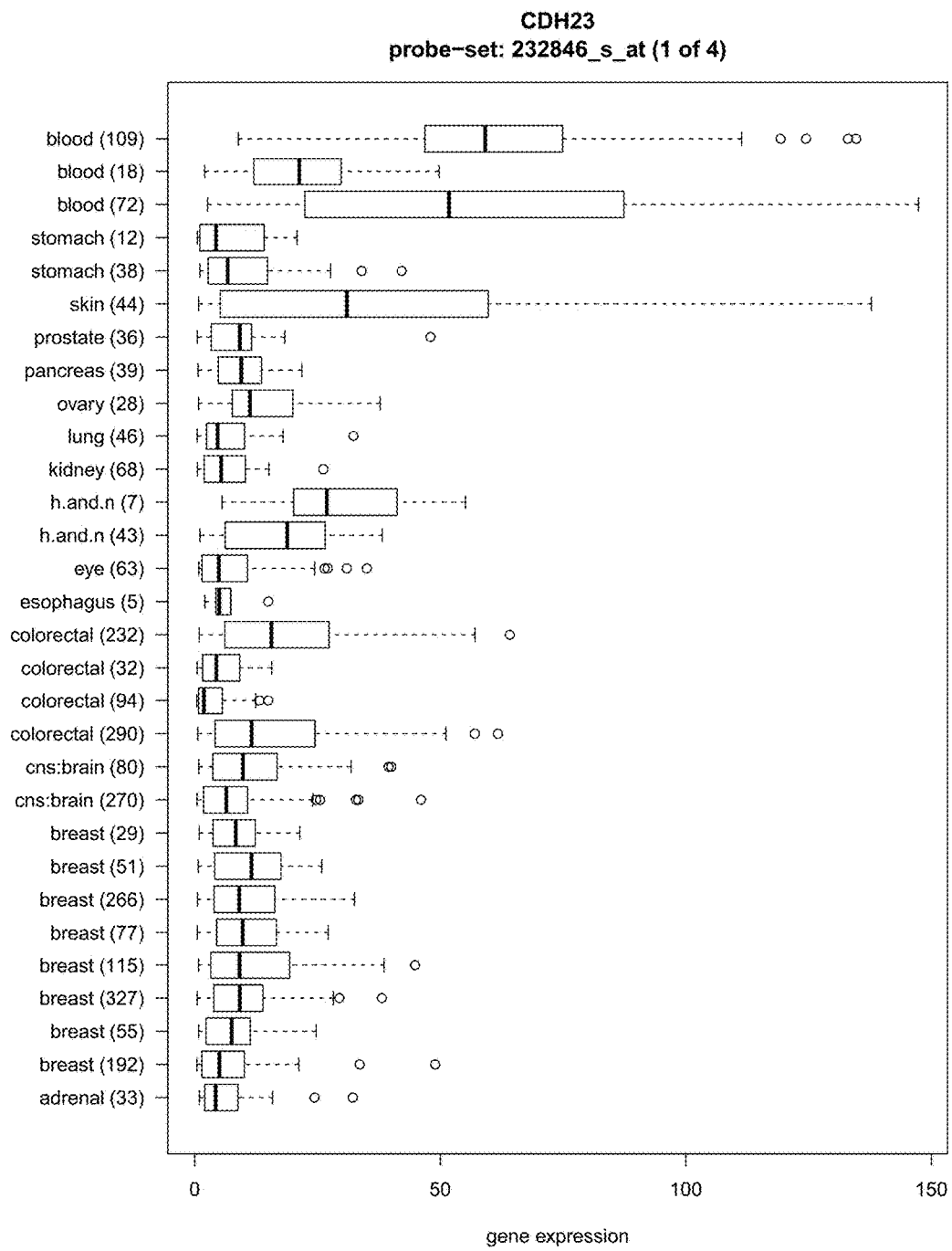
Figure 41:
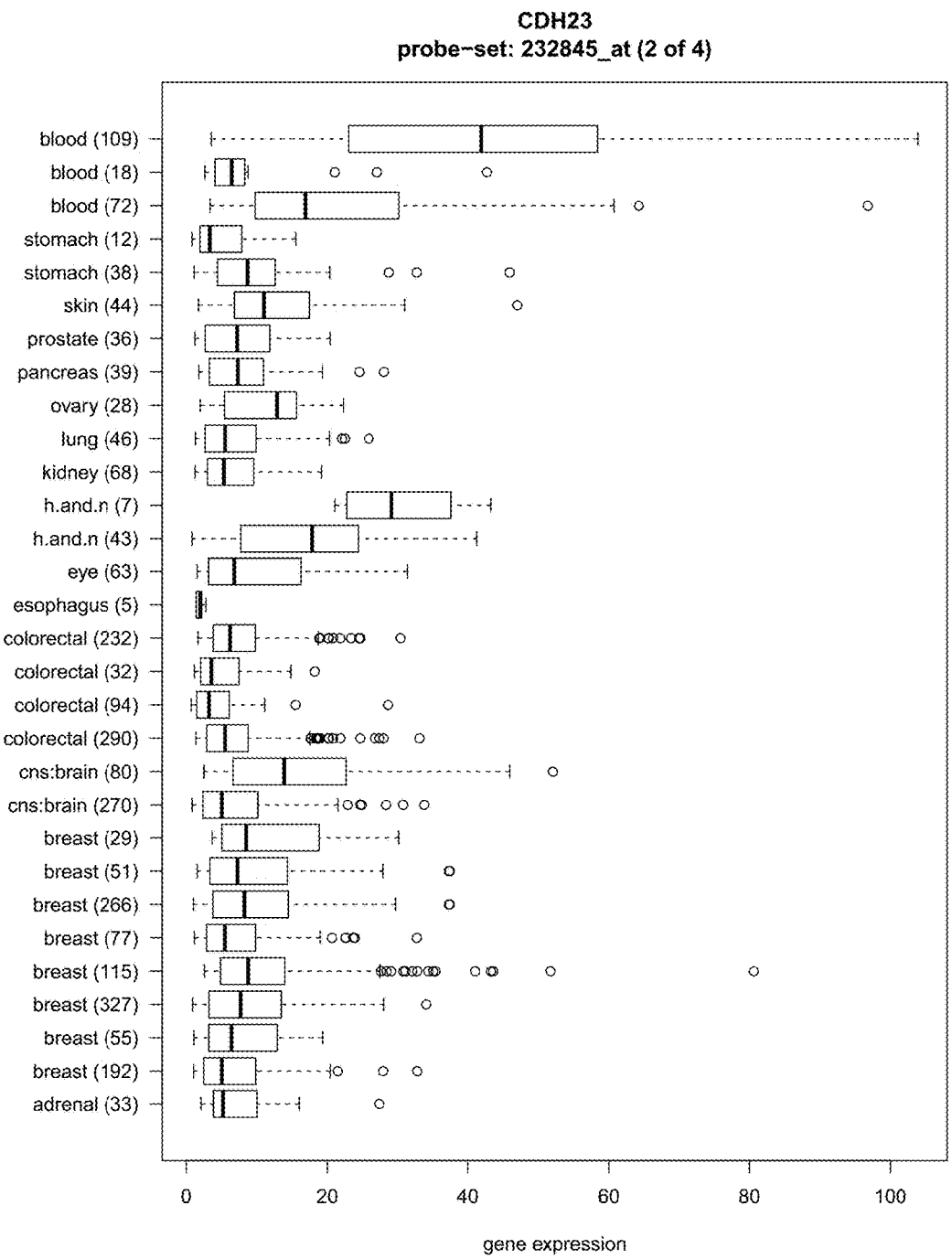
Figure 42:
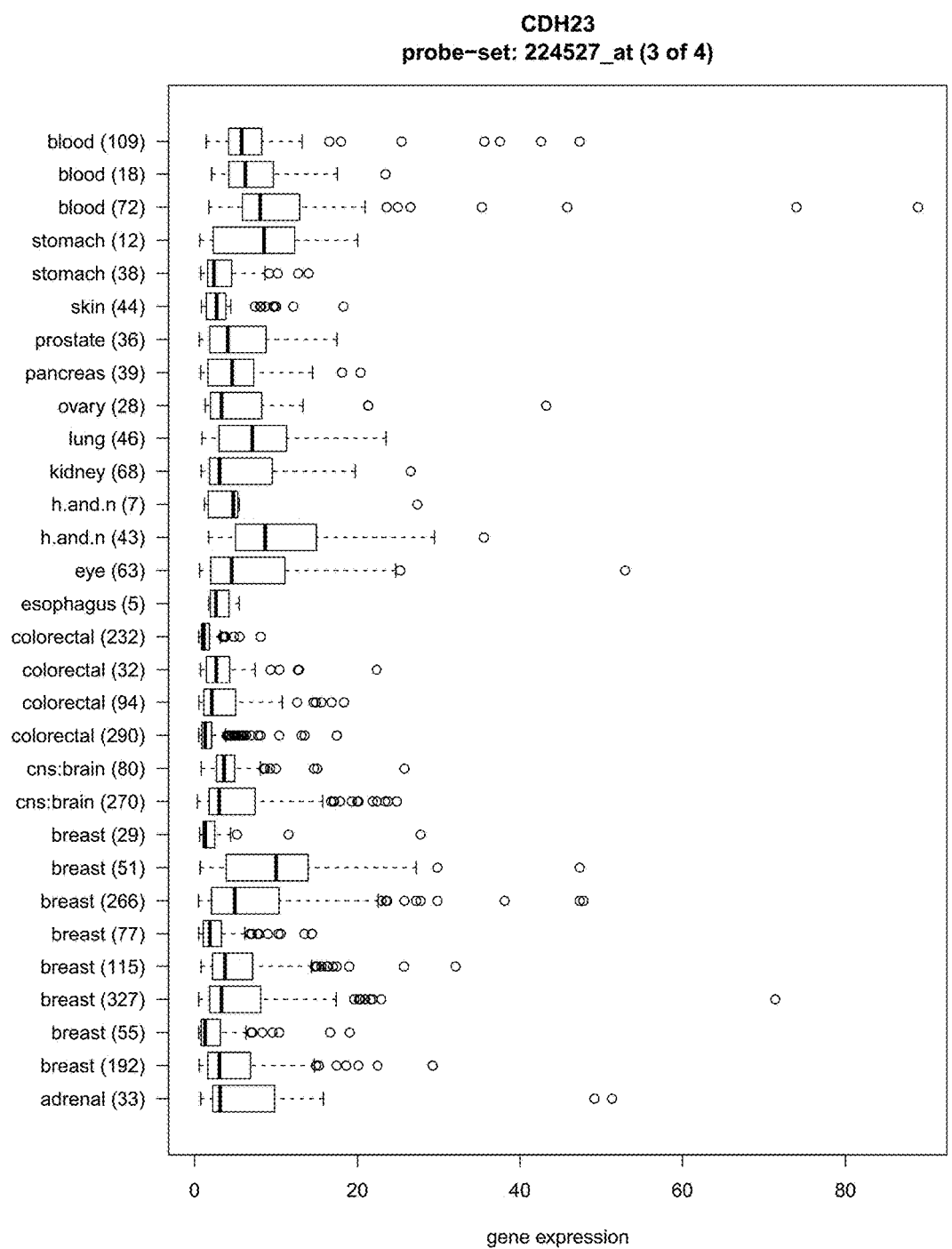
Figure 43:
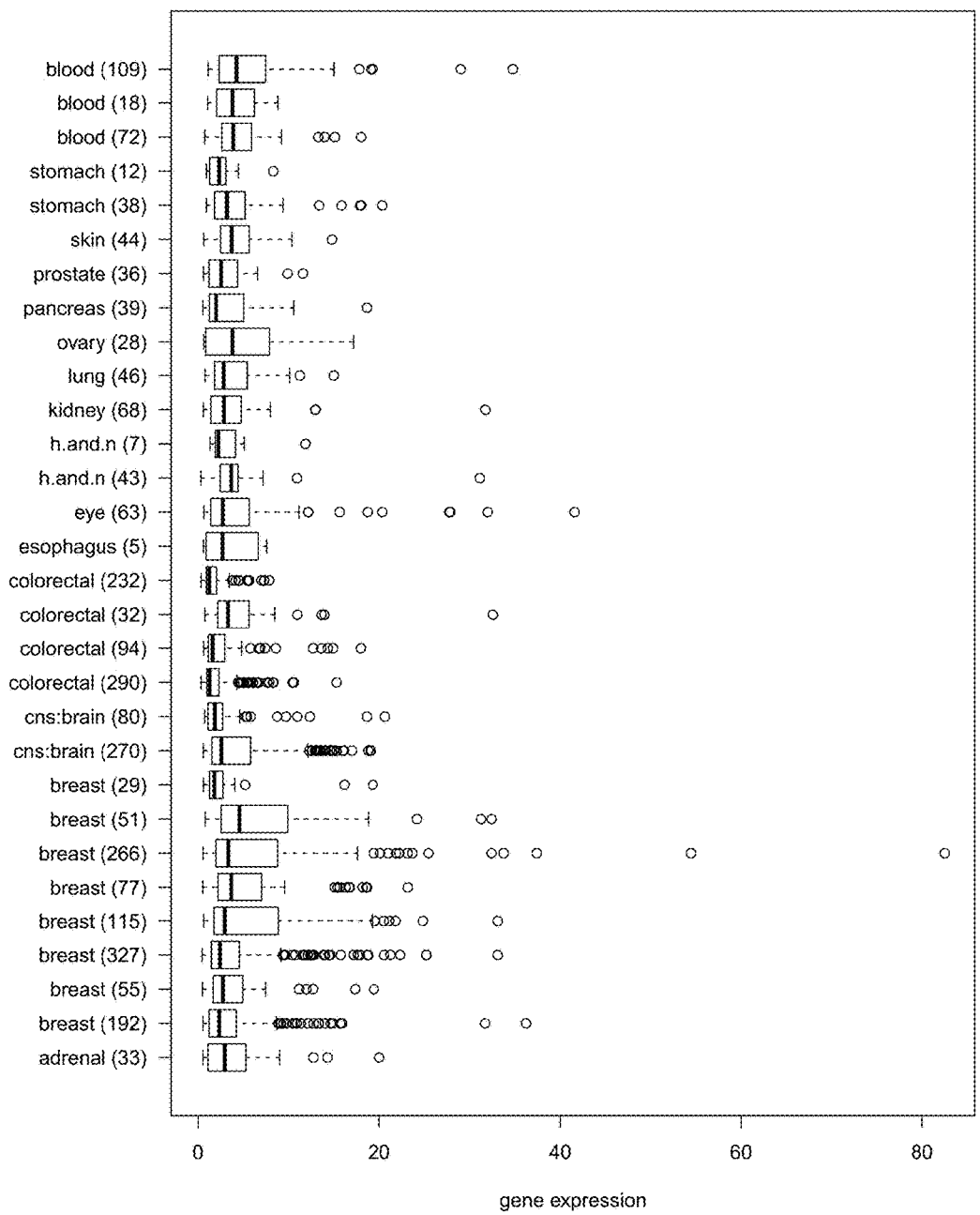
Figure 44:
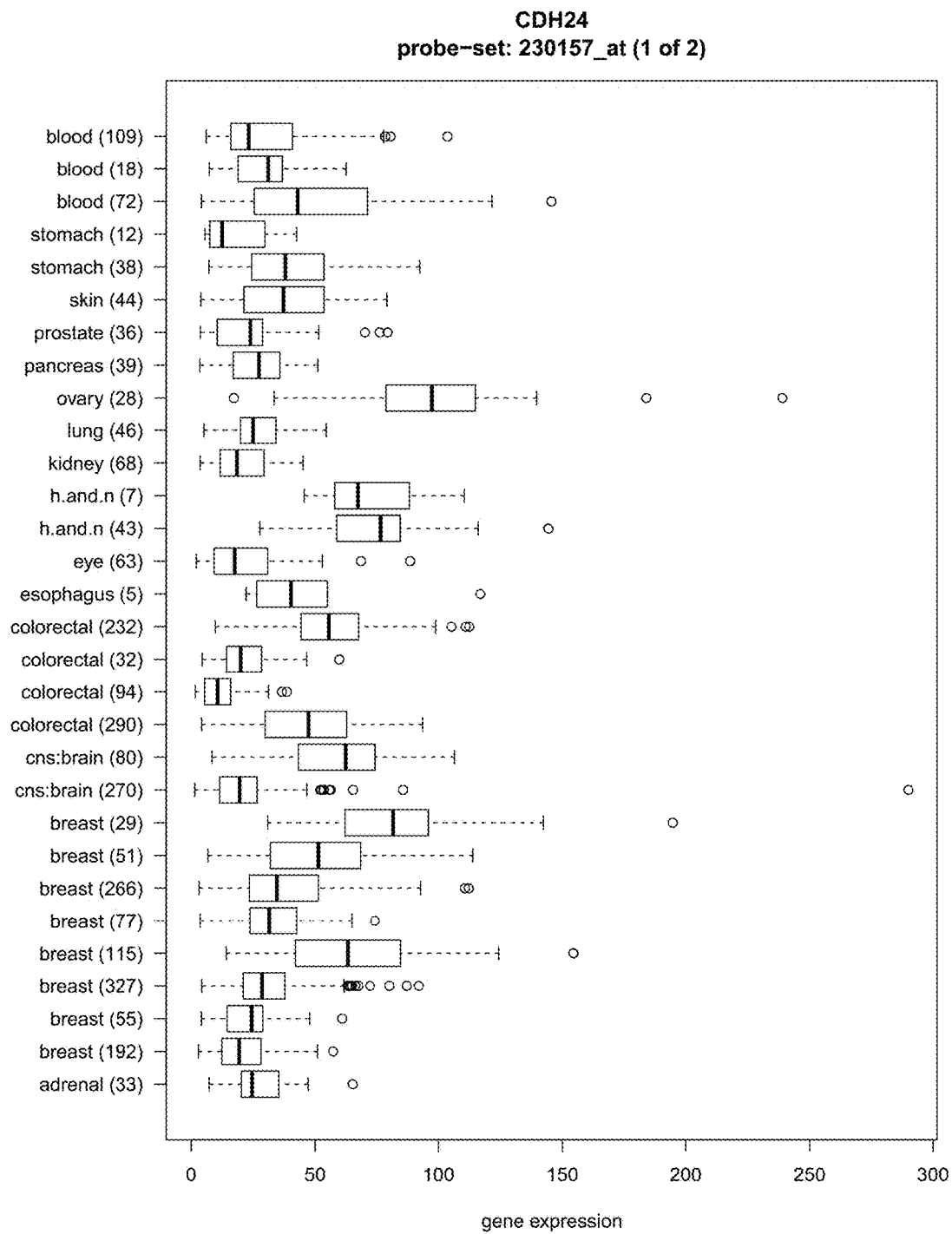
Figure 45:
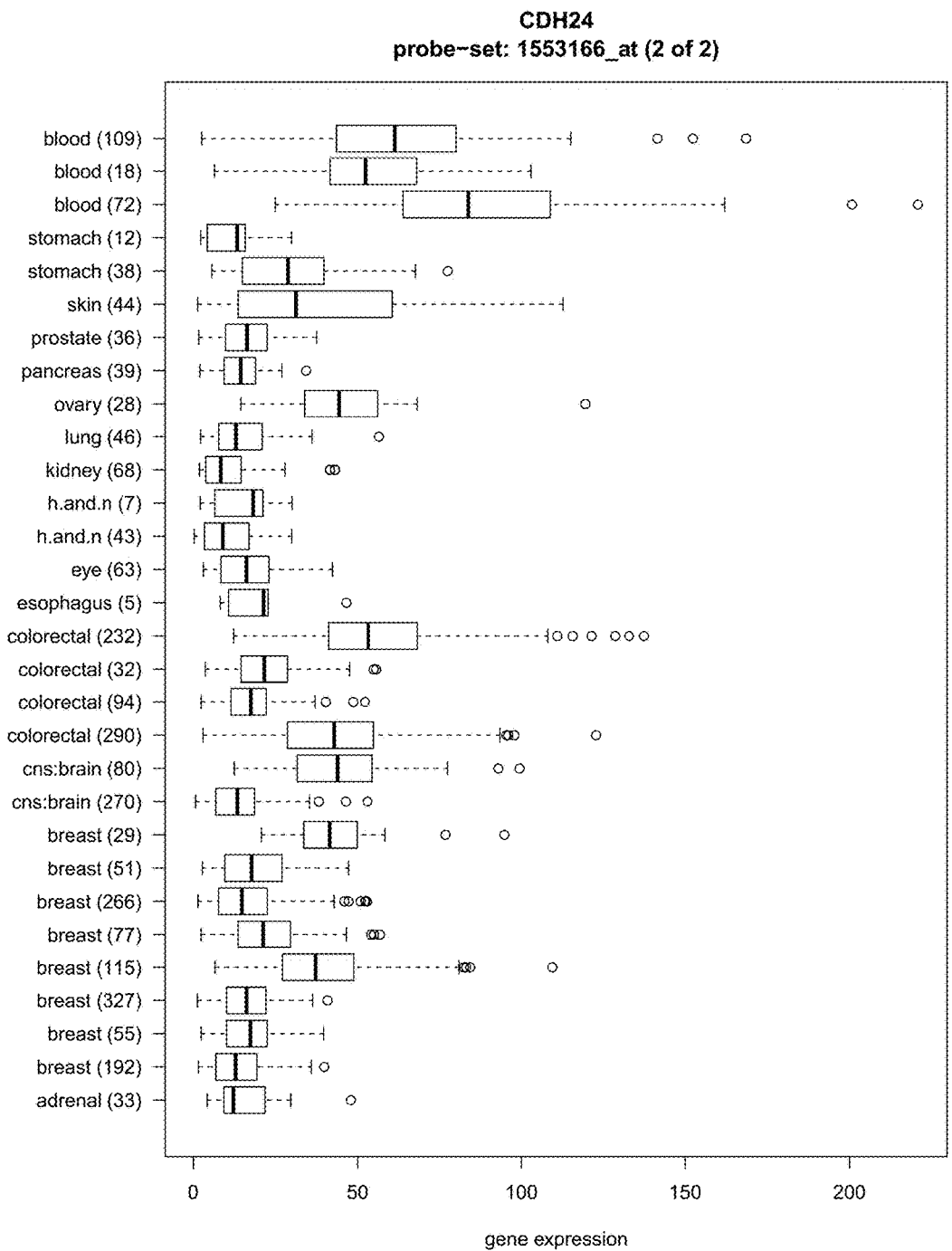
Figure 46:
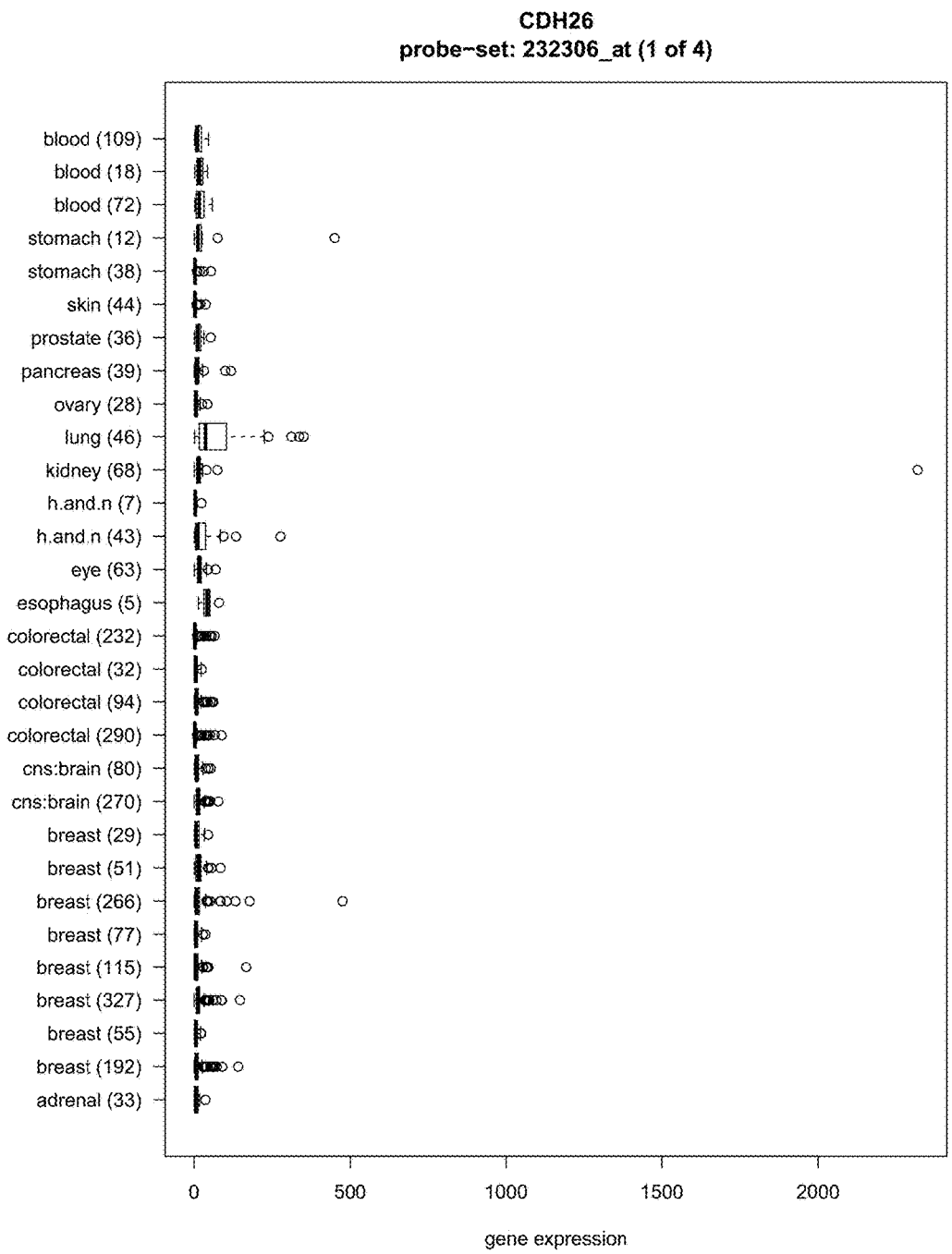
Figure 47:
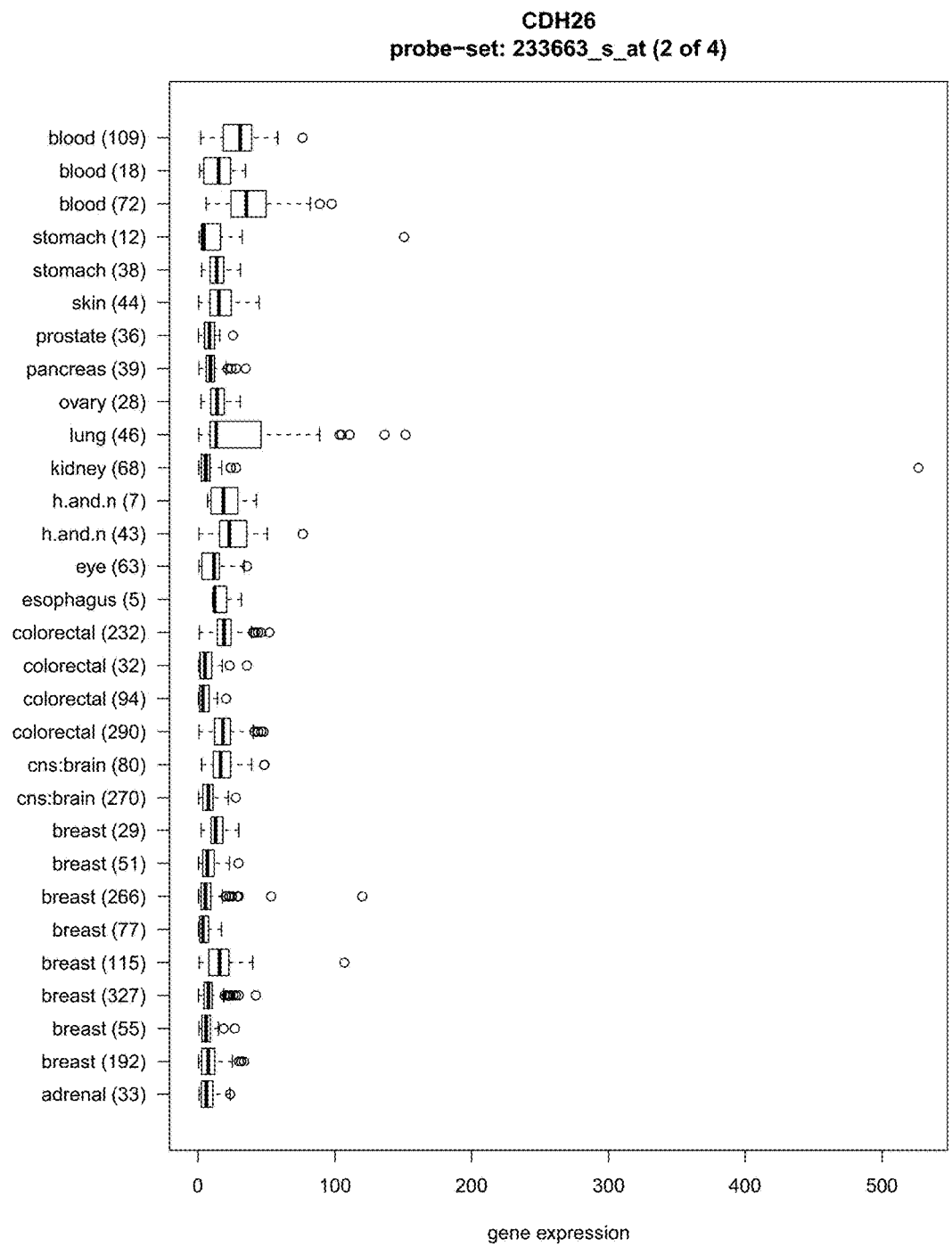
Figure 48:
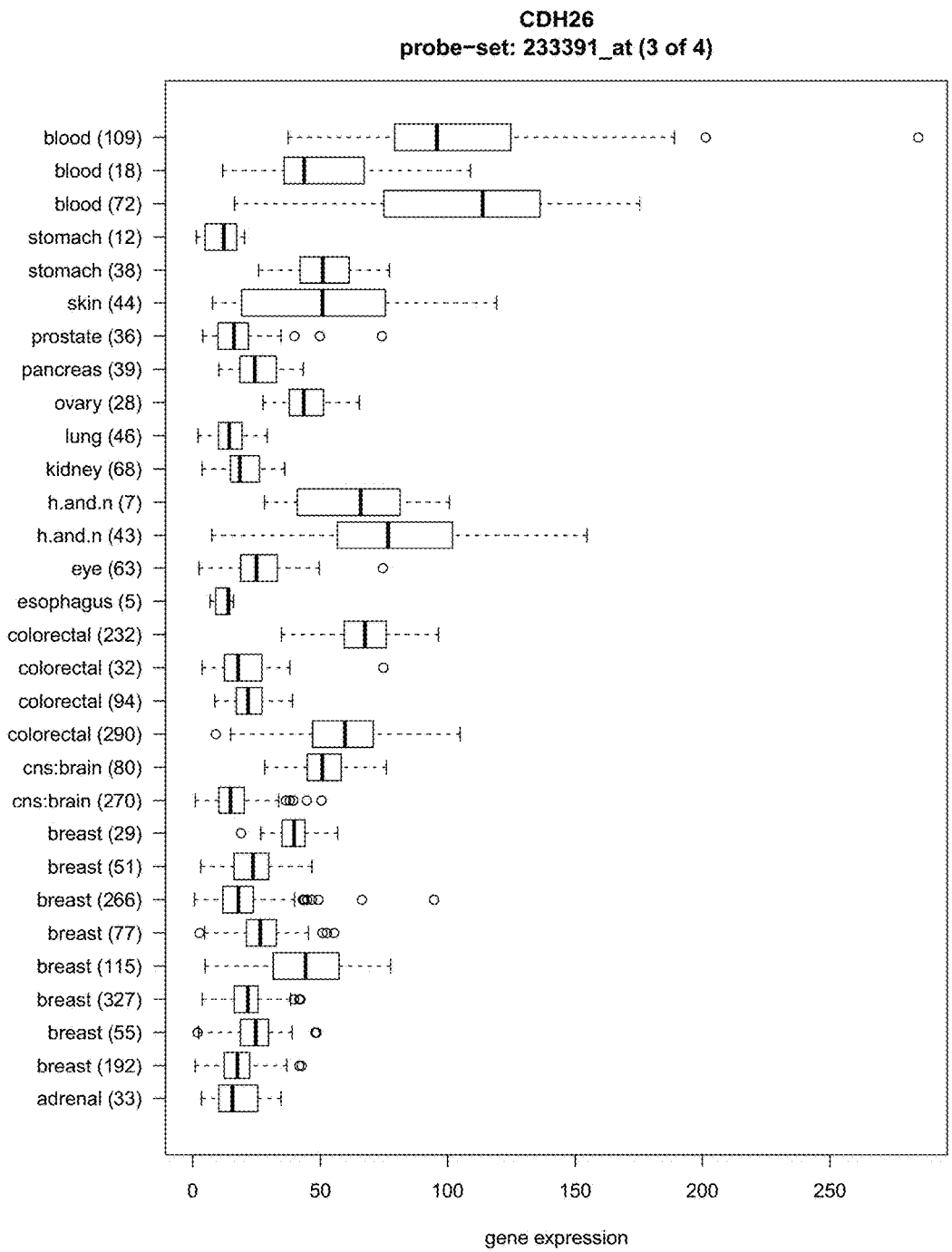
Figure 49:
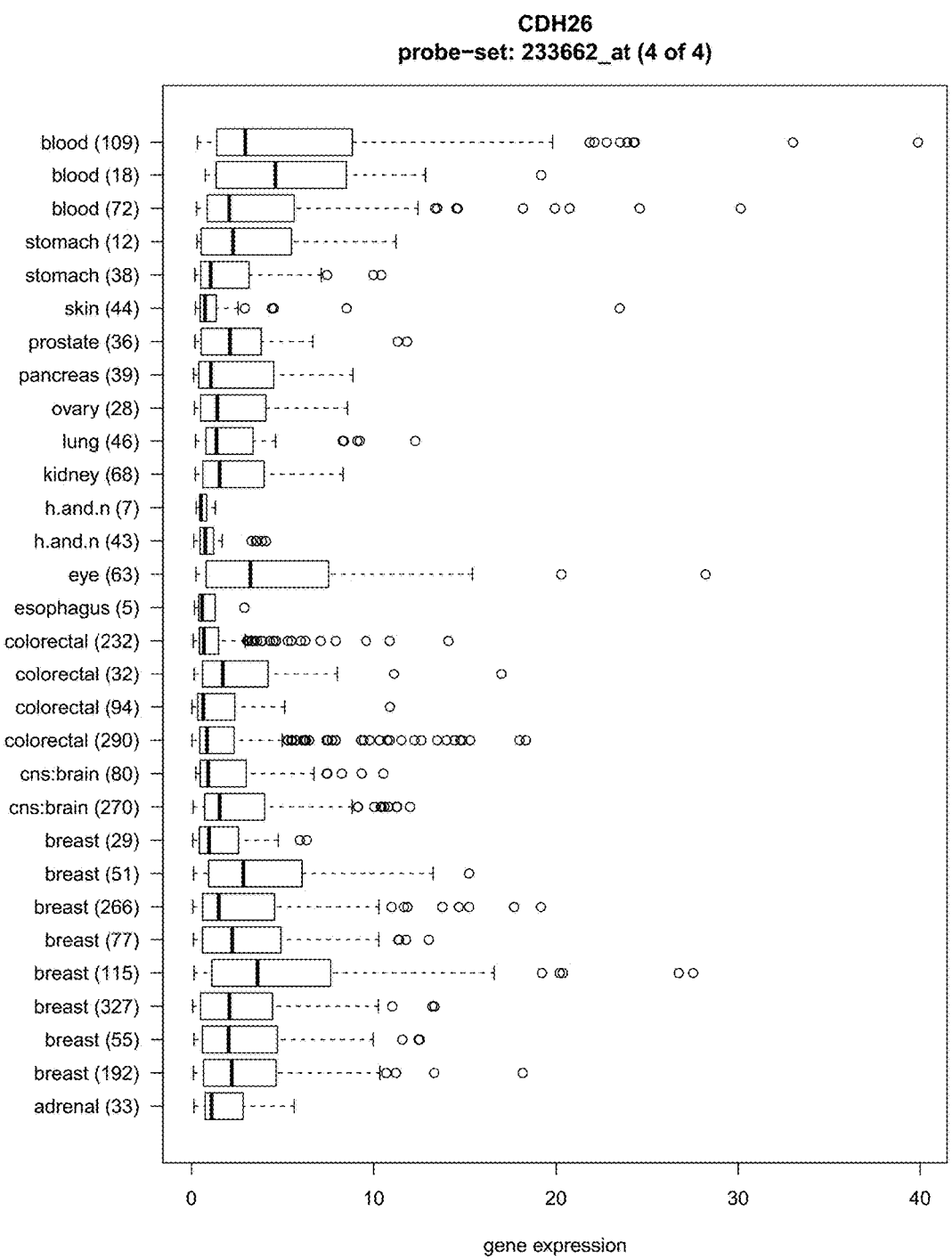
Figure 50A:
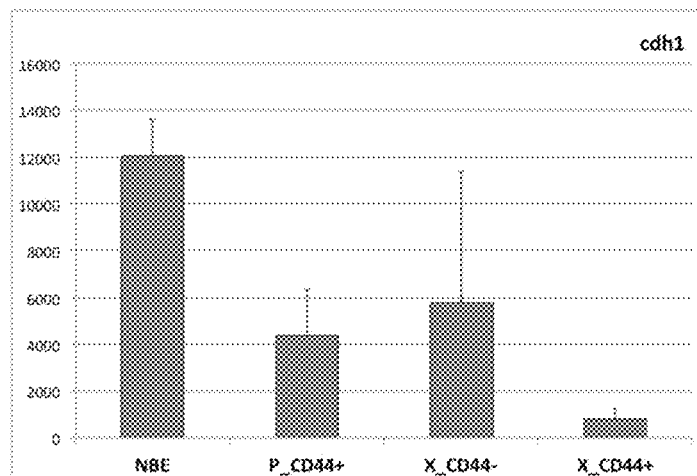
FIGS. 50A-D are bar graphs showing expression in normal breast epithelial cells (NBE), CD44+ cells isolated from pleural effusions (P_CD44+) of human breast cancer patients, and CD44+ (X_CD44+) and CD44− (X_CD44−) cells isolated from tumor xenografts grown in mice of CDH1 (50A), CDH3 (50B), CDH11 (50C), and CDH17 (50D).
Figure 50B:
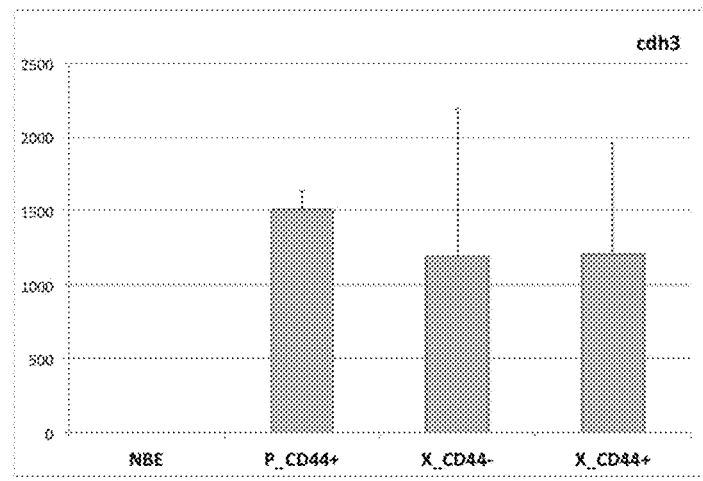
Figure 50C:
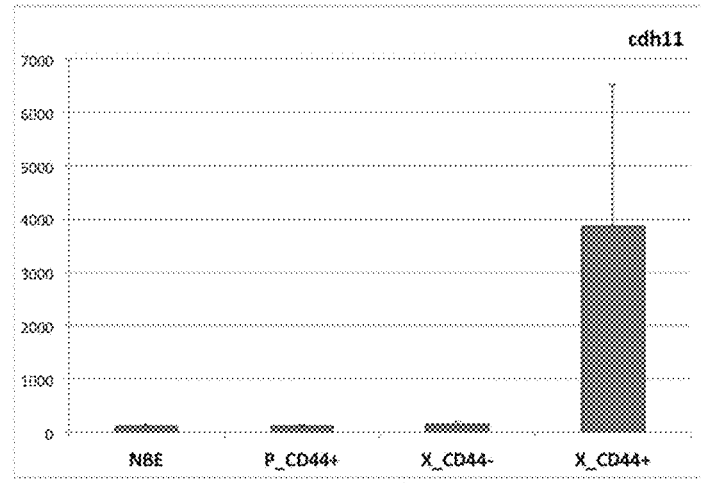
Figure 50D:
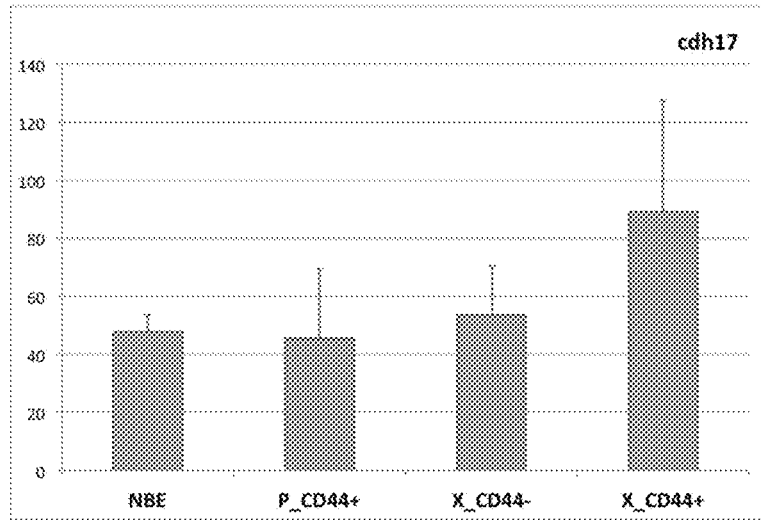
Figure 51A:
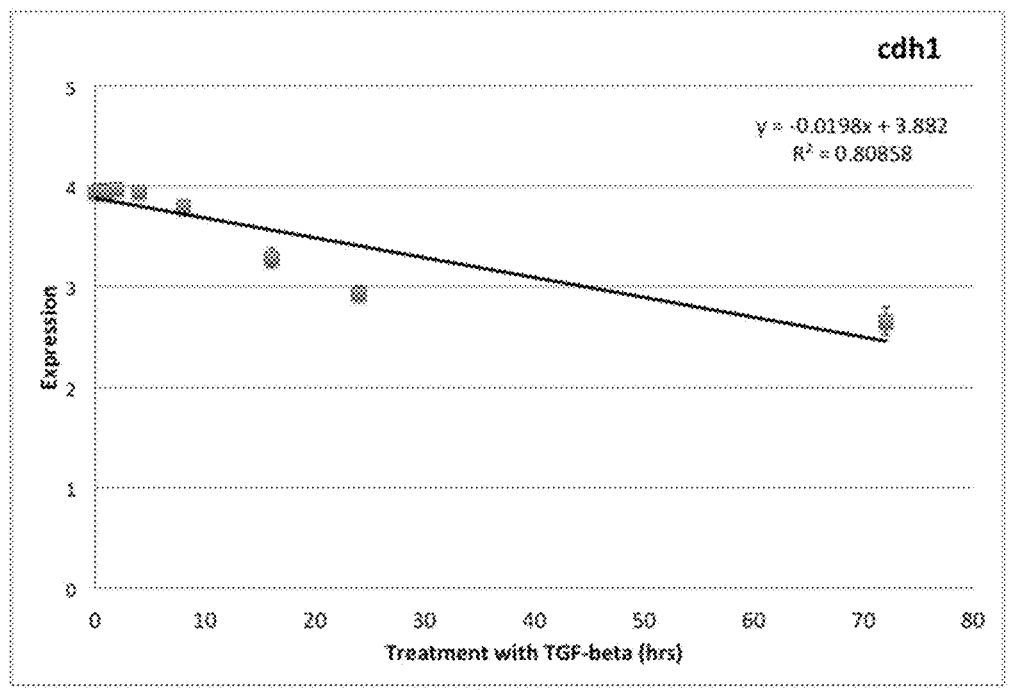
FIGS. 51A-F are line graphs showing the effect of treatment with TGF-beta on epithelial cells, showing that expression of some cadherins increases, e.g., CDH2 (51B) and CDH11 (51E); some have decreased expression, e.g., CDH1 (51A) and CDH17 (51F); and some do not change, 3.g., CDH3 (51C) and CDH5 (51D) during EMT.
Figure 51B:
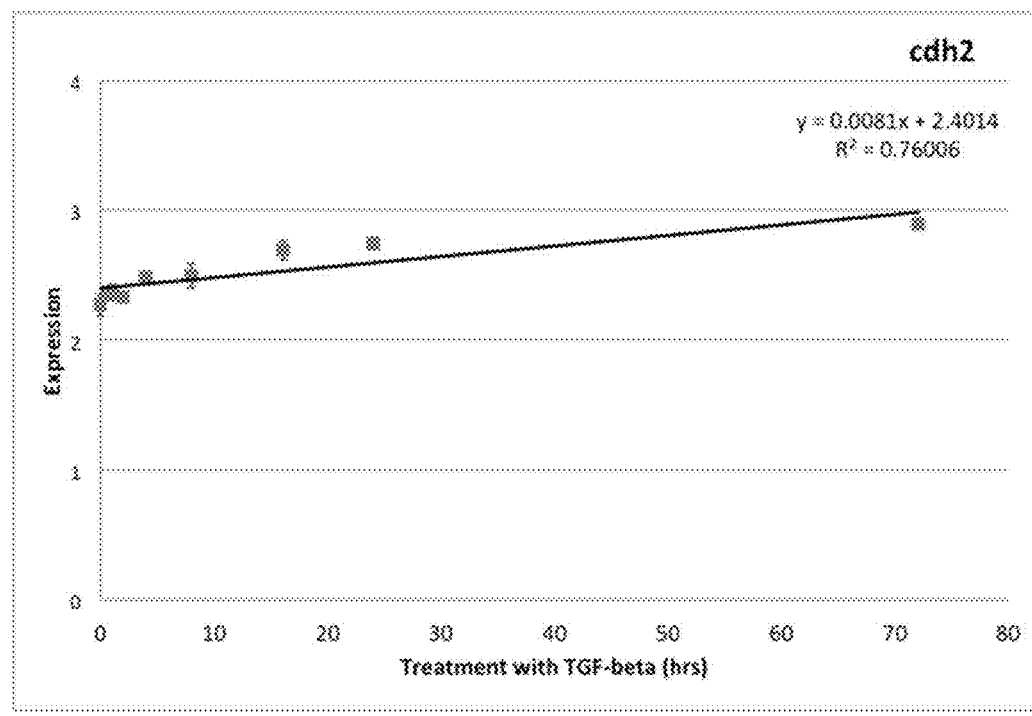
Figure 51C:
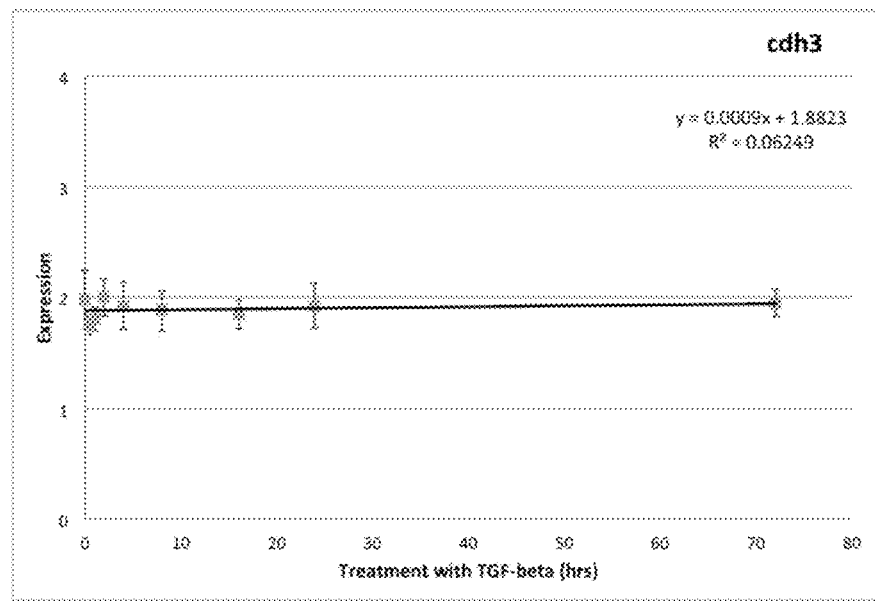
Figure 51D:
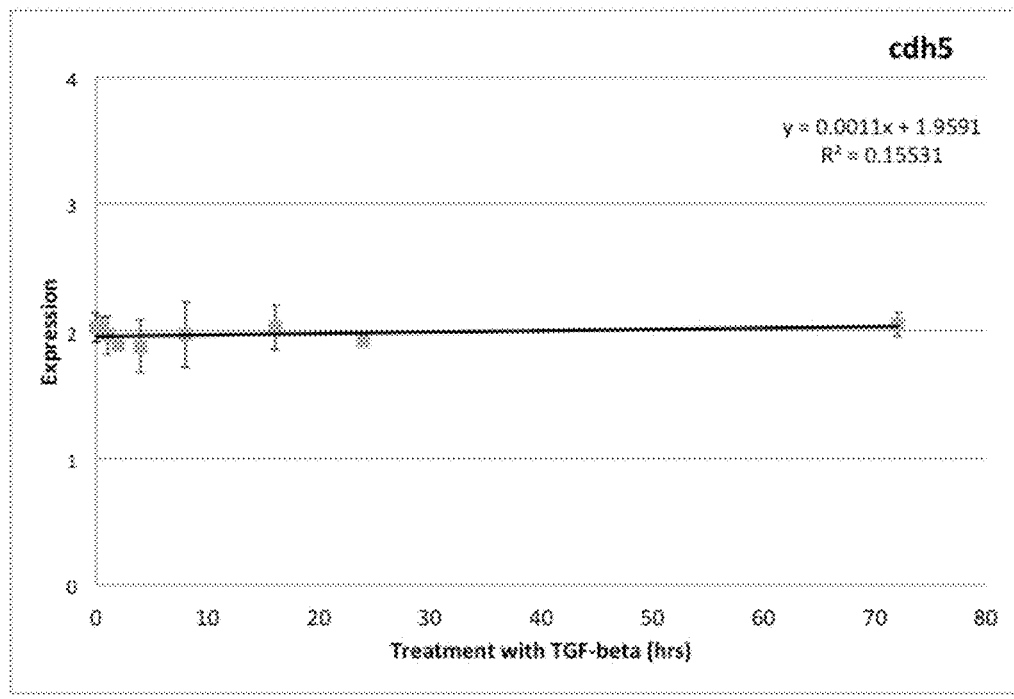
Figure 51E:
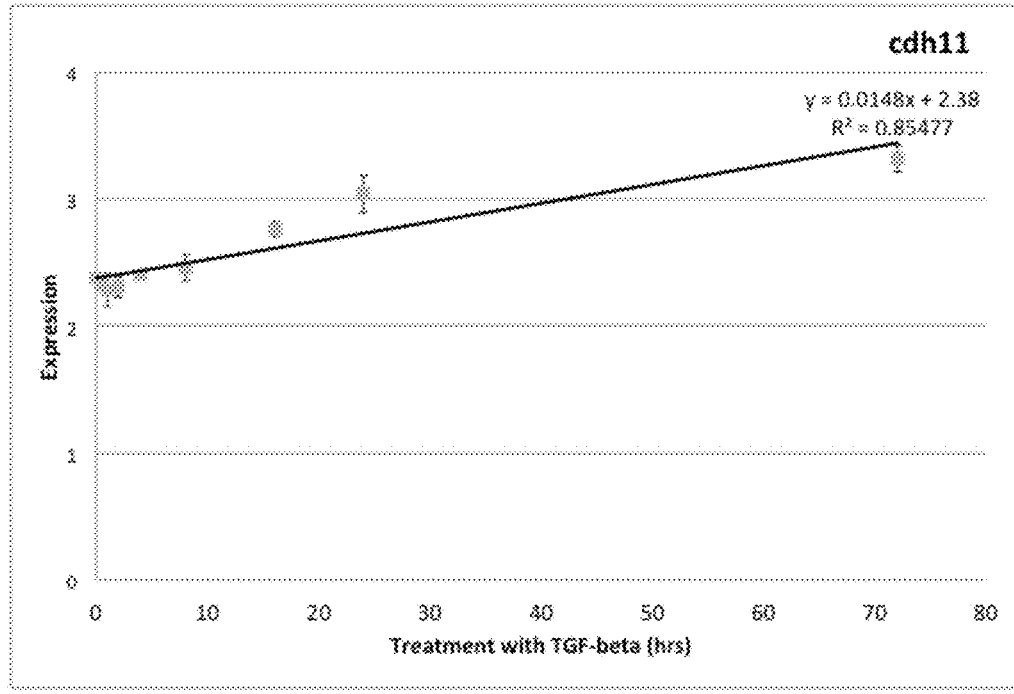
Figure 51F:
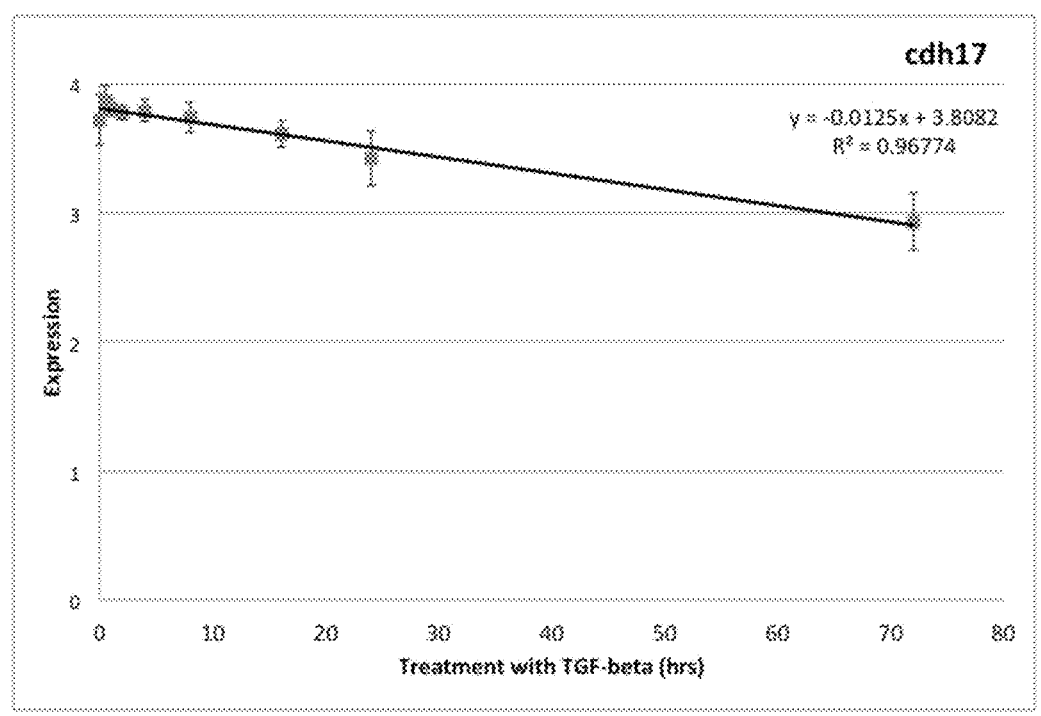

As described herein, certain cadherins are substantially absent from normal blood cells, but are present on a variety of cancerous cell. Thus, specific cadherins would not be detectable in a sample that does not contain cancer cells but would be detectable in a cancer cell-containing sample. This allows for detecting, identifying, isolating, and monitoring the presence of CTCs in a sample, e.g., for diagnosis or monitoring of cancer or therapy, based on the presence of cadherin-expressing cells in a sample (e.g., the presence of cells expressing one or more cadherins at a level above a threshold, e.g., a reference level or detectable level).

Methods

The methods described herein are based on using cell-surface expression of one or more cancer cell surface markers, e.g., cadherins, for detecting, identifying, isolating, and monitoring the presence of CTCs in a sample. The methods include the detection of one or more cadherins, as described herein, and optionally one or more additional cancer cell surface markers, e.g., EpCAM, MUC1, EphB4, EGFR, CEA, and/or HER2.

Detecting Presence of CTCs

In some aspects, the methods described herein are used simply to detect the presence of CTCs in a sample. The sample is contacted with a cadherin binding agent as described herein, and binding to cells that have cell-surface expression of cadherin is measured. As certain cadherins are absent in normal blood, the detection of such binding indicates the presence of tumor cells in the sample, allowing a diagnosis of cancer in the subject. In some embodiments, the methods include detecting the presence of cadherin-expressing cells in a sample (e.g., the presence of cells expressing one or more cadherins at a level above a threshold, e.g., a reference level or detectable level).

Capturing CTCs

The methods described herein can also include isolating or purifying the CTCs, or "capturing" CTCs, from a sample, e.g., to produce a sample that is enriched in CTCs. The methods include contacting the sample with a cadherin binding agent, and capturing cells that bind to the agent. For example, the methods can be performed using microfluidic devices, arrays, or beads as described herein. A sample that is enriched in CTCs is one that is at least 1% pure CTCs, in terms of percent of cells in the sample (i.e., the cells in the sample are at least 20% CTCs). In some embodiments, the enriched sample is at least 2%, 3%, 4%, 5%, 6%, 7%, 8%, 9%, or 10% or more CTCs. The enriched samples can then be used for further analysis, e.g., for the diagnosis of cancer in a subject as described herein.

Monitoring Progression or Development of Cancer

The methods described herein can also be used for monitoring development progress of cancer in a subject. For example, in a subject who has no tumors, the methods can be repeated over time; the appearance of cells expressing surface cadherin indicates that the subject has developed cancer. In a subject who has a benign tumor (and thus no CTCs in a baseline sample), the appearance of cadherin-expressing cells indicates that the subject has developed cancer, e.g., the benign tumor may have become malignant/metastasized.

Samples

Samples useful in the methods described herein include samples comprising bodily fluid from a subject, e.g., blood. In some embodiments, a sample comprising whole blood is used. In some embodiments, red and/or white blood cells are removed from the sample before performing the methods described herein, e.g., using methods known in the art; such methods must selectively remove red and/or white blood cells, leaving any tumor cells present in the sample. A sample can be obtained from a subject using any method known in the art, e.g., venipuncture with a needle large enough to maintain cell integrity.

Cancer Cell Surface Markers

Cadherins are surface antigens that have been implicated in a wide variety of cancers; see, e.g. Berx and van Roy, Cold Spring Harb Perspect Biol, 1(6):a003129 (2009); Kim et al., Cancer, 110(12):2785-92 (2007); Peinado et al. Int J Dev Biol, 48(5-6):365-75 (2004), and offer a source of new CTC capture epitopes. Additional cancer cell surface markers have been identified and can be used in the methods described herein. See, e.g., Table 1 of Man et al., J Clinic Experiment Pathol 1:102 (2011); doi:10.4172/2161-0681.1000102, and references cited therein. For example, EpCAM is present on a wide variety of epithelial cancers (carcinomas, e.g., lung, prostate, colon, breast, bladder), but relatively absent in normal blood cells. MUC-1 is present on colorectal, ovarian, breast, and prostate cancer cells.

A number of cadherins are useful in the methods and devices described herein. Table A provides a list of cadherins that can be used, with GenBank Accession Nos. for human nucleic acid and protein sequences; Table B provides a list of additional cancer cell surface markers that can optionally be used in addition to the cadherins. One of skill in the art will appreciate that, when detecting cancer in subjects of other species, sequences from those species should be used; such sequences are known in the art and can be obtained using routine bioinformatics.

TABLE A

Cadherin Cancer Cell Surface Markers

| Gene Symbol | Official Full Name | GenBank Accession Nos. | |
| --- | --- | --- | --- |
| | | Nucleic Acid (mRNA) | Protein |
| CDH1 | cadherin 1, type 1, E-cadherin (epithelial) | NM_004360.3 | NP_004351.1 |
| CDH2 | cadherin 2, type 1, N-cadherin (neuronal) | NM_001792.3 | NP_001783.2 |
| CDH3 | cadherin 3, type 1, P-cadherin (placental) | NM_001793.4 | NP_001784.2 |
| CDH4 | cadherin 4, type 1, R-cadherin (retinal) | NM_001794.2 | NP_001785.2 |
| CDH5 | cadherin 5, type 2 (vascular endothelium) | NM_001795.3 | NP_001786.2 |
| CDH9 | cadherin 9, type 2 (T1-cadherin) | NM_016279.3 | NP_057363.3 |
| CDH11 | cadherin 11, type 2, OB-cadherin (osteoblast) | NM_001797.2 | NP_001788.2 |
| CDH17 | cadherin 17, LI cadherin (liver-intestine) | NM_004063.3 (v1) NM_001144663.1 (v2) | NP_004054.3 (v1) NP_001138135.1 (v2) |

TABLE A-continued

Cadherin Cancer Cell Surface Markers

| | | GenBank Accession Nos. | |
|---|---|---|---|
| Gene Symbol | Official Full Name | Nucleic Acid (mRNA) | Protein |
| CDH19 | cadherin 19, type 2 | NM_021153.2 | NP_066976.1 |
| PCDH9 | protocadherin 9 | NM_203487.2 (v1) | NP_982354.1 (v1) |
| | | NM_020403.4 (v2) | NP_065136.1 (2) |
| PCDHB13 | protocadherin beta 13 | NM_018933.2 | NP_061756.1 |

TABLE B

Additional Cancer Cell Surface Markers

| | | GenBank Accession Nos. | |
|---|---|---|---|
| Gene Symbol | Official Full Name | Nucleic Acid (mRNA) | Protein |
| EPCAM | epithelial cell adhesion molecule | NM_002354.2 | NP_002345.2 |
| MUC-1 | mucin 1, cell surface associated | NM_002456.5* | NP_002447.4* |
| HER2 | v-erb-b2 erythroblastic leukemia viral oncogene homolog 2, neuro/glioblastoma derived oncogene homolog (avian) | Isoform a: NM_004448.2 Isoform b: NM_001005862.1 | NP_004439.2 NP_001005862.1 |
| CEA | Carcinoembryonic antigen | NM_001712.4*** | NP_001703.2*** |
| EGFR | epidermal growth factor receptor | NM_005228.3** | NP_005219.2** |
| EphB4 | EPH receptor B4 | NM_004444.4 | NP_004435.3 |

*MUC-1 has a number of variants, any of which can be used in the methods described herein. The sequence provided is variant 1.
**EGFR has a number of variants, any of which can be used in the methods described herein. The sequence provided is isoform a.
***CEA is a family of genes; any can be used here. The present sequences are for isoform 1 of CEACAM1.

Cancer Cell Surface Marker-Binding Agents

In some embodiments, the methods include the use of agents that bind to the one or more cancer cell surface markers, e.g., bind specifically to the markers. Any moiety that binds with sufficient specificity can be used. In some embodiments, antibodies (or antigen fragments thereof) that bind to the one or more cadherins are used. The term "antibody" as used herein refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments the antibody has effector function and can fix complement. In some embodiments, the antibody has reduced or no ability to bind an Fc receptor. For example, the antibody can be an isotype or subtype, fragment or other mutant, which does not support binding to an Fc receptor, e.g., it has a mutagenized or deleted Fc receptor binding region. Methods for making antibodies and fragments thereof are known in the art, see, e.g., Harlow et. al., editors, *Antibodies: A Laboratory Manual* (1988); Goding, *Monoclonal Antibodies: Principles and Practice*, (N.Y. Academic Press 1983); Howard and Kaser, *Making and Using Antibodies: A Practical Handbook* (CRC Press; 1st edition, Dec. 13, 2006); Kontermann and Dühel, *Antibody Engineering Volume 1 (Springer Protocols)* (Springer; 2nd ed., May 21, 2010); Lo, *Antibody Engineering: Methods and Protocols (Methods in Molecular Biology)* (Humana Press; Nov. 10, 2010); and Dühel, *Handbook of Therapeutic Antibodies: Technologies, Emerging Developments and Approved Therapeutics*, (Wiley-VCH; 1 edition Sep. 7, 2010).

A number of antibodies that bind to the cancer cell surface markers described herein are commercially available, e.g., from one or more of the following suppliers: Biorbyt, R&D Systems, Abcam, Bioss Inc., Fitzgerald, Raybiotech, Genway, Abbiotec, Life Technologies, EMD Millipore, R&D Systems, Lifespan Biosciences, Thermo Fisher Scientific, Inc., AbD Serotec, ACris Antibodies, GenScript, Cell Signaling Technology, OriGene, Novus Biologicals, Epitomics, Abgent, Aviva Systems Biology, Abnova, ProSci, Biovisoin, GeneTex, and/or Uscn.

In some embodiments, protein binding partners are used. Some exemplary cadherin protein binding partners that can be used in the present methods and devices include ankyrin-1, beta-catenin, and FGFR; either the full length or a fragment that binds to the cadherin can be used.

In some embodiments, nucleic acid based binding partners called aptamers are used. Nucleic acids can be selected to bind selectively to cadherin protein targets; see, e.g., Ellington, A. D. and J. W. Szostak, Nature, 346(6287):818-22 (1990); Gupta, S. et al., Appl Immunohistochem Mol Morphol, 19(3):273-8 (2011).

In some embodiments, the binding agent can be coupled to a detectable or imaging agent. Detectable agents are well known in the art and include paramagnetic agents, bioluminescent or fluorescent labels (e.g., GFP, FITC, rhodamine, or Texas Red), radioactive isotopes, and colorimetric/enzymatic agents (e.g., HRP, B-galactosidase).

In some embodiments, the binding agent is coupled to a surface, e.g., a surface in a microfluidic device as described herein, a surface of an array (e.g., a microarray), or a bead. In a preferred embodiment, the antibody is coupled to a magnetic bead, e.g., a paramagnetic nanoparticle, e.g., cross-linked iron oxide (CLIO) nanoparticles; see, e.g., US 20110046004; Josephson et al., Bioconjug. Chem., 10(2): 186-91 (1999). Other devices can also be used, e.g., the CellSearch (FDA Final rule. Fed Regist 69: 26036-26038 (2004); MagSweeper, Talasaz et al., Proc Natl Acad Sci USA (2009) 106: 3970-3975; or Nanostructured Substrates, Wang et al., Angew Chem Int Ed Engl 50: 3084-3088 (2011). These devices can be modified for use with the present methods.

Microfluidic Devices

In some embodiments, microfluidic (e.g., "lab-on-a-chip") devices are used in the present methods. Such devices have been successfully used for microfluidic flow cytometry, continuous size-based separation, and chromatographic separation. In general, methods in which expression of the biomarkers is detected in circulating tumor cells (CTCs) can be used for the early detection of cancer, e.g., early detection of tumors of epithelial origin, e.g., pancreatic, lung, breast, prostate, renal, ovarian or colon cancer.

The devices can be used for separating CTCs from a mixture of cells, or preparing an enriched population of CTCs. In particular, such devices can be used for the isolation of CTCs from complex mixtures such as whole blood.

A variety of approaches can be used to separate CTCs from a heterogeneous sample. For example, a device can include an array of multiple posts arranged in a hexagonal packing pattern in a microfluidic channel upstream of a block barrier. The posts and the block barrier can be functionalized with different binding moieties. For example, the posts can be functionalized with one or more antibodies that bind to a (one or more) cadherin cancer cell surface marker as described herein to capture circulating tumor cells (CTCs); see, e.g., Nagrath et al., Nature 450:1235-1239 (2007), optionally with downstream block barriers functionalized with to capture biomarker nucleic acids or proteins.

Processes for enriching specific particles from a sample are generally based on sequential processing steps, each of which reduces the number of undesired cells/particles in the mixture, but one processing step may suffice in some embodiments. Devices for carrying out various processing steps can be separate or integrated into one microfluidic system. The devices include devices for cell/particle binding, devices for cell lysis, devices for arraying cells, and devices for particle separation, e.g., based on size, shape, and/or deformability or other criteria. In certain embodiments, processing steps are used to reduce the number of cells prior to introducing them into the device or system. In some embodiments, the devices retain at least 75%, e.g., 80%, 90%, 95%, 98%, or 99% of the desired cells compared to the initial sample mixture, while enriching the population of desired cells by a factor of at least 100, e.g., by 1000, 10,000, 100,000, or even 1,000,000 relative to one or more non-desired cell types.

Some devices for the separation of particles rely on size-based separation with or without simultaneous cell binding. Some size-based separation devices include one or more arrays of obstacles that cause lateral displacement of CTCs and other components of fluids, thereby offering mechanisms of enriching or otherwise processing such components. The array(s) of obstacles for separating particles according to size typically define a network of gaps, wherein a fluid passing through a gap is divided unequally into subsequent gaps. Both sieve and array sized-based separation devices can incorporate selectively permeable obstacles as described above with respect to cell-binding devices.

Devices including an array of obstacles that form a network of gaps can include, for example, a staggered two-dimensional array of obstacles, e.g., such that each successive row is offset by less than half of the period of the previous row. The obstacles can also be arranged in different patterns. Examples of possible obstacle shapes and patterns are discussed in more detail in WO 2004/029221.

In some embodiments, the device can provide separation and/or enrichment of CTCs using array-based size separation methods, e.g., as described in U.S. Pat. Pub. No. 2007/0026413. In general, the devices include one or more arrays of selectively permeable obstacles that cause lateral displacement of large particles such as CTCs and other components suspended in fluid samples, thereby offering mechanisms of enriching or otherwise processing such components, while also offering the possibility of selectively binding other, smaller particles that can penetrate into the voids in the dense matrices of nanotubes that make up the obstacles. Devices that employ such selectively permeable obstacles for size, shape, or deformability based enrichment of particles, including filters, sieves, and enrichment or separation devices, are described in International Publication Nos. 2004/029221 and 2004/113877; Nagrath et al., Nature 2007, 450:1235-1239; Huang et al. Science 304:987-990 (2004), U.S. Publication No. 2004/0144651, U.S. Pat. Nos. 5,837,115 and 6,692,952, and U.S. Application Nos. 60/703,833, 60/704,067, and Ser. No. 11/227,904; devices useful for affinity capture, e.g., those described in International Publication No. 2004/029221 and U.S. application Ser. No. 11/071,679; devices useful for preferential lysis of cells in a sample, e.g., those described in International Publication No. 2004/029221, U.S. Pat. No. 5,641,628, and U.S. Application No. 60/668,415; devices useful for arraying cells, e.g., those described in International Publication No. 2004/029221, U.S. Pat. No. 6,692,952, and U.S. application Ser. Nos. 10/778,831 and 11/146,581; and devices useful for fluid delivery, e.g., those described in U.S. application Ser. Nos. 11/071,270 and 11/227,469. Two or more devices can be combined in series, e.g., as described in International Publication No. WO 2004/029221. All of the foregoing are incorporated by reference herein.

In some embodiments, a device can contain obstacles that include binding moieties, e.g., monoclonal antibodies or antigen-binding fragments thereof, that selectively bind to cadherin cancer cell surface markers, e.g., on particular cell types, e.g., tumor cells. All of the obstacles of the device can include these binding moieties; alternatively, only a subset of the obstacles includes them. Devices can also include additional modules, e.g., a cell counting module or a detection module, which are in fluid communication with the microfluidic channel device. For example, the detection module can be configured to visualize an output sample of the device.

In one example, a detection module can be in fluid communication with a separation or enrichment device. The detection module can operate using any method of detection disclosed herein, or other methods known in the art. For example, the detection module includes a microscope, a cell counter, a magnet, a biocavity laser (see, e.g., Gourley et al., J. Phys. D: Appl. Phys., 36: R228-R239 (2003)), a mass spectrometer, a PCR device, an RT-PCR device, a microarray, or a hyperspectral imaging system (see, e.g., Vo-Dinh et al., IEEE Eng. Med. Biol. Mag., 23:40-49 (2004)). In some embodiments, a computer terminal can be connected to the detection module. For instance, the detection module can detect a label that selectively binds to cells, proteins, or nucleic acids of interest, e.g., DNA, mRNA, or protein for a cadherin cancer cell surface marker as described herein.

In some embodiments, the microfluidic system includes (i) a device for separation or enrichment of CTCs; (ii) optionally a device for lysis of the enriched CTCs; and (iii) a device for detection of DNA, mRNA, or proteins, e.g., DNA, mRNA, or protein for a cadherin cancer cell surface marker as described herein.

Other microfluidic platforms have been described; see, e.g., Sun et al., Cancer Res 2010, 70:6128-6138.

In some embodiments, a device for affinity-based particle capture in microfluidic devices having grooves is used. A micro-channel formed in a microfluidic device can be treated to capture particles suspended in a fluid flowing through the channel. A particle capture efficiency of the microfluidic device can be defined as a ratio of a number of particles captured in the channel and a total number of particles flowed through the channel. Grooves are formed extending into the walls of the micro-channel to create flow patterns in the fluid that promote an interaction between the particles suspended in the fluid and inner surfaces of the walls of the channel. The increased interaction can lead to an increase in a number of particles captured in the channel, and consequently, in the particle capture efficiency of the microfluidic device. The efficiency can further be increased by tailoring structural features of the microfluidic device including, for example, device substrate material, channel and groove dimensions, and the like, as well as fluid flow parameters such as flow rates based on types of particles and the types of fluids in which the particles are suspended. In some embodiments, the grooves are arranged in a herringbone pattern formed by arranging grooves in a column in the micro-channel. Particles are captured in the micro-channel of the microfluidic device by forming grooves in a wall of the micro-channel, coating an adherent on the inner surfaces of the walls of the micro-channel, and flowing particles suspended in the fluid through the micro-channel. In such implementations, the adherent can be an antibody, for example, an antibody to a cadherin as described herein. See, e.g., the herringbone devices described in Stott et al. PNAS 107(43):18392-7 (2010); and WO 2010/036912.

In some embodiments, a device can separate and focus streams of particles to equilibrium positions within a channel flow field based, at least in part, on inertial lift forces. In rectangular channels, this can lead, for example, to four streams of focused particles spaced a distance apart from a center of each of the four rectangular faces. For certain rectangular geometries, this four-fold symmetry can be reduced to a two-fold symmetry, with streams of particles spaced apart from each of two opposed faces of the channel. Methods and structures that decrease the symmetry of the system using a variety of forces, including, for example, electromagnetic, magnetic, centrifugal, hydrodynamic, thermal, sonic, optical, and/or dielectrophoretic forces or combinations thereof can be used. Although any force may be used to bias a particular potential minimum within the channel flow field, utilizing centrifugal forces with a curved channel structure has certain advantages. In this case, the force will increase with the square of the flow rate based only on a minor geometric change with no additional mechanical or electrical parts required. For example, the symmetry may be reduced by using inertial forces inherent in the flow through an S-shaped rectangular channel to result in a two-fold symmetry (down from four-fold) with a majority of the particles aligned with the flow in a periodic manner not corresponding to the period of the underlying channel. The geometry of the channel may also be used to change symmetry either by changing the radius of curvature or the width of the channel in a periodic manner (the channels thus curving asymmetrically) to create a single focused particle stream. See, e.g., WO 2008/130977.

Devices can include one or more arrays of obstacles that allow lateral displacement of circulating tumor cells and other components of fluids, thereby offering mechanisms of enriching or otherwise processing such components. Devices that employ obstacles for this purpose are described, e.g., in Huang et al. Science 304, 987-990 (2004) and U.S. Publication No. 20040144651. The devices for separating particles according to size typically employ an array of a network of gaps, wherein a fluid passing through a gap is divided unequally into subsequent gaps. The array can include a network of gaps arranged such that fluid passing through a gap is divided unequally, even though the gaps may be identical in dimensions. The method uses a flow that carries cells to be separated through the array of gaps. The flow is aligned at a small angle (flow angle) with respect to a line-of-sight of the array. Cells having a hydrodynamic size larger than a critical size migrate along the line-of-sight, i.e., laterally, through the array, whereas those having a hydrodynamic size smaller than the critical size follow the average flow direction. Flow in the device occurs under laminar flow conditions. Devices are optionally configured as continuous-flow devices. See, e.g., U.S. Pat. No. 7,988,840.

In some embodiments, the present invention includes devices (e.g., microfluidic devices) that contain a plurality of magnetic particles. By coating these magnetic particles with appropriate capture moieties, e.g., monoclonal antibodies or antigen-binding fragments thereof that bind to cancer cell surface markers as described herein (e.g., one or more cadherins, optionally with additional markers), it is possible to selectively bind circulating tumor cells through affinity mechanisms. In some embodiments, the magnetic particles are fixed obstacles set in a channel in a device. In its simplest embodiment, the device includes a channel having magnetic regions to which magnetic particles can magnetically attach to create a textured surface, with which cells passing through the channel can come into contact. The magnetic particles can serve to texture the channel, and through the appropriate choice of magnetic particle size and shape relative to the dimensions of the channel, it is possible to provide a texture that enhances interactions between the cells of interest and the magnetic particles. The magnetic particles can be magnetically attached to hard magnetic regions of the channel or to soft magnetic regions that are actuated to produce a magnetic field. In addition, these magnetic particles can be released from defined locations within the channel, e.g., by increasing the overall flow rate of the fluid flowing through the device, decreasing the magnetic field, or through some combination of the two. In some embodiments, a spatially nonuniform permanent magnet or electromagnet may be used to create organized and in some cases periodic arrays of magnetic particles within an otherwise untextured microfluidic channel (Deng et al. Applied Physics Letters, 78, 1775 (2001)). An electromagnetic may be employed to create a non-uniform magnetic field in a device. The non-uniform filed creates regions of higher and lower magnetic field strength, which, in turn, will attract magnetic particles in a periodic arrangement within the device. Other external magnetic fields may be employed to create magnetic regions to which magnetic particles attach. A hard magnetic material may also be used in the fabrication of the device, thereby obviating the need for electromagnets or external magnetic fields. In one embodiment, the device contains a plurality of channels having magnetic regions, e.g., to increase volumetric throughput. Further, these channels may be stacked vertically. The devices described herein can all include a spiral channel that is designed to apply differential inertial focusing to the blood sample. See, e.g., US20100055758.

In some embodiments, a device can contain one or more structures that deterministically deflect particles, in a fluid, having a hydrodynamic size above a critical size in a direction not parallel to the average direction of flow of the fluid in the structure. An exemplary structure includes an array of obstacles that form a network of gaps, wherein a fluid passing through the gaps is divided unequally into a major flux and a minor flux so that the average direction of the major flux is not parallel to the average direction of fluidic flow in the channel, and the major flux from the first outer region is directed either toward the second outer region or away from the second outer region, wherein the particles are directed into the major flux. The array of obstacles preferably includes first and second rows displaced laterally relative to one another so that fluid passing through a gap in the first row is divided unequally into two gaps in the second row. Such structures may be arranged in series in a single channel, in parallel in the same channel, e.g., a duplex configuration, in parallel in multiple channels in a device, or combinations thereof. Each channel will have at least one inlet and at least one outlet. A single inlet and outlet may be employed for two or more structures in parallel, in the same or different channels. Alternatively, each structure may have its own inlet and outlet or a single structure may contain multiple inlets and outlets, e.g., to introduce or collect two different fluids simultaneously. See, e.g., U.S. Pat. No. 8,021,614.

Also included herein are any and all of the above-described devices, having disposed therein an agent that binds a cancer cell surface marker selected from the group consisting of cadherin 1 (CDH1), CDH2, CDH3, CDH4, CDH5, CDH9, CDH11, CDH17, CDH19, protocadherin 9 (PCDH9) and/or PCDH beta 13 (PCDHb13), plus one or more additional cancer cell surface markers, e.g., EpCAM. In some embodiments, the devices comprise agents that bind to cadherin 3 and agents that bind to cadherin 11. In some embodiments, the devices comprise agents that bind to cadherin 3, agents that bind to cadherin 11, and agents that bind to EpCAM.

Surface-based Separation Methods

In some embodiments, the methods and devices include the use of surfaces, e.g., arrays or beads, e.g., magnetic beads, that are coated with a binding agent as described herein to allow the surfaces to bind specifically to cells expressing a cadherin cancer cell surface marker as described herein. In some embodiments, the methods can include the use of magnetic beads coated with one or more binding agents, e.g., antibodies or antigen-binding fragments thereof, that bind to a cadherin cancer cell surface marker as described herein. In some embodiments, each bead is coated with antibodies that bind to only one cadherin cancer cell surface marker as described herein; in some embodiments, each bead is coated with antibodies to a plurality of cadherin markers, such that each bead can bind to more than one cadherin cancer cell surface marker as described herein. In this way, the cancer cells are "labeled" with the beads. A number of magnetic beads are known in the art and can be used for the methods described herein. For example, latex beads that include an iron oxide component, e.g., as a core or admixed into the latex, can be used. Methods for making magnetic beads are known in the art; see, e.g., US2006/0154309, Marik et al., Journal of Magnetism and Magnetic Materials, 264(2-3):153-157 (2003).

Cancer cells labeled with the beads or bound to a surface can be captured from the sample using methods known in the art. For example, in the case of magnetic beads, magnetic cell separation methods as known in the art can be used, e.g., as described in U.S. Pat. No. 5,514,340, US20110059500, US2006/0154309, US 2010/0159556, and PCT US/93/04145.

EXAMPLES

The invention is further described in the following examples, which do not limit the scope of the invention described in the claims.

Example 1. Identification of Candidate Cancer Cell Surface Markers

To identify potential candidate cancer cell surface markers, RNA expression in human CTC samples was analyzed. A herringbone CTC capture device ($^{Hb}$CTC-chip; see, e.g., Stott et al. PNAS 107(43):18392-7 (2010); WO 2010/036912) was used to capture CTCs from 12 metastatic pancreatic cancer patients. RNA was extracted from the $^{Hb}$CTC-chip as well as a paired control non-capture IgG herringbone device. The control device allowed for the ability to extract genes upregulated in CTCs.

Four cadherin family members were identified in this preliminary screen, as shown in Table 1.

TABLE 1

| | |
|---|---|
| CDH4 | cadherin 4, type 1, R-cadherin (retinal) |
| CDH9 | cadherin 9, type 2 (T1-cadherin) |
| PCDH9 | protocadherin 9 |
| PCDHB13 | protocadherin beta 13 |

Example 2. Cadherin Expression in CTCs

A targeted search for cadherins expressed in CTCs was undertaken. The results of the search identified CDH4 and CDH9 as potential cadherins expressed in CTCs. CDH4 was analyzed further in cell line models, which revealed expression in the highly metastatic breast cancer cell line MDA-MB231 by Western blot (FIG. 1).

Immunofluorescent staining confirmed expression of CDH4 in this cell line, but almost no expression of EpCAM despite its highly metastatic phenotype (FIG. 2). Therefore, this particular cancer cell line would not be captured on current CTC devices based on EpCAM, but would be captured with an anti-CDH4 device.

A more comprehensive bioinformatics analysis of cadherins was then taken in primary and secondary tumor expression databases. Candidates were evaluated for the presence of significant levels of expression in tumors, but near absence in healthy donor whole blood analytes in the database (see FIGS. 3-49). Cadherin candidates were then refined further by using the Oncomine™ database to identify potential CTC capture antigens (FIG. 2).

In summary, cadherins represent novel CTC capture antigens obtained from RNA sequencing in pancreatic CTCs. CDH4 is expressed on cancer cell lines that do not express EpCAM and therefore a viable capture marker.

More extensive analysis of primary tumors evaluated by gene expression microarrays has also identified CDH 1, 2, 3, 5, 11, and 19 as promising highly expressed cadherins in a wide variety of tumors but nearly absent in normal blood.

Example 3. Cadherins Capture CTCs In Vivo

The ability to capture CTCs from an experimental animal implanted with human cancer cells was determined. Cadherin expression in normal breast epithelial cells (NBE), CD44+ cells isolated from pleural effusions (P_CD44+) of human breast cancer patients, and CD44+(X_CD44+) and CD44− (X_CD44−) cells isolated from tumor xenografts grown in mice.

The results are shown in FIGS. 50A-50D, and demonstrate that the differential expression of cadherins in tumor cell subfractions relative to that observed in normal breast epithelial cells.

TGF-beta treatment of epithelial cells induces an epithelial-to-mesenchymal transition (EMT). As shown in FIGS. 51A-F, some cadherins increase, others decrease and some do not change during EMT, providing further evidence that a cocktail of cadherins would capture both epithelial and mesenchymal tumor cells.

Example 4. Analysis of Cadherin Expression

First, Western blotting was used to analyze expression of EpCAM and cadherins 1, 2, 3, 5, 11, and 17, in various cancer cell lines, including the following: Breast: MCF10A, SKBR3, MDA-MB-231*, (MCF10A-LBX1); Prostate: PC3-9; Lung: H1650, CaLu1*, HCC827; and Colon: SW620, HCT116.

Briefly, total protein isolated from above cells lines was separated by SDS-PAGE, transferred onto polyvinylidene fluoride (PVDF) membranes and analyzed using antibodies against EPCAM and cadherins 1, 2, 3, 5, 11, and 17.

The summary of western blot results shown in Table 2, demonstrates widespread expression of Cadherins, especially CDH3 and CDH11, and that expression of CDH3 and CDH11 complement expression of EpCAM. It is well established that antibody reactivity towards proteins varies depending on the application used. For example, some antibodies work better on western blot than with FACS sorting. Hence several antibodies were tested to ensure specific detection.

FACS analysis was used to further determine the ability of panels of anti-cadherin antibodies, with and without EpCAM, to capture tumor cells. This example provides evidence that a cocktail of antibodies against cell surface proteins, e.g., the epithelial-specific EpCAM and the epithelial and mesenchyme specific-Cadherins, will capture the entire spectrum of CTCs of different lineages.

Cells were cultured to 70-80% confluence and released from the culture dish using cell dissociation solution. Cells (250,000) were resuspended in 300 µl of PBS and 100 µl of antibody against each protein (cadherin 3 (AbCAM), 11 (R&D), EpCAM (Veridex)), either alone or in combination, for 30 minutes at 4 degrees. Isotype matched IgG was used as control. After incubation with appropriate secondary antibodies (30 minutes, 4 degrees), the cells were washed and analyzed by FACS. Over all about 10,000 cells were sorted to obtain the data provided.

The data, shown in Table 3, demonstrates that an antibody cocktail against EpCAM and cadherins 3 and 11 captures cancer cell lines of both epithelial and mesenchymal phenotypes at nearly ~90%. [10 out of 10 cell lines (n=2).

Thus, combining antibodies against CDH3 and CDH11 with an EpCAM antibody was able to detect 90% of the tumor cells irrespective of their epithelial or mesenchymal state (it should be noted that MDA-MB-231, CaLu1 and PC3-9 cells express lower levels of EpCAM and that MDA-MB-231 and CaLu1 are highly mesenchymal in culture). Thus, sorting with panels including antibodies to CDH11 and EpCAM, or to CDH3, CDH11, and EpCAM, captured nearly or greater than 90% of cells in a wide variety of cell types.

Figure 52A:
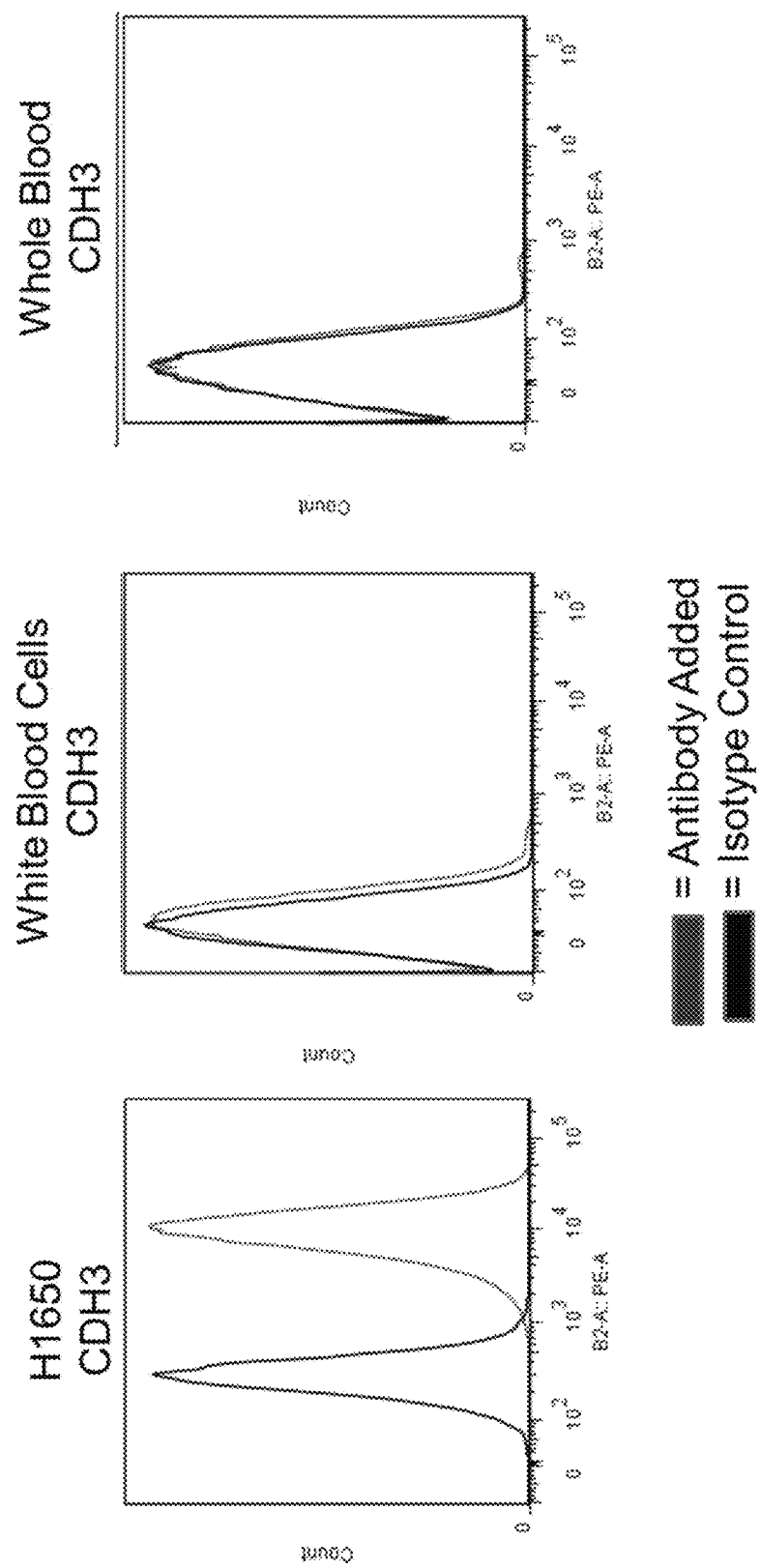
FIGS. 52A-B are line graphs showing that while Abcam 89900 anti-CDH3 antibodies bound robustly to lung cancer H1650 cells (FIG. 52A, left panel), and RnD 1790 anti-CDH11 antibodies bound to PC3-9 prostate cancer cells (FIG. 52B, left panel), neither antibody bound significantly to white blood cells (52A-B, middle panels) or whole blood (52A-B, right panels).
Figure 52B:
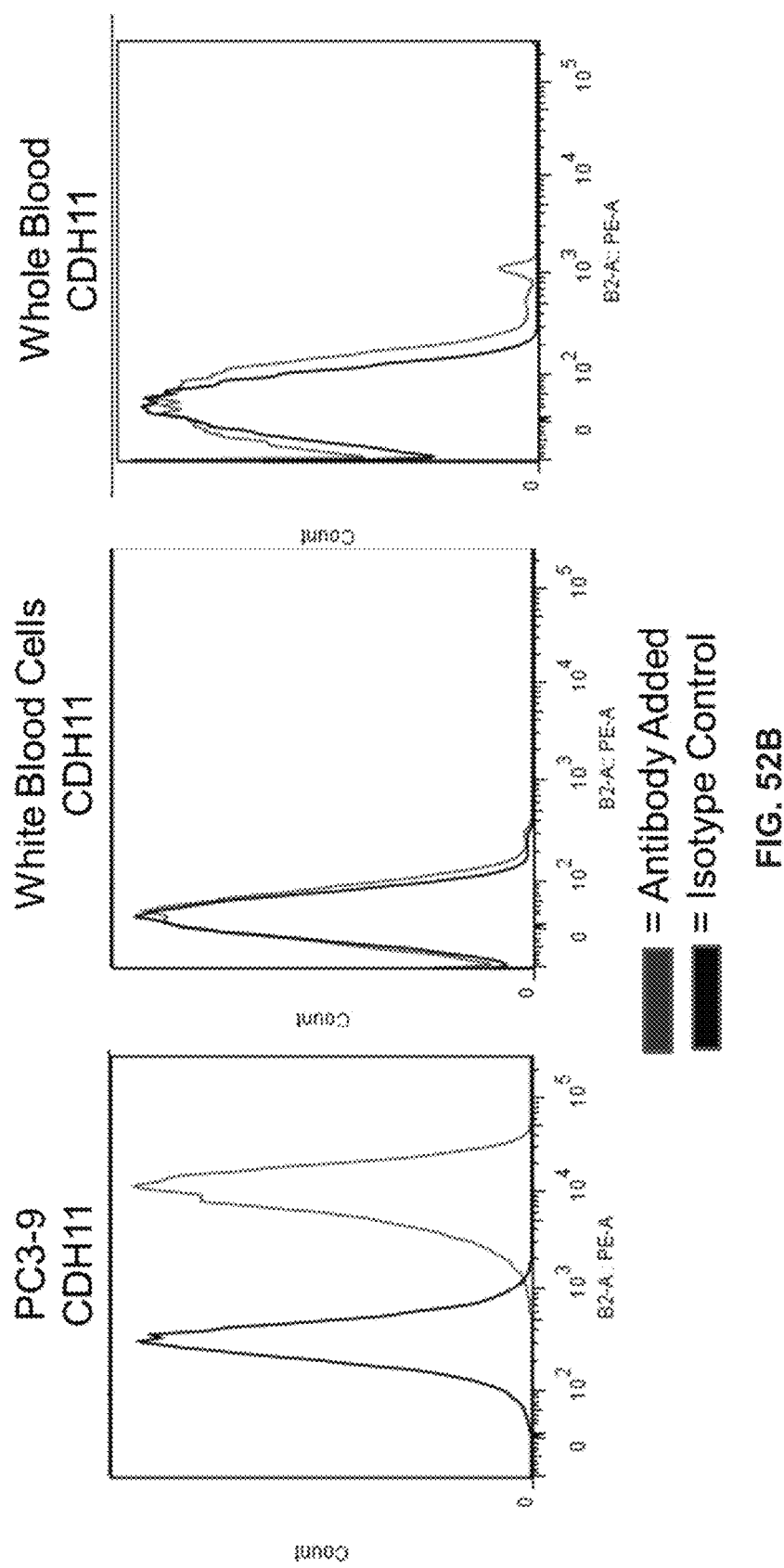

FACS was further used to determine whether antibodies to CDH3 and CDH11 would also bind to whole blood or white blood cells. The results, shown in FIGS. 52A-B, shown that while Abcam 89900 anti-CDH3 antibodies bound robustly to lung cancer H1650 cells (FIG. 52A, left panel), and RnD 1790 anti-CDH11 antibodies bound to PC3-9 prostate cancer cells (FIG. 52B, left panel), neither antibody bound significantly to white blood cells (52A-B, middle panels) or whole blood (52A-B, right panels).

When the expression results were compared between FACS and Western blotting, excellent concordance was seen with several of the antibodies tested (Table 4).

Figure 53:
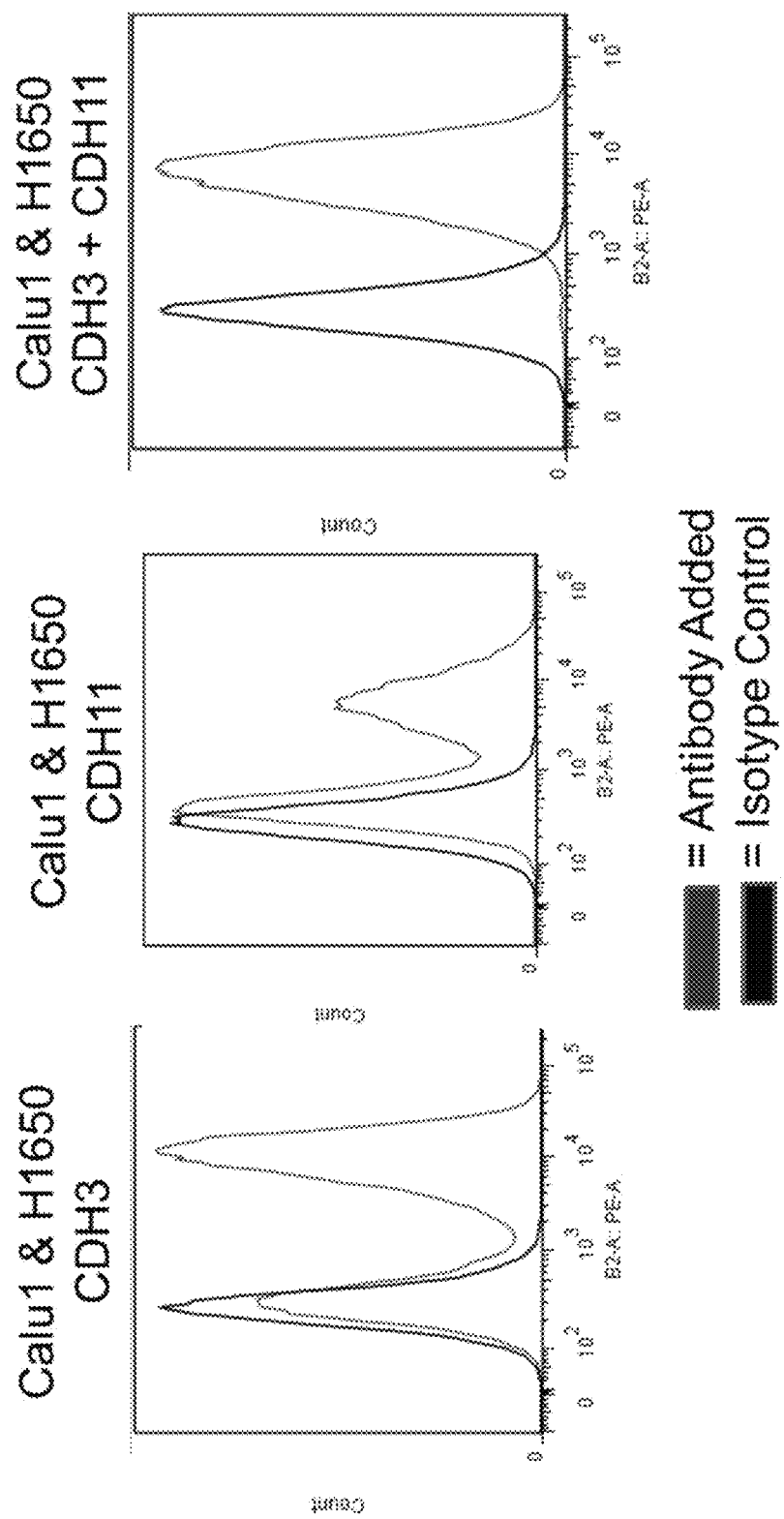
FIG. 53 is a line graph showing the ability of a combination of CDH3 and CDH11 antibodies to capture cancer cells in a mixture of cells. Calu1 breast cancer cells and H1650 lung cancer cells were mixed and contacted with anti-CDH3 Abcam 89900 antibodies and RnD anti-CDH11 1790 antibodies. This combination was extremely effective in capturing nearly all of the cancer cells.

Finally, the ability of a combination of CDH3 and CDH11 antibodies to capture cancer cells in a mixture of cells was tested. Calu1 breast cancer cells and H1650 lung cancer cells were mixed and contacted with anti-CDH3 Abcam 89900 antibodies and RnD anti-CDH11 1790 antibodies. The results, shown in FIG. 53 and Table 5, demonstrate that this combination was extremely effective in capturing nearly all of the cancer cells.

TABLE 2

|  | SKBR3 | H1650 | PC3-9 | MB-231 | LBX1 | MCF10A | HCC827 | Calu-1 | SW620 | HCT116 |
|---|---|---|---|---|---|---|---|---|---|---|
| (E) CDH1 Abcam 1416 |  | + |  |  |  | + | + |  | + | + |
| (E) CDH1 Cell Signaling 3195 |  | + |  |  |  | + | + |  | + | + |
| (E) CDH1 BD Transduction 610181 |  | + |  |  |  | + | + |  | + | + |
| CDH2 eBioscience 14325982 |  |  |  |  |  |  |  | + |  |  |
| (N) CDH2 Invitrogen 333900 |  |  | + |  | + |  |  | + |  |  |
| (N) CDH2 Abcam 124397 |  |  | + |  | + |  |  | + |  |  |
| (P) CDH3 BD Transduction 610227 |  | + |  |  |  | + | + |  |  | + |
| (P) CDH3 Abcam12222 |  |  |  |  |  |  |  |  |  |  |
| (P) CDH3 Abcam 89900 |  | + |  |  | + | + | + |  |  | + |
| (P) CDH3 RnD MAB861 |  | + |  |  | + | + | + |  |  | + |
| (VE) CDH5 Abcam 7047 |  |  |  |  | multiple bands |  |  |  |  |  |
| (VE) CDH5 Cell Signaling 2500 | + |  |  |  |  |  |  |  |  |  |
| CDH11 Millipore MAB2014 |  |  |  |  |  |  |  |  |  |  |
| CDH11 Invitrogen 717600 | + | + | + | + | + | + | + | + | + | + |
| CDH11 Invitrogen 321700 |  |  | + | + |  |  |  | + |  |  |
| CDH11 RnD MAB1790 |  |  |  |  |  |  |  |  |  |  |
| CDH17 RnD BAF1032 |  |  |  |  |  |  |  |  |  |  |
| CDH17 Abcam 124266 |  |  |  |  |  |  |  |  |  |  |
| CDH17 Abcam 89305 |  |  |  |  |  |  |  |  |  |  |
| CDH17 AbD Serotec |  |  |  |  |  |  |  |  |  |  |
| EpCAM RnD BAF960 |  | + | + |  |  | + | + |  | + | + |
| EpCAM Veridex | + | + | + |  |  | + | + |  | + | + |

TABLE 3

|  | Lung | | | Colon | | Prostate | Breast | | | Br Ctrl |
| --- | --- | --- | --- | --- | --- | --- | --- | --- | --- | --- |
|  | CaLu1 | H1650 | HCC827 | HCT116 | SW620 | PC39 | MCF10A | SKBR3 | MB231 | LBX1 |
| EpCAM Veridex | *19.5 | 98.5 | 95.4 | 94.9 | 93 | *70.8 | 93.9 | 98.9 | *75.5 | *9.5 |
| CDH3 Abcam 89900 | *0.8 | 95.9 | 87.4 | 99.7 | *1.7 | *1.6 | 93.9 | *0.5 | *4.4 | 56.2 |
| CHD11 RnD 1790 | 92.9 | *10.9 | *13.9 | *10.4 | *2.4 | 94 | *6.7 | *17.7 | 93.8 | 41 |
| CDH3 & CDH11 | 91 | 63.6 | 67.9 | 99.1 | 2.3 | 92.5 | 93.8 | 9.6 | 90.6 | 50.5 |
| EpCAM & CDH3 | 19.2 | 97.5 | 87.5 | 85.7 | 89.9 | 86.2 | 97.2 | 83.6 | 72.1 | 47 |
| EpCAM & CDH11 | 93.5 | 97.5 | 94.9 | 99.7 | 98.8 | 96.9 | 96.4 | 98.8 | 95.8 | 13.6 |
| EpCAM & CDH3 &CDH11 | 92.9 | 98.5 | *88.9 | 99.1 | *78.5 | 97.6 | 97.6 | 98.9 | 95.3 | 45.4 |
| mslgG2b | 0.3 | 0.3 | 0.3 | 2 | 0.3 | 0.3 | 0.4 | 0.3 | 0.3 | 0.3 |
| mslgG1 | 0.3 | 0.9 | 0.3 | 2 | 0.3 | 0.3 | 0.4 | 0.3 | 0.3 | 0.3 |
| mslgG1 | 0.3 | 0.8 | 0.3 | 2 | 0.3 | 0.3 | 0.4 | 0.3 | 0.3 | 0.3 |
| mslgG1 &mslgG2b | 0.3 | 0.3 | 0.3 | 2 | 0.3 | 0.3 | 0.4 | 0.3 | 0.3 | 0.3 |
| mslgG1 &mslgG2b | 0.3 | 0.5 | 0.3 | 2 | 0.3 | 0.3 | 0.4 | 0.3 | 0.3 | 0.3 |

TABLE 4

Western Blotting

|  | Calu-1 | H1650 | HCC827 | HCT116 | SW620 | PC3-9 | MCF10A | SKBR3 | MB-231 | LBX1 |
| --- | --- | --- | --- | --- | --- | --- | --- | --- | --- | --- |
| (P) CDH3 Abcam |  | + | + | + |  |  | + |  |  | + |
| (P) CDH3 R&D |  | + | + | + |  |  | + |  |  | + |
| CDH11 Invitrogen | + |  |  |  |  | + |  |  | + |  |
| EpCAM RnD |  | + | + | + | + | + | + |  |  |  |
| EpCAM Veridex |  | + | + | + | + |  | + | + |  |  |

FACS

|  | Calu1 | H1650 | HCC827 | HCT116 | SW620 | PC39 | MCF10A | SKBR3 | MB-231 | LBX1 |
| --- | --- | --- | --- | --- | --- | --- | --- | --- | --- | --- |
| CDH3 Abcam | 0.8 | 95.9 | 87.4 | 99.7 | 1.7 | 1.6 | 93.9 | 0.5 | 4.4 | 56.2 |
| CHD11 R&D | 92.9 | 10.9 | 13.9 | 10.4 | 2.4 | 94 | 6.7 | 17.7 | 93.8 | 41 |
| EpCAM Veridex | 19.5 | 98.5 | 95.4 | 94.9 | 93 | 70.8 | 93.9 | 98.9 | 75.5 | 9.5 |
| CDH3 & CDH11 | 91 | 63.6 | 67.9 | 99.1 | 2.3 | 92.5 | 93.8 | 9.6 | 90.6 | 50.5 |
| EpCAM & CDH3 | 19.2 | 97.5 | 87.5 | 85.7 | 89.9 | 86.2 | 97.2 | 83.6 | 72.1 | 47 |
| EpCAM & CDH11 | 93.5 | 97.5 | 94.9 | 99.7 | 98.8 | 96.9 | 96.4 | 98.8 | 95.8 | 13.6 |
| EpCAM & CDH3 &CDH11 | 92.9 | 98.5 | 88.9 | 99.1 | 78.5 | 97.6 | 97.6 | 98.9 | 95.3 | 45.4 |

TABLE 5

| Lung | Calu1 | H1650 | Calu1 + H1650 |
| --- | --- | --- | --- |
| CDH3 (Abcam 89900) | 0.9 | 99.5 | 60.5 |
| CHD11 (RnD 1790) | 94.2 | 8.3 | 41.9 |
| CDH3 & CDH11 | N/A | N/A | 93.2 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A device for separation of cells in a sample, the device comprising an inlet, an outlet, and one or more areas coated with agents that bind to each of cancer cell surface markers cadherin 1 (CDH1), CDH2, CDH3, CDH4, CDH5, CDH9, CDH11, CDH17, CDH19, protocadherin 9 (PCDH9) and PCDH beta 13 (PCDHb13), configured to separate cells that express the cancer cell surface markers from cells that do not express the cancer cell surface markers.

2. The device of claim 1, wherein the device is a microfluidic device.

3. The device of claim 1, wherein the device comprises a micro-channel disposed between the inlet and the outlet, and a herringbone pattern formed by arranging grooves in the micro-channel, and the agents that bind the cancer cell surface marker is disposed on one or more of walls of the microchannel.

4. The device of claim 1, further comprising one or more areas coated with an agent that binds to an additional cancer cell surface marker selected from the group consisting of EpCAM, MUC-1, HER2, EGFR, EphB4, and CEA.

5. The device of claim 4, wherein the additional cancer cell surface marker is EpCAM.

6. The device of claim 1, wherein the agents that bind to each of the cancer cell surface markers are coated on a magnetic bead.

7. The device of claim 1, wherein the agents that bind to each of the cancer cell surface markers are antibodies or antigen-binding fragments thereof.

8. The device of claim 2, wherein the microfluidic device separates tumor cells based on inertial lift forces or fluid flow patterns.

9. The device of claim 1, wherein the cells that express the cancer cell surface markers are circulating tumor cells.

10. The device of claim 4, wherein the agent that binds to the additional cancer cell surface marker is an antibody or antigen-binding fragment thereof.

11. A device for separation of cells in a sample, the device comprising an inlet, an outlet, and magnetic beads, wherein the magnetic beads are coated with agents that bind to each of cancer cell surface markers cadherin 1 (CDH1), CDH2, CDH3, CDH4, CDH5, CDH9, CDH11, CDH17, CDH19, protocadherin 9 (PCDH9) and PCDH beta 13 (PCDHb13), wherein the device is configured to separate cells that express the cancer cell surface markers from cells that do not express the cancer cell surface markers.

12. The device of claim 11, wherein the magnetic beads are further coated with an agent that binds to an additional cancer cell surface marker selected from the group consisting of EpCAM, MUC-1, HER2, EGFR, EphB4, and CEA.

13. The device of claim 12, wherein the additional cancer cell surface marker is EpCAM.

14. The device of claim 11, wherein the agents that bind to each of the cancer cell surface markers are antibodies or antigen-binding fragments thereof.

15. The device of claim 11, wherein the magnetic beads are latex beads comprising an iron oxide component.

16. The device of claim 12, wherein the agent that binds to the additional cancer cell surface marker is an antibody or antigen-binding fragment thereof.

* * * * *